(12) United States Patent
Loesener et al.

(10) Patent No.: US 11,896,782 B2
(45) Date of Patent: Feb. 13, 2024

(54) PRIMING AND TUNNELING SYSTEM FOR A RETROGRADE CATHETER ASSEMBLY

(71) Applicant: C. R. Bard, Inc., Franklin Lakes, NJ (US)

(72) Inventors: German Loesener, Riverton, UT (US); Bradley Forsyth, Sandy, UT (US); Jason R. Stats, Layton, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 601 days.

(21) Appl. No.: 16/640,688

(22) PCT Filed: Aug. 23, 2018

(86) PCT No.: PCT/US2018/047831
§ 371 (c)(1),
(2) Date: Feb. 20, 2020

(87) PCT Pub. No.: WO2019/040801
PCT Pub. Date: Feb. 28, 2019

(65) Prior Publication Data
US 2020/0368496 A1 Nov. 26, 2020

Related U.S. Application Data

(60) Provisional application No. 62/631,471, filed on Feb. 15, 2018, provisional application No. 62/549,354,
(Continued)

(51) Int. Cl.
*A61M 25/01* (2006.01)
*A61M 25/00* (2006.01)
(Continued)

(52) U.S. Cl.
CPC .... *A61M 25/0194* (2013.01); *A61M 25/0028* (2013.01); *A61M 25/0097* (2013.01);
(Continued)

(58) Field of Classification Search
CPC ............ A61M 25/0097; A61M 39/105; A61M 39/12; A61M 25/0194; A61M 25/0102; A61M 25/02; A61M 2025/0286
See application file for complete search history.

(56) References Cited

U.S. PATENT DOCUMENTS 2,471,623 A   5/1949   Hubbell
2,709,542 A   5/1955   Eller
(Continued)

FOREIGN PATENT DOCUMENTS

EP   0183396 A1   6/1986
EP   0439263 A1   7/1991
(Continued)

OTHER PUBLICATIONS

Arrow® Cannon™ II Plus Product Brochure, Feb. 2012.
(Continued)

*Primary Examiner* — Katherine H Schwiker
*Assistant Examiner* — Rachel T. Smith
(74) *Attorney, Agent, or Firm* — Rutan & Tucker LLP

(57) ABSTRACT

Disclosed herein are catheter assemblies and methods thereof that address various aspects of at least the retrograde tunneling technique. The catheter assemblies include, but are not limited to, catheter assemblies configured for vascular access, catheter assemblies configured for priming, catheter assemblies configured for tunneling, and mechanisms for connecting catheter tubes to their respective catheter assemblies. The methods include, but are not limited to, priming, tunneling, and connecting catheter tubes to their respective catheter assemblies.

6 Claims, 48 Drawing Sheets

Related U.S. Application Data filed on Aug. 23, 2017, provisional application No. 62/549,359, filed on Aug. 23, 2017.

(51) Int. Cl.
*A61M 25/02* (2006.01)
*A61M 39/10* (2006.01)

(52) U.S. Cl.
CPC ........ *A61M 25/0102* (2013.01); *A61M 25/02* (2013.01); *A61M 39/105* (2013.01); *A61M 2025/0286* (2013.01)

(56) References Cited

U.S. PATENT DOCUMENTS

| | | | |
|---|---|---|---|
| 3,176,690 A | 4/1965 | H'Doubler |
| D217,795 S | 6/1970 | Spaven |
| 3,527,226 A | 9/1970 | Hakim |
| 3,565,078 A | 2/1971 | Vailliancourt et al. |
| 3,572,340 A | 3/1971 | Lloyd et al. |
| 3,650,507 A | 3/1972 | Nyberg |
| 3,672,372 A | 6/1972 | Heimlich |
| 3,805,794 A | 4/1974 | Schlesinger |
| 3,879,516 A | 4/1975 | Wolvek |
| 3,921,631 A | 11/1975 | Thompson |
| 4,000,739 A | 1/1977 | Stevens |
| 4,029,095 A | 6/1977 | Pena et al. |
| 4,068,659 A | 1/1978 | Moorehead |
| 4,112,949 A | 9/1978 | Rosenthal et al. |
| 4,123,091 A | 10/1978 | Cosentino et al. |
| 4,134,402 A | 1/1979 | Mahurkar |
| 4,198,973 A | 4/1980 | Millet |
| 4,233,974 A | 11/1980 | Desecki et al. |
| 4,235,232 A | 11/1980 | Spaven et al. |
| 4,256,106 A | 3/1981 | Shoor |
| 4,256,116 A | 3/1981 | Meretsky et al. |
| 4,267,835 A | 5/1981 | Barger et al. |
| 4,296,747 A | 10/1981 | Ogle |
| 4,306,562 A | 12/1981 | Osborne |
| 4,340,052 A | 7/1982 | Dennehey et al. |
| 4,385,631 A | 5/1983 | Uthmann |
| 4,387,879 A | 6/1983 | Tauschinski |
| 4,391,029 A | 7/1983 | Czuba et al. |
| 4,405,313 A | 9/1983 | Sisley et al. |
| 4,411,654 A | 10/1983 | Boarini et al. |
| 4,412,832 A | 11/1983 | Kling et al. |
| 4,424,833 A | 1/1984 | Spector et al. |
| D272,651 S | 2/1984 | Mahurkar |
| 4,430,081 A | 2/1984 | Timmermans |
| 4,431,426 A | 2/1984 | Groshong et al. |
| 4,432,759 A | 2/1984 | Gross et al. |
| 4,436,519 A | 3/1984 | O'Neill |
| 4,439,179 A | 3/1984 | Lueders et al. |
| 4,445,893 A | 5/1984 | Bodicky |
| 4,449,973 A | 5/1984 | Luther |
| 4,453,928 A | 6/1984 | Steiger |
| 4,468,224 A | 8/1984 | Enzmann et al. |
| 4,473,067 A | 9/1984 | Schiff |
| 4,490,003 A | 12/1984 | Robinson |
| RE31,855 E | 3/1985 | Osborne |
| 4,502,502 A | 3/1985 | Krug |
| 4,512,766 A | 4/1985 | Vailancourt |
| 4,535,818 A | 8/1985 | Duncan et al. |
| 4,539,003 A | 9/1985 | Tucker |
| 4,543,087 A | 9/1985 | Sommercorn et al. |
| 4,553,959 A | 11/1985 | Hickey et al. |
| 4,557,261 A | 12/1985 | Rügheimer |
| 4,568,329 A | 2/1986 | Mahurkar |
| 4,571,241 A | 2/1986 | Christopher |
| 4,573,974 A | 3/1986 | Ruschke |
| 4,581,012 A | 4/1986 | Brown et al. |
| 4,581,025 A | 4/1986 | Timmermans |
| 4,583,968 A | 4/1986 | Mahurkar |
| 4,591,355 A | 5/1986 | Hilse |
| 4,592,749 A | 6/1986 | Ebling et al. |
| 4,596,559 A | 6/1986 | Fleischhacker |
| 4,596,571 A | 6/1986 | Bellotti et al. |
| 4,610,665 A | 9/1986 | Matsumoto et al. |
| 4,619,643 A | 10/1986 | Bai |
| 4,623,327 A | 11/1986 | Mahurkar |
| 4,626,245 A | 12/1986 | Weinstein |
| 4,643,711 A | 2/1987 | Bates |
| 4,650,472 A | 3/1987 | Bates |
| 4,673,393 A | 6/1987 | Suzuki et al. |
| 4,675,004 A | 6/1987 | Hadford et al. |
| 4,675,020 A | 6/1987 | McPhee |
| 4,681,122 A | 7/1987 | Winters et al. |
| 4,682,978 A | 7/1987 | Martin |
| 4,692,141 A | 9/1987 | Mahurkar |
| 4,701,159 A | 10/1987 | Brown et al. |
| 4,722,725 A | 2/1988 | Sawyer et al. |
| 4,723,550 A | 2/1988 | Bales et al. |
| 4,723,948 A | 2/1988 | Clark et al. |
| 4,726,374 A | 2/1988 | Bales et al. |
| 4,738,658 A | 4/1988 | Magro et al. |
| 4,743,265 A | 5/1988 | Whitehouse et al. |
| 4,747,833 A | 5/1988 | Kousai et al. |
| 4,753,765 A | 6/1988 | Pande |
| 4,770,652 A | 9/1988 | Mahurkar |
| 4,772,266 A | 9/1988 | Groshong |
| 4,772,268 A | 9/1988 | Bates |
| 4,776,841 A | 10/1988 | Catalano |
| 4,784,644 A | 11/1988 | Sawyer et al. |
| 4,795,426 A | 1/1989 | Jones |
| 4,798,594 A | 1/1989 | Hillstead |
| 4,808,155 A | 2/1989 | Mahurkar |
| 4,832,687 A | 5/1989 | Smith, III |
| 4,842,582 A | 6/1989 | Mahurkar |
| 4,842,592 A | 6/1989 | Caggiani et al. |
| 4,850,955 A | 7/1989 | Newkirk |
| 4,865,593 A | 9/1989 | Ogawa et al. |
| 4,874,377 A | 10/1989 | Newgard et al. |
| 4,895,561 A | 1/1990 | Mahurkar |
| 4,895,570 A | 1/1990 | Larkin |
| 4,898,669 A | 2/1990 | Tesio |
| 4,906,237 A | 3/1990 | Johansson et al. |
| 4,909,798 A | 3/1990 | Fleischhacker et al. |
| RE33,219 E | 5/1990 | Daniell et al. |
| 4,921,479 A | 5/1990 | Grayzel |
| 4,929,235 A | 5/1990 | Merry et al. |
| 4,929,236 A | 5/1990 | Sampson |
| 4,932,633 A | 6/1990 | Johnson et al. |
| 4,932,938 A | 6/1990 | Goldberg et al. |
| 4,935,010 A | 6/1990 | Cox et al. |
| 4,936,826 A | 6/1990 | Amarasinghe |
| 4,946,133 A | 8/1990 | Johnson et al. |
| 4,946,449 A | 8/1990 | Davis, Jr. |
| 4,950,255 A | 8/1990 | Brown et al. |
| 4,952,359 A | 8/1990 | Wells |
| 4,960,412 A | 10/1990 | Fink |
| 4,966,588 A | 10/1990 | Rayman et al. |
| 4,983,168 A | 1/1991 | Moorehead |
| 4,997,424 A | 3/1991 | Little |
| 5,007,901 A | 4/1991 | Shields |
| 5,009,636 A | 4/1991 | Wortley et al. |
| 5,035,686 A | 7/1991 | Crittenden et al. |
| 5,041,095 A | 8/1991 | Littrell |
| 5,053,003 A | 10/1991 | Dadson et al. |
| 5,053,004 A | 10/1991 | Markel et al. |
| 5,053,013 A | 10/1991 | Ensminger et al. |
| 5,053,014 A | 10/1991 | Van Heugten |
| 5,053,023 A | 10/1991 | Martin |
| 5,057,073 A | 10/1991 | Martin |
| 5,059,170 A | 10/1991 | Cameron |
| 5,064,414 A | 11/1991 | Revane |
| 5,066,285 A | 11/1991 | Hillstead |
| 5,071,411 A | 12/1991 | Hillstead |
| 5,078,688 A | 1/1992 | Lobodzinski et al. |
| 5,085,645 A | 2/1992 | Purdy et al. |
| 5,092,857 A | 3/1992 | Fleischhacker |
| 5,098,392 A | 3/1992 | Fleischhacker et al. |
| 5,098,393 A | 3/1992 | Amplatz et al. |
| 5,106,368 A | 4/1992 | Uldall et al. |
| 5,108,380 A | 4/1992 | Herlitze et al. |

(56) References Cited

U.S. PATENT DOCUMENTS

| | | |
|---|---|---|
| 5,112,301 A | 5/1992 | Fenton, Jr. et al. |
| 5,112,323 A | 5/1992 | Winkler et al. |
| 5,114,408 A | 5/1992 | Fleischhaker et al. |
| 5,117,836 A | 6/1992 | Millar |
| 5,125,904 A | 6/1992 | Lee |
| 5,135,599 A | 8/1992 | Martin et al. |
| 5,137,524 A | 8/1992 | Lynn et al. |
| 5,141,497 A | 8/1992 | Erskine |
| 5,149,327 A | 9/1992 | Oshiyama |
| 5,154,701 A | 10/1992 | Cheer et al. |
| 5,156,592 A | 10/1992 | Martin et al. |
| 5,156,596 A | 10/1992 | Balbierz et al. |
| 5,158,545 A | 10/1992 | Trudell et al. |
| 5,158,553 A | 10/1992 | Berry et al. |
| 5,160,323 A | 11/1992 | Andrew |
| 5,163,903 A | 11/1992 | Crittenden et al. |
| 5,167,634 A | 12/1992 | Corrigan, Jr. et al. |
| 5,167,637 A | 12/1992 | Okada et al. |
| 5,169,393 A | 12/1992 | Moorehead et al. |
| 5,171,222 A | 12/1992 | Euteneuer et al. |
| 5,180,372 A | 1/1993 | Vegoe et al. |
| 5,186,431 A | 2/1993 | Tamari |
| 5,188,593 A | 2/1993 | Martin |
| 5,190,520 A | 3/1993 | Fenton, Jr. et al. |
| 5,190,528 A | 3/1993 | Fonger et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,976 A | 3/1993 | Herweck et al. |
| 5,201,722 A | 4/1993 | Moorehead et al. |
| 5,205,834 A | 4/1993 | Moorehead et al. |
| 5,207,650 A | 5/1993 | Martin |
| 5,209,723 A | 5/1993 | Twardowski et al. |
| 5,211,633 A | 5/1993 | Stouder, Jr. |
| 5,215,538 A | 6/1993 | Larkin |
| 5,221,255 A | 6/1993 | Mahurkar et al. |
| 5,221,256 A | 6/1993 | Mahurkar |
| 5,221,263 A | 6/1993 | Sinko et al. |
| 5,234,410 A | 8/1993 | Graham et al. |
| 5,234,438 A | 8/1993 | Semrad |
| 5,242,413 A | 9/1993 | Heiliger |
| 5,242,430 A | 9/1993 | Arenas et al. |
| 5,250,033 A | 10/1993 | Evans et al. |
| 5,251,873 A | 10/1993 | Atkinson et al. |
| 5,255,691 A | 10/1993 | Otten |
| 5,273,540 A | 12/1993 | Luther et al. |
| 5,273,546 A | 12/1993 | McLaughlin et al. |
| 5,275,583 A | 1/1994 | Crainich |
| 5,279,597 A | 1/1994 | Dassa et al. |
| 5,290,294 A | 3/1994 | Cox et al. |
| 5,304,142 A | 4/1994 | Liebl et al. |
| 5,304,156 A | 4/1994 | Sylvanowicz et al. |
| 5,306,240 A | 4/1994 | Berry |
| 5,312,337 A | 5/1994 | Flaherty et al. |
| 5,312,355 A | 5/1994 | Lee |
| 5,312,357 A | 5/1994 | Buijs et al. |
| 5,320,602 A | 6/1994 | Karpiel |
| 5,324,271 A | 6/1994 | Abiuso et al. |
| 5,324,274 A | 6/1994 | Martin |
| 5,330,437 A | 7/1994 | Durman |
| 5,334,157 A | 8/1994 | Klein et al. |
| 5,334,187 A | 8/1994 | Fischell et al. |
| 5,336,192 A | 8/1994 | Palestrant |
| 5,338,313 A | 8/1994 | Mollenauer et al. |
| 5,342,386 A | 8/1994 | Trotta |
| 5,348,537 A | 9/1994 | Wiesner et al. |
| 5,350,358 A | 9/1994 | Martin |
| 5,350,362 A | 9/1994 | Stouder, Jr. |
| 5,350,363 A | 9/1994 | Goode et al. |
| 5,360,397 A | 11/1994 | Pinchuk |
| 5,360,403 A | 11/1994 | Mische |
| 5,364,393 A | 11/1994 | Auth et al. |
| 5,368,574 A | 11/1994 | Antonacci et al. |
| 5,374,245 A | 12/1994 | Mahurkar |
| 5,378,230 A | 1/1995 | Mahurkar |
| 5,380,276 A | 1/1995 | Miller et al. |
| 5,382,241 A | 1/1995 | Choudhury et al. |
| 5,389,090 A | 2/1995 | Fischell et al. |
| 5,391,152 A | 2/1995 | Patterson |
| 5,395,352 A | 3/1995 | Penny |
| 5,397,311 A | 3/1995 | Walker et al. |
| 5,399,172 A | 3/1995 | Martin et al. |
| 5,401,245 A | 3/1995 | Haining |
| 5,405,320 A | 4/1995 | Twardowski et al. |
| 5,405,323 A | 4/1995 | Rogers et al. |
| 5,405,341 A | 4/1995 | Martin |
| 5,407,434 A | 4/1995 | Gross |
| 5,409,463 A | 4/1995 | Thomas et al. |
| 5,409,464 A | 4/1995 | Villalobos |
| 5,409,469 A | 4/1995 | Schaerf |
| 5,409,644 A | 4/1995 | Martin et al. |
| 5,413,561 A | 5/1995 | Fischell et al. |
| 5,415,320 A | 5/1995 | North et al. |
| 5,417,668 A | 5/1995 | Setzer et al. |
| 5,419,340 A | 5/1995 | Stevens |
| 5,423,762 A | 6/1995 | Hillstead |
| 5,429,616 A | 7/1995 | Schaffer |
| 5,431,661 A | 7/1995 | Koch |
| 5,437,645 A | 8/1995 | Urban et al. |
| 5,439,448 A * | 8/1995 | Leschinsky ............ A61M 39/18 |
| | | 604/905 |
| 5,441,504 A | 8/1995 | Pohndorf et al. |
| 5,445,613 A | 8/1995 | Orth |
| 5,453,095 A | 9/1995 | Davila et al. |
| 5,454,409 A | 10/1995 | McAffer et al. |
| 5,460,616 A | 10/1995 | Weinstein et al. |
| 5,472,417 A | 12/1995 | Martin et al. |
| 5,472,418 A | 12/1995 | Palestrant |
| 5,472,432 A | 12/1995 | Martin |
| 5,472,435 A | 12/1995 | Sutton |
| 5,474,099 A | 12/1995 | Boehmer et al. |
| 5,474,540 A | 12/1995 | Miller et al. |
| 5,480,380 A | 1/1996 | Martin |
| 5,484,401 A | 1/1996 | Rodriguez et al. |
| 5,486,159 A | 1/1996 | Mahurkar |
| 5,488,960 A | 2/1996 | Toner |
| 5,496,299 A | 3/1996 | Felix et al. |
| 5,496,346 A | 3/1996 | Horzewski et al. |
| 5,501,676 A | 3/1996 | Niedospial et al. |
| 5,507,733 A | 4/1996 | Larkin et al. |
| 5,509,897 A | 4/1996 | Twardowski et al. |
| 5,509,902 A | 4/1996 | Raulerson |
| 5,514,117 A | 5/1996 | Lynn |
| 5,520,655 A | 5/1996 | Davila et al. |
| 5,520,665 A | 5/1996 | Fleetwood |
| 5,522,806 A | 6/1996 | Schonbachler et al. |
| 5,536,255 A | 7/1996 | Moss |
| 5,538,505 A | 7/1996 | Weinstein et al. |
| 5,542,931 A | 8/1996 | Gravener et al. |
| 5,556,387 A | 9/1996 | Mollenauer et al. |
| 5,569,182 A | 10/1996 | Twardowski et al. |
| 5,599,305 A | 2/1997 | Hermann et al. |
| 5,599,311 A | 2/1997 | Raulerson |
| 5,613,953 A | 3/1997 | Pohndorf |
| 5,613,956 A | 3/1997 | Patterson et al. |
| 5,624,413 A | 4/1997 | Markel et al. |
| 5,632,729 A | 5/1997 | Cai et al. |
| 5,636,875 A | 6/1997 | Wasser |
| 5,637,102 A | 6/1997 | Tolkoff et al. |
| 5,647,857 A | 7/1997 | Anderson et al. |
| 5,651,776 A | 7/1997 | Appling et al. |
| 5,653,698 A | 8/1997 | Niedospial et al. |
| 5,672,158 A | 9/1997 | Okada et al. |
| 5,685,856 A | 11/1997 | Lehrer |
| 5,685,867 A | 11/1997 | Twardowski et al. |
| 5,702,370 A | 12/1997 | Sylvanowicz et al. |
| 5,702,374 A | 12/1997 | Johnson |
| 5,704,915 A | 1/1998 | Melsky et al. |
| 5,713,867 A | 2/1998 | Morris |
| 5,718,678 A | 2/1998 | Fleming, III |
| 5,718,692 A | 2/1998 | Schon et al. |
| 5,725,506 A | 3/1998 | Freeman et al. |
| 5,735,819 A | 4/1998 | Elliott |

(56) References Cited

U.S. PATENT DOCUMENTS

| | | |
|---|---|---|
| 5,741,233 A | 4/1998 | Riddle et al. |
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,628 A | 6/1998 | Bacich et al. |
| 5,772,643 A | 6/1998 | Howell et al. |
| 5,772,678 A | 6/1998 | Thomason et al. |
| 5,776,111 A | 7/1998 | Tesio |
| 5,782,505 A | 7/1998 | Brooks et al. |
| 5,782,807 A | 7/1998 | Falvai et al. |
| 5,782,817 A | 7/1998 | Franzel et al. |
| 5,785,694 A | 7/1998 | Cohen et al. |
| 5,797,869 A | 8/1998 | Martin et al. |
| 5,800,414 A | 9/1998 | Cazal |
| 5,807,311 A | 9/1998 | Palestrant |
| 5,810,789 A | 9/1998 | Powers et al. |
| 5,830,184 A | 11/1998 | Basta |
| 5,843,031 A | 12/1998 | Hermann et al. |
| 5,843,046 A | 12/1998 | Motisi et al. |
| 5,853,393 A | 12/1998 | Bogert |
| 5,858,007 A | 1/1999 | Fagan et al. |
| 5,858,009 A | 1/1999 | Jonkman |
| 5,865,721 A | 2/1999 | Andrews et al. |
| 5,879,333 A | 3/1999 | Smith |
| 5,885,217 A | 3/1999 | Gisselberg et al. |
| 5,895,376 A | 4/1999 | Schwartz et al. |
| 5,897,533 A | 4/1999 | Glickman |
| 5,911,710 A | 6/1999 | Barry et al. |
| 5,916,194 A | 6/1999 | Jacobsen et al. |
| 5,919,160 A | 7/1999 | Sanfilippo, II |
| 5,921,968 A | 7/1999 | Lampropoulos et al. |
| 5,935,112 A | 8/1999 | Stevens et al. |
| 5,944,695 A | 8/1999 | Johnson et al. |
| 5,944,732 A | 8/1999 | Raulerson et al. |
| 5,947,953 A | 9/1999 | Ash et al. |
| 5,951,518 A | 9/1999 | Licata et al. |
| 5,957,912 A | 9/1999 | Heitzmann |
| 5,961,485 A | 10/1999 | Martin |
| 5,961,486 A | 10/1999 | Twardowski et al. |
| 5,967,490 A | 10/1999 | Pike |
| 5,971,958 A | 10/1999 | Zhang |
| 5,976,103 A | 11/1999 | Martin |
| 5,989,206 A | 11/1999 | Prosl et al. |
| 5,989,213 A | 11/1999 | Maginot |
| 5,997,486 A | 12/1999 | Burek et al. |
| 6,001,079 A | 12/1999 | Pourchez |
| 6,024,729 A | 2/2000 | Dehdashtian et al. |
| 6,027,480 A | 2/2000 | Davis et al. |
| 6,033,375 A | 3/2000 | Brumbach |
| 6,033,388 A | 3/2000 | Nordstrom et al. |
| 6,036,171 A | 3/2000 | Weinheimer et al. |
| 6,053,904 A | 4/2000 | Scribner et al. |
| 6,068,011 A | 5/2000 | Paradis |
| 6,074,374 A | 6/2000 | Fulton |
| 6,074,377 A | 6/2000 | Sanfilippo, II |
| 6,074,379 A | 6/2000 | Prichard |
| 6,083,207 A | 7/2000 | Heck |
| 6,086,555 A | 7/2000 | Eliasen et al. |
| 6,086,570 A | 7/2000 | Aboul-Hosn et al. |
| 6,088,889 A | 7/2000 | Luther et al. |
| 6,090,083 A | 7/2000 | Sell et al. |
| 6,093,154 A | 7/2000 | Burek et al. |
| 6,096,011 A | 8/2000 | Trombley, III et al. |
| 6,099,519 A | 8/2000 | Olsen et al. |
| 6,106,503 A | 8/2000 | Pfeiderer et al. |
| 6,106,540 A | 8/2000 | White et al. |
| 6,120,476 A | 9/2000 | Fung et al. |
| 6,120,480 A | 9/2000 | Zhang et al. |
| 6,132,407 A | 10/2000 | Genese et al. |
| 6,142,981 A | 11/2000 | Heck et al. |
| 6,146,371 A | 11/2000 | DeWindt et al. |
| 6,155,610 A | 12/2000 | Godeau et al. |
| 6,156,016 A | 12/2000 | Maginot |
| 6,159,198 A | 12/2000 | Gardeski et al. |
| 6,162,196 A | 12/2000 | Hart et al. |
| 6,171,281 B1 | 1/2001 | Zhang |
| 6,179,806 B1 | 1/2001 | Sansoucy |
| 6,190,349 B1 | 2/2001 | Ash et al. |
| 6,190,352 B1 | 2/2001 | Haarala et al. |
| 6,190,371 B1 | 2/2001 | Maginot et al. |
| 6,206,849 B1 | 3/2001 | Martin et al. |
| 6,210,366 B1 | 4/2001 | Sanfilippo, II |
| 6,213,988 B1 | 4/2001 | McIvor et al. |
| 6,221,057 B1 | 4/2001 | Schwartz et al. |
| 6,228,060 B1 | 5/2001 | Howell |
| 6,228,062 B1 | 5/2001 | Howell et al. |
| 6,240,321 B1 | 5/2001 | Janke et al. |
| 6,258,058 B1 | 7/2001 | Sanfilippo, II |
| 6,273,871 B1 | 8/2001 | Davis et al. |
| 6,276,661 B1 | 8/2001 | Laird |
| 6,293,927 B1 | 9/2001 | McGuckin, Jr. |
| 6,322,541 B2 | 11/2001 | West et al. |
| 6,331,176 B1 | 12/2001 | Becker et al. |
| 6,332,874 B1 | 12/2001 | Eliasen et al. |
| 6,338,725 B1 | 1/2002 | Hermann et al. |
| 6,344,033 B1 | 2/2002 | Jepson et al. |
| 6,352,520 B1 | 3/2002 | Miyazaki |
| 6,375,648 B1 | 4/2002 | Edelman et al. |
| 6,402,723 B1 | 6/2002 | Lampropoulos et al. |
| 6,413,250 B1 | 7/2002 | Smith |
| 6,423,050 B1 | 7/2002 | Twardowski |
| 6,423,053 B1 | 7/2002 | Lee |
| 6,453,185 B1 | 9/2002 | O'Keefe |
| 6,454,744 B1 | 9/2002 | Spohn et al. |
| 6,458,103 B1 | 10/2002 | Albert et al. |
| 6,461,321 B1 | 10/2002 | Quinn |
| 6,475,244 B2 | 11/2002 | Herweck et al. |
| 6,494,860 B2 | 12/2002 | Rocamora et al. |
| 6,497,681 B1 | 12/2002 | Brenner |
| 6,508,790 B1 | 1/2003 | Lawrence |
| 6,508,807 B1 | 1/2003 | Peters |
| 6,517,529 B1 | 2/2003 | Quinn |
| 6,520,939 B2 | 2/2003 | Lafontaine |
| 6,533,763 B1 | 3/2003 | Schneiter |
| 6,544,247 B1 | 4/2003 | Gardeski et al. |
| 6,551,283 B1 | 4/2003 | Guo et al. |
| 6,562,023 B1 | 5/2003 | Marrs et al. |
| 6,565,594 B1 | 5/2003 | Herweck et al. |
| 6,575,960 B2 | 6/2003 | Becker et al. |
| 6,589,262 B1 | 7/2003 | Honebrink et al. |
| 6,592,544 B1 | 7/2003 | Mooney et al. |
| 6,592,558 B2 | 7/2003 | Quah |
| 6,592,565 B2 | 7/2003 | Twardowski |
| 6,623,460 B1 | 9/2003 | Heck |
| 6,626,418 B2 | 9/2003 | Kiehne |
| 6,629,350 B2 | 10/2003 | Motsenbocker |
| 6,632,200 B2 | 10/2003 | Guo et al. |
| 6,638,242 B2 | 10/2003 | Wilson et al. |
| 6,641,574 B2 | 11/2003 | Badia Segura |
| 6,645,178 B1 | 11/2003 | Junker et al. |
| 6,663,595 B2 | 12/2003 | Spohn et al. |
| 6,669,681 B2 | 12/2003 | Jepson et al. |
| 6,682,498 B2 | 1/2004 | Ross |
| 6,682,519 B1 | 1/2004 | Schon |
| 6,689,109 B2 | 2/2004 | Lynn |
| 6,692,464 B2 | 2/2004 | Graf |
| 6,695,832 B2 | 2/2004 | Schon et al. |
| 6,702,776 B2 | 3/2004 | Quinn |
| 6,712,796 B2 | 3/2004 | Fentis et al. |
| 6,719,749 B1 | 4/2004 | Schweikert et al. |
| 6,722,705 B2 | 4/2004 | Korkor |
| 6,749,574 B2 | 6/2004 | O'Keefe |
| 6,752,827 B2 | 6/2004 | Ross et al. |
| 6,827,710 B1 | 12/2004 | Mooney et al. |
| 6,843,513 B2 | 1/2005 | Guala |
| 6,858,019 B2 | 2/2005 | McGuckin, Jr. et al. |
| 6,872,198 B1 | 3/2005 | Wilson et al. |
| 6,881,211 B2 | 4/2005 | Schweikert et al. |
| D505,202 S | 5/2005 | Chesnin |
| 6,887,220 B2 | 5/2005 | Hogendijk |
| 6,893,056 B2 | 5/2005 | Guala |
| 6,916,051 B2 | 7/2005 | Fisher |
| 6,916,313 B2 | 7/2005 | Cunningham |

(56) References Cited

U.S. PATENT DOCUMENTS

| | | |
|---|---|---|
| 6,921,396 B1 | 7/2005 | Wilson et al. |
| 6,932,795 B2 | 8/2005 | Lopez et al. |
| 6,969,381 B2 | 11/2005 | Voorhees |
| 6,971,390 B1 | 12/2005 | Vasek et al. |
| 7,018,384 B2 | 3/2006 | Skakoon |
| 7,044,441 B2 | 5/2006 | Doyle |
| 7,048,724 B2 | 5/2006 | Grossman et al. |
| 7,094,218 B2 | 8/2006 | Rome et al. |
| 7,108,674 B2 | 9/2006 | Quinn |
| 7,128,734 B1 | 10/2006 | Wilson et al. |
| 7,141,035 B2 | 11/2006 | Haggstrom |
| 7,163,531 B2 | 1/2007 | Seese et al. |
| 7,182,746 B2 | 2/2007 | Haarala et al. |
| D542,414 S | 5/2007 | Atkins |
| 7,258,685 B2 | 8/2007 | Kerr |
| 7,276,055 B2 | 10/2007 | DeWindt et al. |
| 7,300,430 B2 | 11/2007 | Wilson et al. |
| 7,347,853 B2 | 3/2008 | DiFiore et al. |
| 7,377,915 B2 | 5/2008 | Rasmussen et al. |
| 7,381,204 B2 | 6/2008 | Wilson et al. |
| 7,390,322 B2 | 6/2008 | McGuckin, Jr. et al. |
| 7,470,261 B2 | 12/2008 | Lynn |
| 7,566,316 B2 | 7/2009 | McGuckin, Jr. et al. |
| 7,569,029 B2 | 8/2009 | Clark |
| 7,578,803 B2 | 8/2009 | Rome et al. |
| 7,594,910 B2 | 9/2009 | Butts et al. |
| 7,594,911 B2 | 9/2009 | Powers et al. |
| 7,628,795 B2 | 12/2009 | Karwoski et al. |
| 7,731,708 B2 | 6/2010 | Haarala et al. |
| 7,740,616 B2 | 6/2010 | Smith et al. |
| 7,749,185 B2 | 7/2010 | Wilson et al. |
| 7,753,868 B2 | 7/2010 | Hoffa |
| 7,776,005 B2 | 8/2010 | Haggstrom et al. |
| 7,806,889 B2 | 10/2010 | Raulerson et al. |
| 7,833,214 B2 | 11/2010 | Wilson et al. |
| 7,854,731 B2 | 12/2010 | Rome et al. |
| 7,875,019 B2 | 1/2011 | Barron et al. |
| 7,883,502 B2 | 2/2011 | Powers et al. |
| 7,914,513 B2 | 3/2011 | Voorhees, Jr. |
| 7,988,658 B2 | 8/2011 | Quinn |
| 8,083,728 B2 | 12/2011 | Rome |
| 8,100,884 B2 | 1/2012 | Schweikert et al. |
| 8,105,313 B2 | 1/2012 | Schweikert et al. |
| 8,137,316 B2 | 3/2012 | Haarala et al. |
| 8,167,867 B2 | 5/2012 | Briscoe et al. |
| 8,177,770 B2 | 5/2012 | Rasmussen et al. |
| 8,177,771 B2 | 5/2012 | Butts et al. |
| 8,206,376 B2 | 6/2012 | Barron et al. |
| 8,251,975 B2 | 8/2012 | Atkins et al. |
| 8,337,484 B2 | 12/2012 | Blanchard |
| 8,361,011 B2 | 1/2013 | Mendels |
| 8,454,565 B2 | 6/2013 | Braga et al. |
| 8,496,607 B2 | 7/2013 | Feng et al. |
| 8,500,674 B2 | 8/2013 | DeFonzo et al. |
| 8,518,013 B2 | 8/2013 | Kurrus et al. |
| 8,603,067 B2 | 12/2013 | Lareau et al. |
| 8,617,138 B2 | 12/2013 | Barron et al. |
| 8,852,168 B2 | 10/2014 | Barron et al. |
| 8,905,998 B2 | 12/2014 | Stephens |
| 9,242,071 B2 | 1/2016 | Morgan et al. |
| 10,272,227 B2 | 4/2019 | Loesener |
| 2001/0020160 A1 | 9/2001 | Esch et al. |
| 2001/0041857 A1 | 11/2001 | Sansoucy |
| 2001/0041873 A1 | 11/2001 | Dopper et al. |
| 2002/0010437 A1 | 1/2002 | Lopez et al. |
| 2002/0077605 A1 | 6/2002 | Fentis et al. |
| 2002/0099326 A1 | 7/2002 | Wilson et al. |
| 2002/0099327 A1 | 7/2002 | Wilson et al. |
| 2002/0128604 A1 | 9/2002 | Nakajima |
| 2002/0147431 A1 | 10/2002 | Lopez et al. |
| 2003/0065288 A1 | 4/2003 | Brimhall et al. |
| 2003/0066218 A1 | 4/2003 | Schweikert |
| 2003/0088213 A1 | 5/2003 | Schweikert et al. |
| 2003/0135197 A1 | 7/2003 | Wang et al. |
| 2003/0153898 A1 | 8/2003 | Schon et al. |
| 2003/0187411 A1 | 10/2003 | Constantz |
| 2003/0199853 A1 | 10/2003 | Olsen et al. |
| 2003/0201639 A1 | 10/2003 | Korkor |
| 2003/0225379 A1 | 12/2003 | Schaffer et al. |
| 2004/0034324 A1* | 2/2004 | Seese ............... A61M 39/105 |
| | | 604/533 |
| 2004/0065333 A1 | 4/2004 | Wilson et al. |
| 2004/0082923 A1 | 4/2004 | Field |
| 2004/0092863 A1 | 5/2004 | Raulerson et al. |
| 2004/0097903 A1 | 5/2004 | Raulerson |
| 2004/0122418 A1 | 6/2004 | Voorhees |
| 2004/0158208 A1 | 8/2004 | Hiejima |
| 2004/0167463 A1 | 8/2004 | Zawacki et al. |
| 2004/0167478 A1 | 8/2004 | Mooney et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0183305 A1 | 9/2004 | Fisher |
| 2004/0186444 A1 | 9/2004 | Daly et al. |
| 2004/0186445 A1 | 9/2004 | Raulerson et al. |
| 2004/0193119 A1 | 9/2004 | Canaud et al. |
| 2004/0210237 A1 | 10/2004 | Ross et al. |
| 2004/0230204 A1 | 11/2004 | Wortley et al. |
| 2004/0243095 A1 | 12/2004 | Nimkar et al. |
| 2005/0027282 A1 | 2/2005 | Schweikert et al. |
| 2005/0049555 A1 | 3/2005 | Moorehead et al. |
| 2005/0080398 A1 | 4/2005 | Markel et al. |
| 2005/0085765 A1 | 4/2005 | Voorhees |
| 2005/0085794 A1 | 4/2005 | Denoth et al. |
| 2005/0095891 A1 | 5/2005 | Schorn |
| 2005/0096585 A1 | 5/2005 | Schon et al. |
| 2005/0113805 A1 | 5/2005 | Devellian et al. |
| 2005/0187535 A1 | 8/2005 | Wilson et al. |
| 2005/0209572 A1 | 9/2005 | Rome et al. |
| 2005/0209581 A1* | 9/2005 | Butts ............... A61M 25/0097 |
| | | 604/523 |
| 2005/0209583 A1 | 9/2005 | Powers et al. |
| 2005/0209584 A1 | 9/2005 | Rome |
| 2005/0228364 A1 | 10/2005 | Braga |
| 2005/0256461 A1* | 11/2005 | DiFiore ............... A61M 39/26 |
| | | 604/537 |
| 2005/0261636 A1 | 11/2005 | Rome et al. |
| 2005/0261664 A1 | 11/2005 | Rome et al. |
| 2005/0261665 A1 | 11/2005 | Voorhees |
| 2006/0009783 A1 | 1/2006 | Rome et al. |
| 2006/0015074 A1 | 1/2006 | Lynn |
| 2006/0015086 A1 | 1/2006 | Rasmussen et al. |
| 2006/0015130 A1 | 1/2006 | Voorhees et al. |
| 2006/0084929 A1 | 4/2006 | Eliasen |
| 2006/0095062 A1 | 5/2006 | Stephens |
| 2006/0100572 A1 | 5/2006 | DiMatteo et al. |
| 2006/0129134 A1 | 6/2006 | Kerr |
| 2006/0276773 A1 | 12/2006 | Wilson et al. |
| 2007/0016167 A1 | 1/2007 | Smith et al. |
| 2007/0049960 A1 | 3/2007 | Stephens et al. |
| 2007/0060866 A1 | 3/2007 | Raulerson et al. |
| 2007/0066964 A1 | 3/2007 | Atkins |
| 2007/0078396 A1 | 4/2007 | Feeley et al. |
| 2007/0078478 A1 | 4/2007 | Atkins et al. |
| 2007/0265597 A1 | 11/2007 | Schweikert et al. |
| 2007/0282274 A1 | 12/2007 | Chesnin |
| 2008/0009832 A1 | 1/2008 | Barron et al. |
| 2008/0032611 A1 | 2/2008 | Dilyard |
| 2008/0097409 A1 | 4/2008 | Stephens |
| 2008/0200901 A1* | 8/2008 | Rasmussen ......... A61M 39/105 |
| | | 604/534 |
| 2008/0214992 A1 | 9/2008 | Haarala et al. |
| 2009/0013944 A1 | 1/2009 | Re Fiorentin et al. |
| 2009/0030426 A1 | 1/2009 | Zinn et al. |
| 2009/0088699 A1 | 4/2009 | King et al. |
| 2009/0137944 A1 | 5/2009 | Haarala et al. |
| 2009/0148591 A1 | 6/2009 | Wang et al. |
| 2009/0187141 A1 | 7/2009 | Lareau et al. |
| 2009/0221950 A1 | 9/2009 | Atkins |
| 2009/0247927 A1 | 10/2009 | Clark |
| 2009/0299377 A1 | 12/2009 | Bright |
| 2010/0010445 A1 | 1/2010 | Powers et al. |
| 2010/0016838 A1 | 1/2010 | Butts et al. |
| 2010/0063512 A1 | 3/2010 | Braga et al. |

(56) References Cited

U.S. PATENT DOCUMENTS

| | | | |
|---|---|---|---|
| 2010/0063513 | A1 | 3/2010 | Braga et al. |
| 2010/0069950 | A1 | 3/2010 | Rabbitte et al. |
| 2010/0168642 | A1 | 7/2010 | Appling et al. |
| 2010/0174183 | A1 | 7/2010 | Schwartz et al. |
| 2010/0174291 | A1 | 7/2010 | Atkins et al. |
| 2010/0331823 | A1 | 12/2010 | Blanchard |
| 2011/0098653 | A1 | 4/2011 | Powers et al. |
| 2011/0098679 | A1 | 4/2011 | Barron et al. |
| 2011/0213291 | A1 | 9/2011 | Quinn |
| 2012/0016285 | A1 | 1/2012 | Contractor |
| 2012/0083766 | A1 | 4/2012 | Haarala et al. |
| 2012/0148175 | A1 | 6/2012 | Wesselmann |
| 2012/0209221 | A1 | 8/2012 | Patterson et al. |
| 2012/0253322 | A1* | 10/2012 | Barron .............. A61M 39/105 604/535 |
| 2013/0245568 | A1 | 9/2013 | Kerr |
| 2014/0107614 | A1 | 4/2014 | Barron et al. |
| 2014/0155801 | A1 | 6/2014 | Zinn et al. |
| 2014/0358120 | A1 | 12/2014 | Haarala et al. |
| 2015/0051536 | A1 | 2/2015 | Mendels et al. |
| 2015/0320927 | A1 | 11/2015 | Nardeo |
| 2016/0067472 | A1 | 3/2016 | Haarala et al. |
| 2016/0129222 | A1* | 5/2016 | Loesener .......... A61M 25/0097 604/537 |
| 2017/0043126 | A1 | 2/2017 | Jones et al. |
| 2018/0318553 | A1* | 11/2018 | Scandone, Jr. ... A61M 25/0194 |
| 2019/0247616 | A1 | 8/2019 | Loesener |

FOREIGN PATENT DOCUMENTS

| | | |
|---|---|---|
| EP | 0616817 A1 | 9/1994 |
| EP | 1240916 A1 | 9/2002 |
| GB | 1503469 A | 3/1978 |
| WO | 1984001902 A1 | 5/1984 |
| WO | 1994021315 A1 | 9/1994 |
| WO | 1996034645 A1 | 11/1996 |
| WO | 1997022374 A1 | 6/1997 |
| WO | 2000023137 A1 | 4/2000 |
| WO | 01/97743 A2 | 12/2001 |
| WO | 2002058776 A2 | 8/2002 |
| WO | 2003030960 A2 | 4/2003 |
| WO | 2003033049 A2 | 4/2003 |
| WO | 2006004943 A2 | 1/2006 |
| WO | 2006066023 A2 | 6/2006 |
| WO | 2006130133 A1 | 12/2006 |
| WO | 2009015016 A1 | 1/2009 |
| WO | 2016/073954 A1 | 5/2016 |

OTHER PUBLICATIONS

Camp, "Care of the Groshong Catheter", Oncol Nurs Forum, vol. 15, No. 6, 1988.
Delmore et al., "Experience with the Groshong Long-Term Central Venous Catheter", Gynecologic Oncology 34, 216-218 (1989).
EP 15856731.3 filed Jun. 6, 2017 Extended European Search Report dated May 25, 2018.
Goldfarb et al., "Chronic Venous Access Bedside Placement Technique and Complications," Cancer Practice vol. 2, No. 4, pp. 279-283 (Jul./Aug. 1994).
Health Devices, "Hazard Report," vol. 25, Nos. 5-6, pp. 214-215, May-Jun. 1996.
Hull et al., "The Groshong Catheter: Initial Experience and Early Results of Imging-guided Placement," Cardiovascular Radiology 185:803-807 (1992).
Malviya et al., "Vascular Access in Gynecological Cancer Using the Groshong Right Atrial Catheter", Gynecological Oncology 33, 313-316 (1989).
PCT/US2005/009150 filed Mar. 18, 2005 Preliminary Report on Patentability dated May 26, 2006.
PCT/US2005/009150 filed Mar. 18, 2005 Search Report dated Jun. 7, 2005.
PCT/US2005/009150 filed Mar. 18, 2005 Written Opinion dated Jun. 17, 2005.
PCT/US2010/040084 filed Jun. 25, 2010 Search Report dated Sep. 27, 2010.
PCT/US2010/040084 filed Jun. 25, 2010 Written Opinion dated Sep. 27, 2010.
PCT/US2015/059620 filed Nov. 6, 2015 International Search Report and Written Opinion dated Jan. 28, 2016.
PCT/US2018/047831 filed Aug. 23, 2018 International Search Report and Written Opinion dated Feb. 5, 2019.
Salem et al., "A New Peripherally Implanted Subcutaneous Permanent Central Venous Access Device for Patients Requiring Chemotherapy," Journal of Clinical Oncology, vol. 11, No. 11, p. 2181-2185 (Nov. 1993).
Twardowski et al., "Measuring Central Venous Structures in Humans: Implications for Central-Vein Catheter Dimensions," The Journal of Vascular Access 3:21-37 (2002).
U.S. Appl. No. 10/803,207, filed Mar. 18, 2004 Non-Final Office Action dated Sep. 19, 2005.
U.S. Appl. No. 10/803,207, filed Mar. 18, 2004 Notice of Allowance dated Apr. 21, 2006.
U.S. Appl. No. 10/803,279, filed Mar. 18, 2004 Advisory Action dated Aug. 22, 2007.
U.S. Appl. No. 10/803,279, filed Mar. 18, 2004 Final Office Action dated May 31, 2007.
U.S. Appl. No. 10/803,279, filed Mar. 18, 2004 Final Office Action dated Oct. 1, 2008.
U.S. Appl. No. 10/803,279, filed Mar. 18, 2004 Non-Final Office Action dated Apr. 2, 2009.
U.S. Appl. No. 10/803,279, filed Mar. 18, 2004 Non-Final Office Action dated Jun. 5, 2006.
U.S. Appl. No. 10/803,279 filed Mar. 18, 2004 Non-Final Office Action dated Sep. 20, 2007.
U.S. Appl. No. 10/803,279, filed Mar. 18, 2004 Non-Final Office Action dated Dec. 1, 2006.
U.S. Appl. No. 10/803,279, filed Mar. 18, 2004 Notice of Allowance dated May 28, 2009.
U.S. Appl. No. 10/803,512, filed Mar. 18, 2004 Advisory Action dated Oct. 16, 2008.
U.S. Appl. No. 10/803,512, filed Mar. 18, 2004 Final Office Action dated May 30, 2008.
U.S. Appl. No. 10/803,512, filed Mar. 18, 2004 Non-Final Office Action dated Jan. 24, 2008.
U.S. Appl. No. 10/803,512, filed Mar. 18, 2004 Non-Final Office Action dated May 24, 2010.
U.S. Appl. No. 10/803,512, filed Mar. 18, 2004 Non-Final Office Action dated Jul. 22, 2009.
U.S. Appl. No. 10/803,512, filed Mar. 18, 2004 Final Office Action dated Sep. 28, 2010.
U.S. Appl. No. 10/803,513, filed Mar. 18, 2004 Non-Final Office Action dated Jul. 25, 2008.
U.S. Appl. No. 10/803,513, filed Mar. 18, 2004 Notice of Allowance dated Jun. 12, 2009.
U.S. Appl. No. 11/076,564, filed Mar. 8, 2005 Advisory Action dated Nov. 16, 2006.
U.S. Appl. No. 11/076,564, filed Mar. 8, 2005 Final Office Action dated Jul. 27, 2007.
U.S. Appl. No. 11/076,564, filed Mar. 8, 2005 Final Office Action dated Aug. 25, 2006.
U.S. Appl. No. 11/076,564, filed Mar. 8, 2005 Non-Final Office Action dated Jan. 23, 2008.
U.S. Appl. No. 11/076,564, filed Mar. 8, 2005 Non-Final Office Action dated Feb. 9, 2007.
U.S. Appl. No. 11/076,564, filed Mar. 8, 2005 Non-Final Office Action dated Mar. 9, 2006.
U.S. Appl. No. 11/076,564, filed Mar. 8, 2005 Non-Final Office Action dated Dec. 17, 2008.
U.S. Appl. No. 11/076,564, filed Mar. 8, 2005 Notice of Allowance dated Jun. 17, 2009.
U.S. Appl. No. 11/096,553, filed Apr. 1, 2005 Advisory Action dated Aug. 1, 2007.
U.S. Appl. No. 11/096,553, filed Apr. 1, 2005 Final Office Action dated Feb. 27, 2007.

(56) References Cited

OTHER PUBLICATIONS

U.S. Appl. No. 11/096,553, filed Apr. 1, 2005 Non-Final Office Action dated Jan. 24, 2006.
U.S. Appl. No. 11/096,553, filed Apr. 1, 2005 Non-Final Office Action dated May 19, 2006.
U.S. Appl. No. 11/096,553, filed Apr. 1, 2005 Non-Final Office Action dated Oct. 10, 2007.
U.S. Appl. No. 11/096,553, filed Apr. 1, 2005 Notice of Allowance dated Mar. 25, 2008.
U.S. Appl. No. 11/122,303, filed May 3, 2005 Advisory Action dated Jul. 14, 2008.
U.S. Appl. No. 11/122,303, filed May 3, 2005 Final Office Action dated Apr. 30, 2008.
U.S. Appl. No. 11/122,303, filed May 3, 2005 Non-Final Office Action dated Jan. 20, 2010.
U.S. Appl. No. 11/122,303, filed May 3, 2005 Non-Final Office Action dated Jun. 8, 2009.
U.S. Appl. No. 11/122,303, filed May 3, 2005 Non-Final Office Action dated Sep. 13, 2007.
U.S. Appl. No. 11/122,303, filed May 3, 2005 Notice of Allowance dated Jul. 9, 2010.
U.S. Appl. No. 11/122,303, filed May 3, 2005 Notice of Allowance dated Sep. 2, 2010.
U.S. Appl. No. 11/471,193, filed Jun. 20, 2006 Non-Final Office Action dated Jan. 14, 2010.
U.S. Appl. No. 11/471,193, filed Jun. 20, 2006 Notice of Allowance dated Jul. 26, 2010.
U.S. Appl. No. 12/106,704, filed Apr. 21, 2008 Final Office Action dated Apr. 15, 2010.
U.S. Appl. No. 12/106,704, filed Apr. 21, 2008 Non-Final Office Action dated Apr. 27, 2009.
U.S. Appl. No. 12/106,704, filed Apr. 21, 2008 Non-Final Office Action dated Oct. 22, 2009.
U.S. Appl. No. 12/563,776, filed Sep. 21, 2009 Non-Final Office Action dated Jun. 16, 2010.
U.S. Appl. No. 12/563,776, filed Sep. 12, 2009 Notice of Allowance dated Nov. 12, 2010.
U.S. Appl. No. 12/563,996, filed Sep. 21, 2009 Final Office Action dated Dec. 1, 2011.
U.S. Appl. No. 12/563,996, filed Sep. 21, 2009 Non-Final Office Action dated Jun. 13, 2011.
U.S. Appl. No. 12/823,663, filed Jun. 25, 2010 Final Office Action dated Jun. 15, 2012.
U.S. Appl. No. 12/823,663, filed Jun. 25, 2010 Non-Final Office Action dated Jan. 6, 2012.
U.S. Appl. No. 12/823,663, filed Jun. 25, 2010 Notice of Allowance dated Aug. 30, 2012.
U.S. Appl. No. 12/974,818, filed Dec. 21, 2010 Non-Final Office Action dated Nov. 16, 2011.
U.S. Appl. No. 12/982,389, filed Dec. 30, 2010 Ex Parte Quayle Action dated Apr. 12, 2013.
U.S. Appl. No. 12/982,389, filed Dec. 30, 2010 Notice of Allowance dated May 1, 2013.
U.S. Appl. No. 13/524,884, filed Jun. 15, 2012 Non-Final Office Action dated Jun. 5, 2013.
U.S. Appl. No. 13/524,884, filed Jun. 15, 2012 Notice of Allowance dated Sep. 6, 2013.
U.S. Appl. No. 14/141,209, filed Dec. 26, 2013 Non-Final Office Action dated Apr. 4, 2014.
U.S. Appl. No. 14/141,209, filed Dec. 26, 2013 Notice of Allowance dated Jun. 24, 2014.
U.S. Appl. No. 14/935,364, filed Nov. 6, 2015 Advisory Action dated Aug. 7, 2017.
U.S. Appl. No. 14/935,364, filed Nov. 6, 2015 Final Office Action dated Jul. 17, 2018.
U.S. Appl. No. 14/935,364, filed Nov. 6, 2015 Final Office Action dated Jun. 6, 2017.
U.S. Appl. No. 14/935,364, filed Nov. 6, 2015 Non-Final Office Action dated Dec. 26, 2017.
U.S. Appl. No. 14/935,364, filed Nov. 6, 2015 Non-Final Office Action dated Nov. 4, 2016.
U.S. Appl. No. 14/935,364, filed Nov. 6, 2015 Notice of Allowance dated Dec. 28, 2018.
U.S. Appl. No. 14/935,364, filed Nov. 6, 2015 Panel Decision dated Oct. 6, 2017.
Vesely, "Central Venous Catheter Tip Position: A Continuing Controversy," JVIR vol. 14, No. 5, pp. 527-534 (May 2003).
U.S. Appl. No. 16/394,813, filed Apr. 25, 2019 Non-Final Office Action dated Dec. 20, 2021.

* cited by examiner

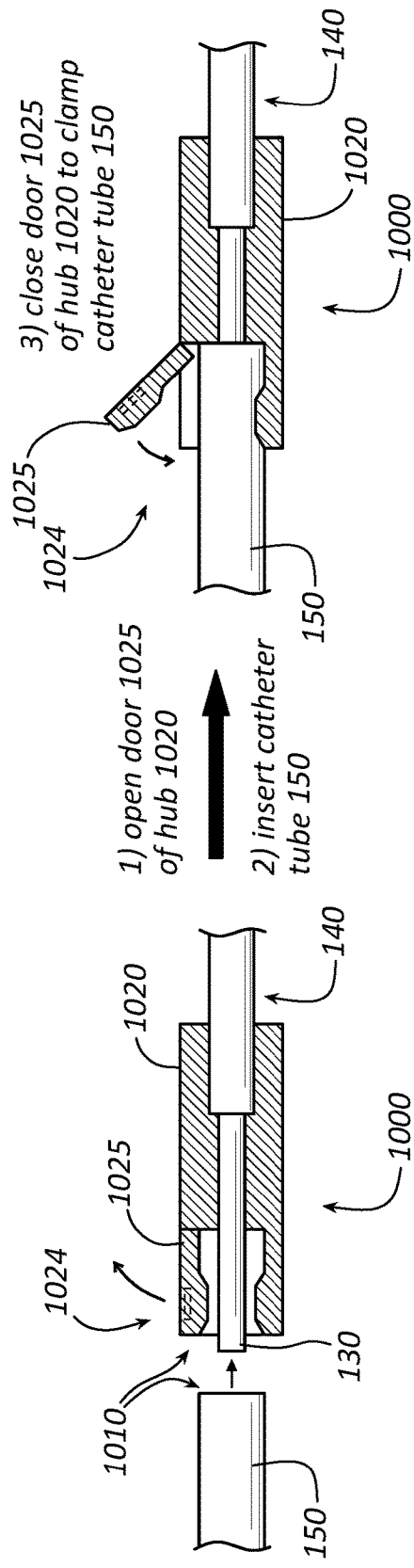
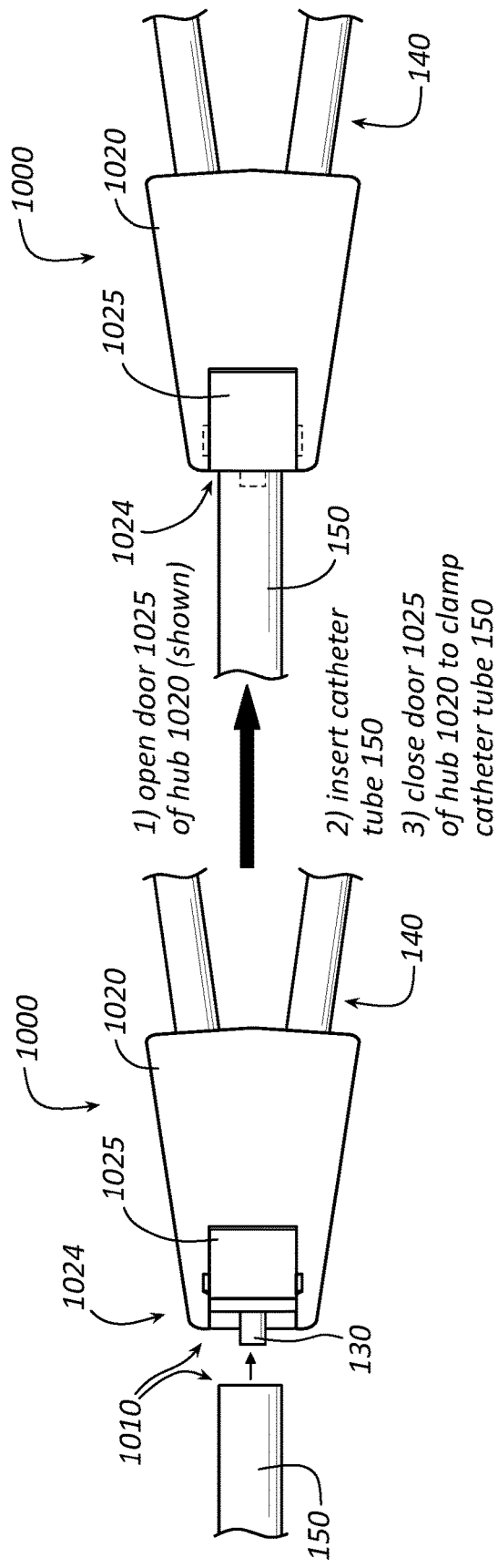
FIG. 10A
FIG. 10B

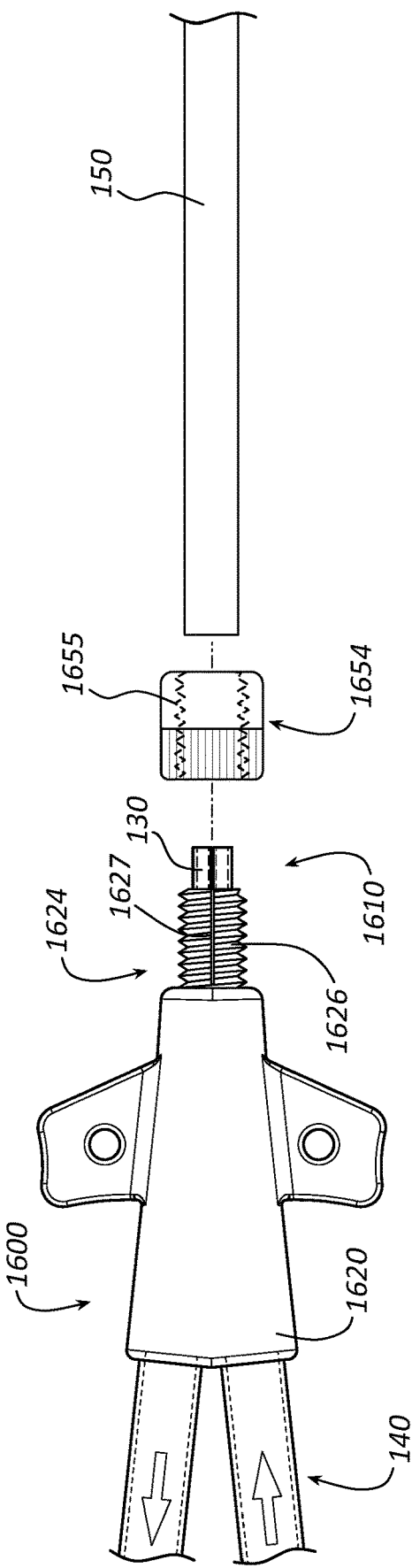
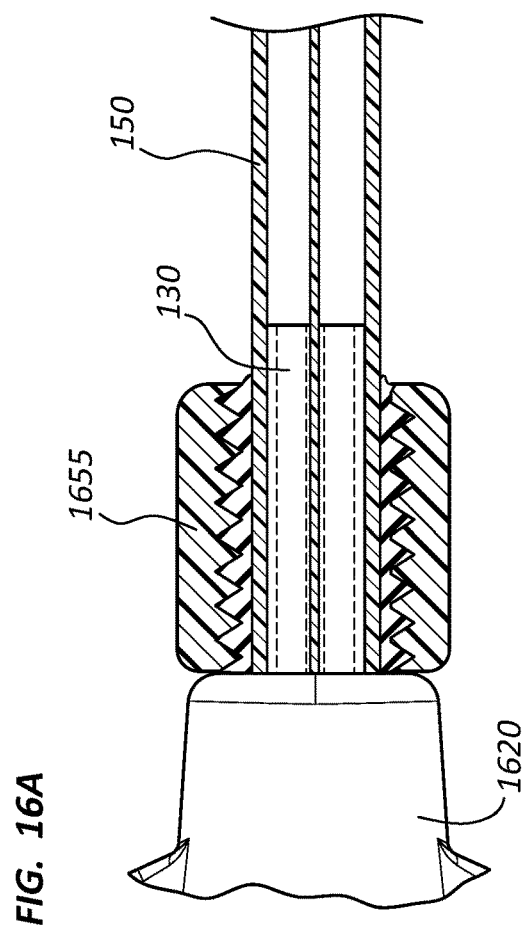
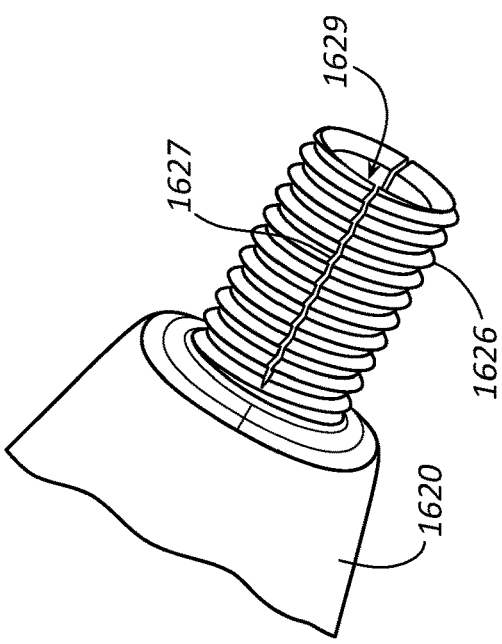
FIG. 16A
FIG. 16C
FIG. 16B

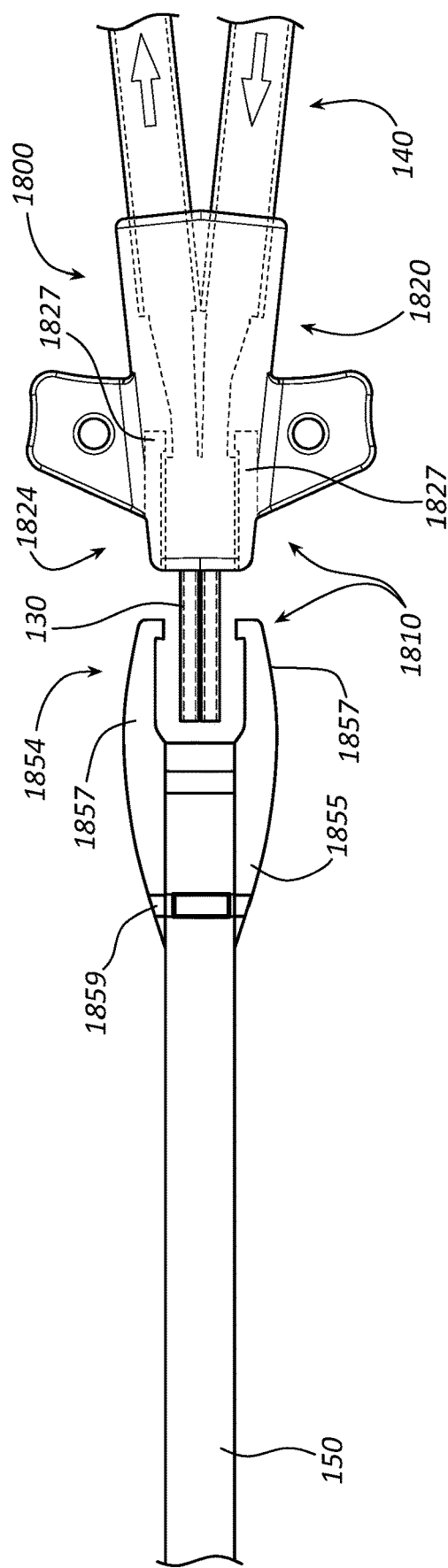
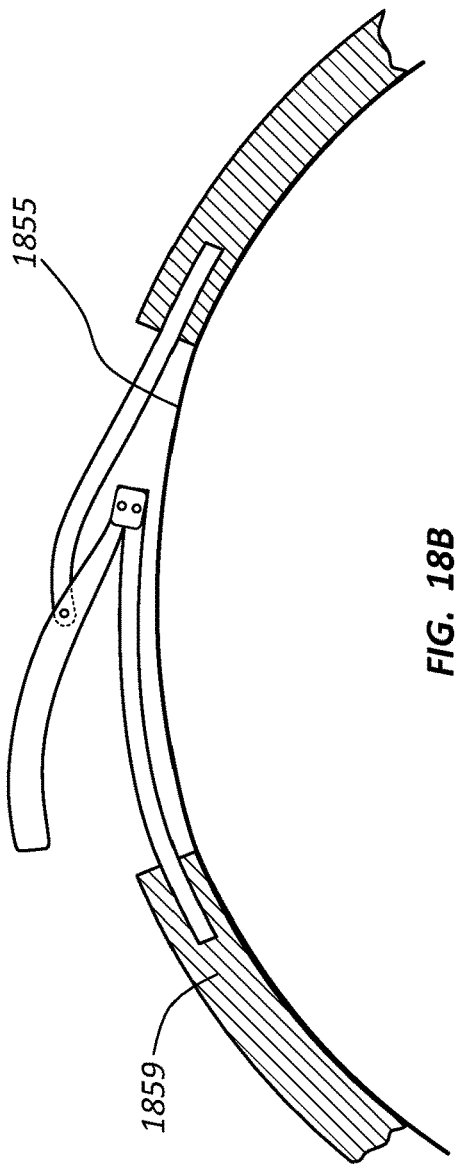
FIG. 18A
FIG. 18B

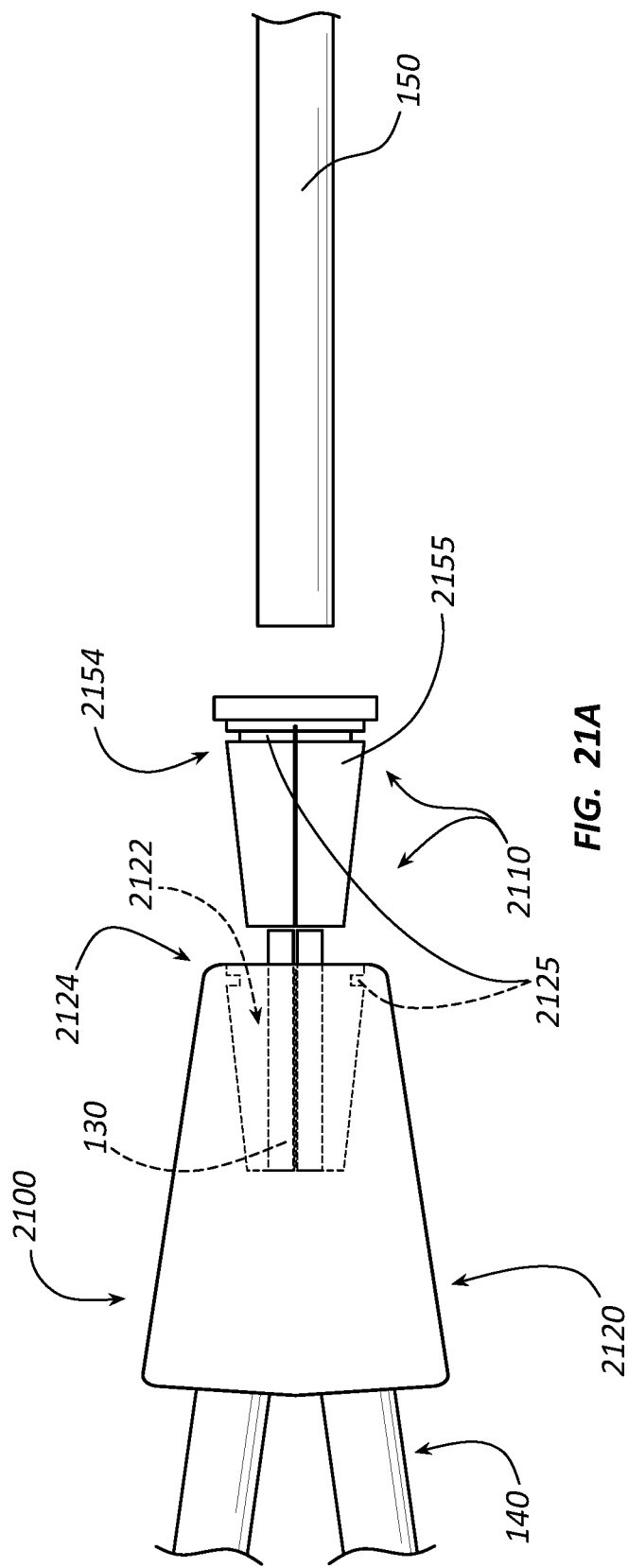
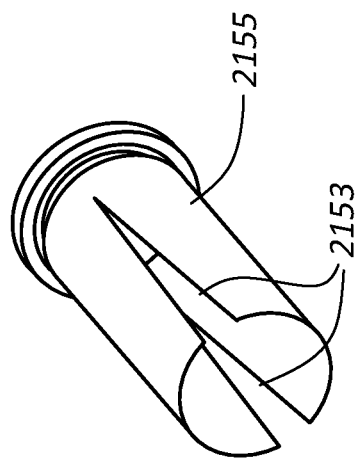
FIG. 21A
FIG. 21B

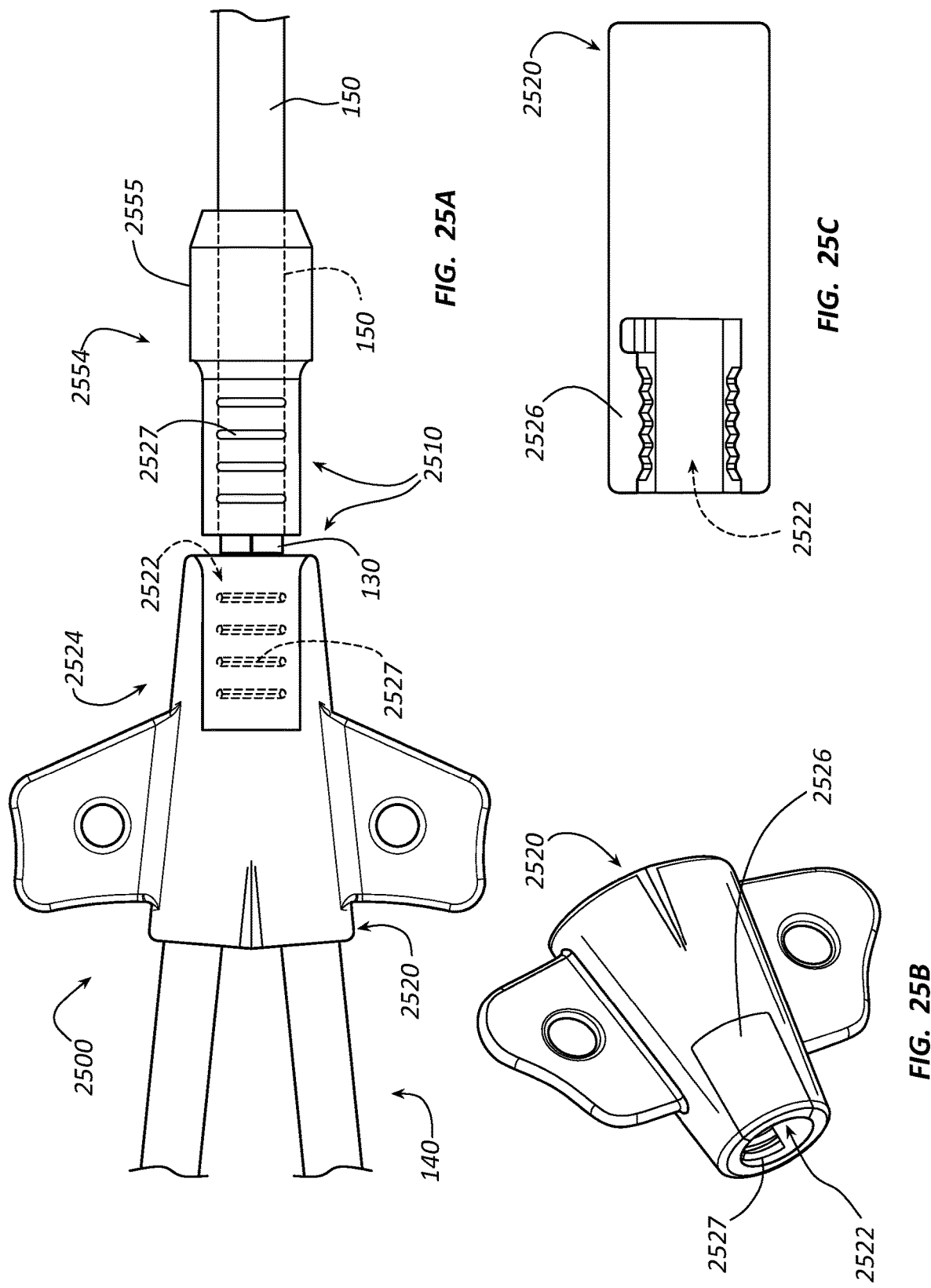

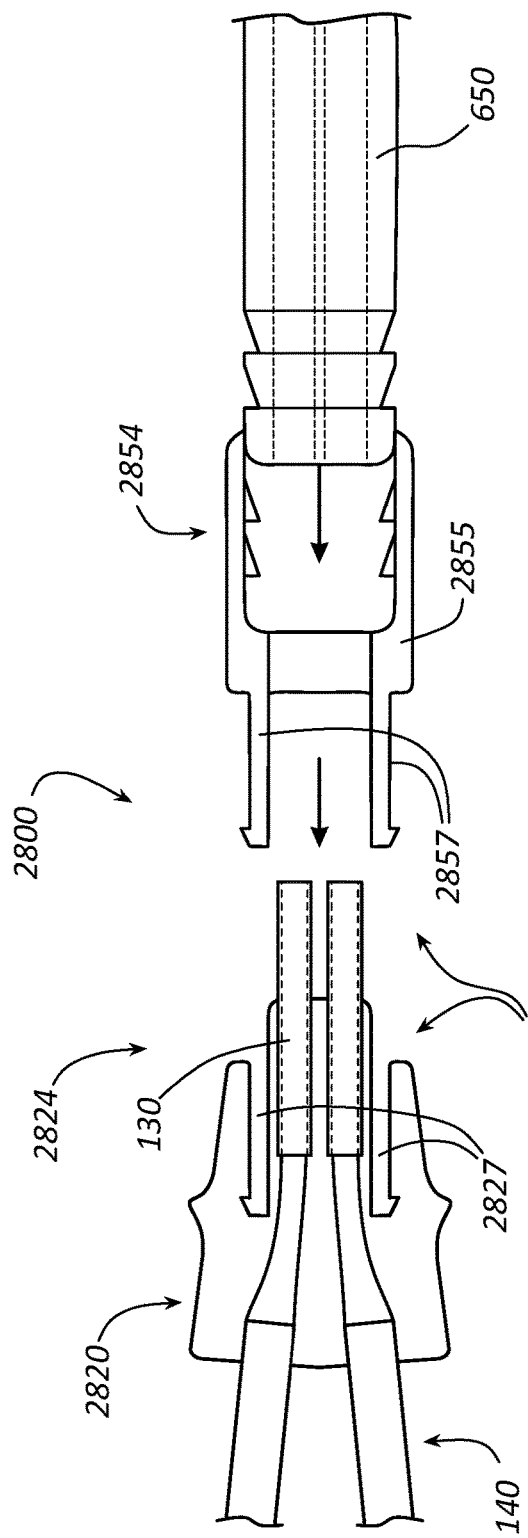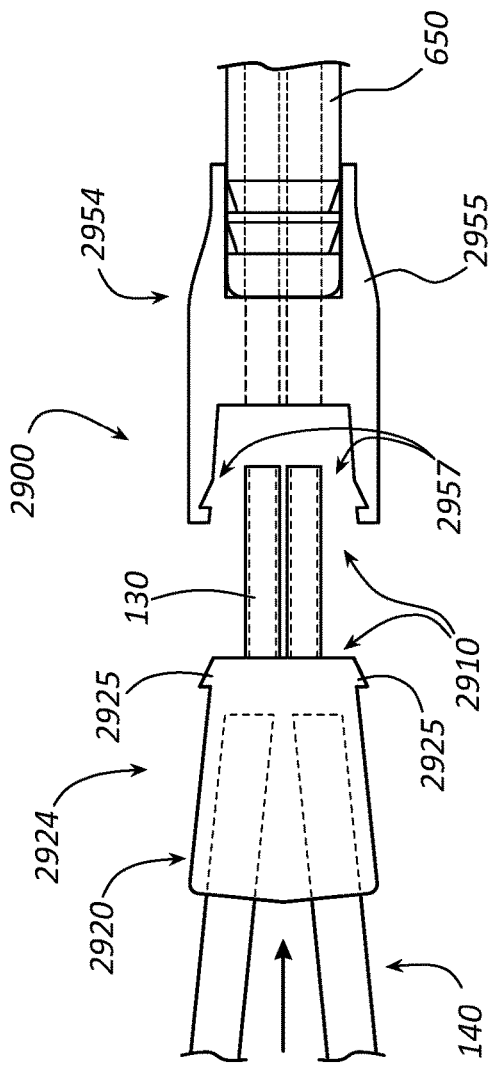

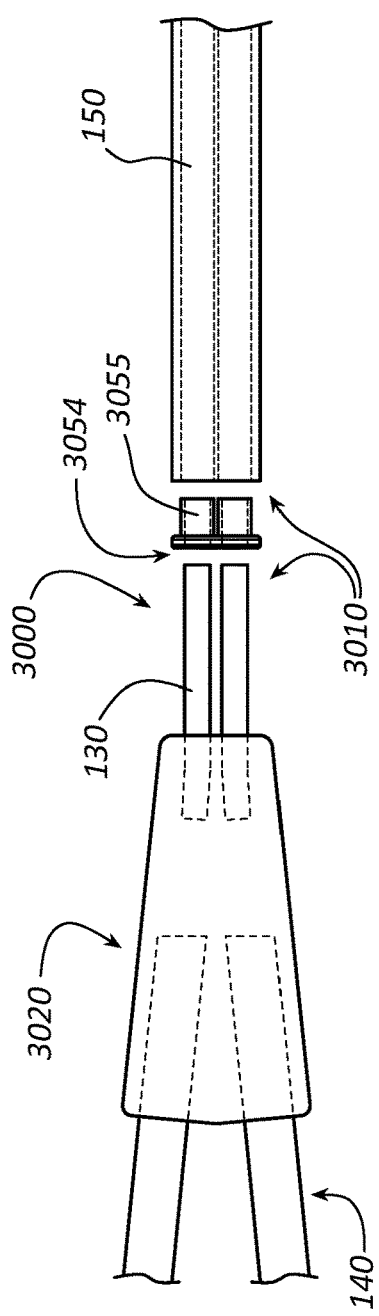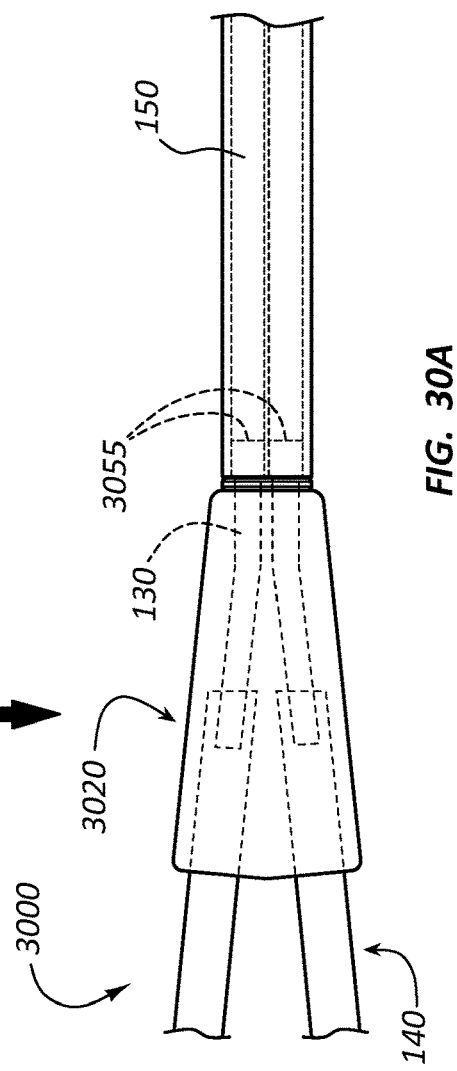
FIG. 30A
FIG. 30B

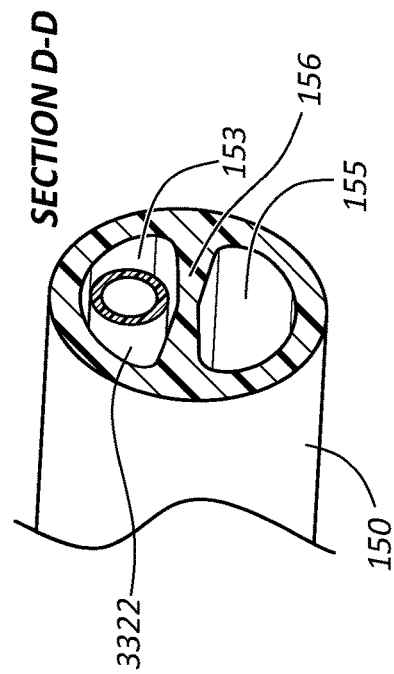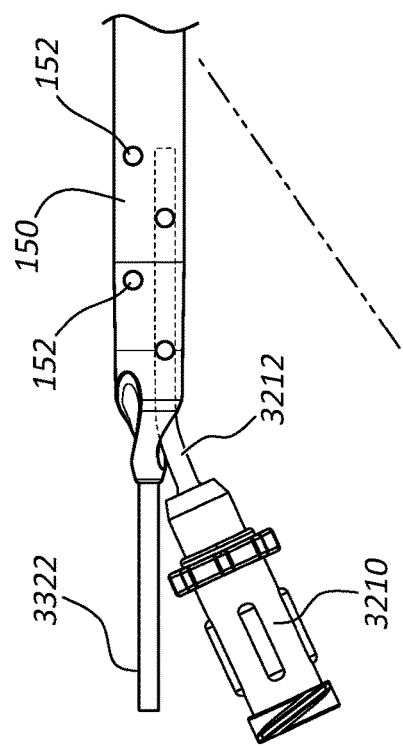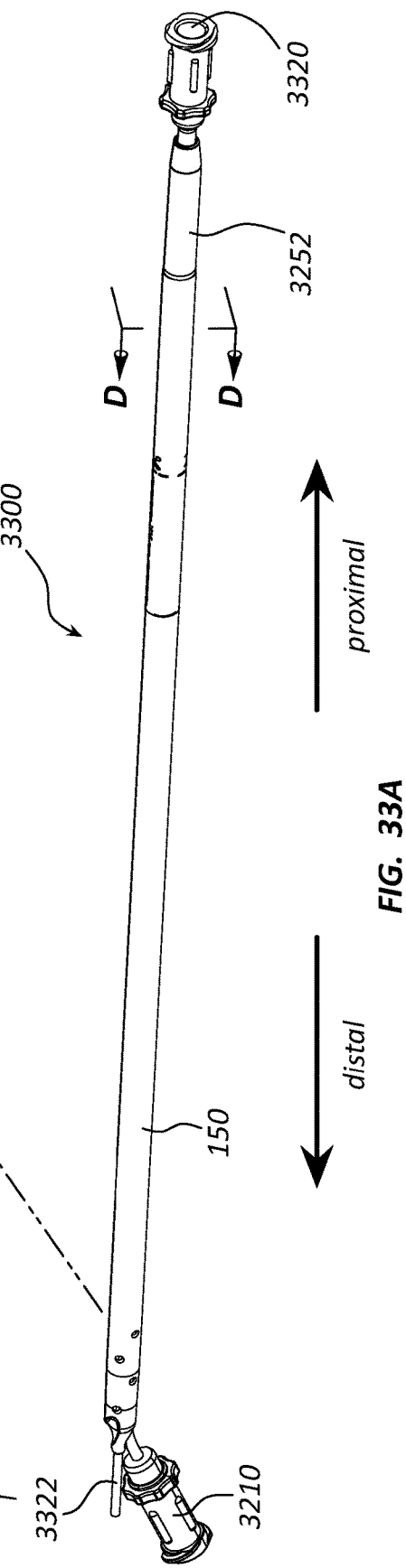

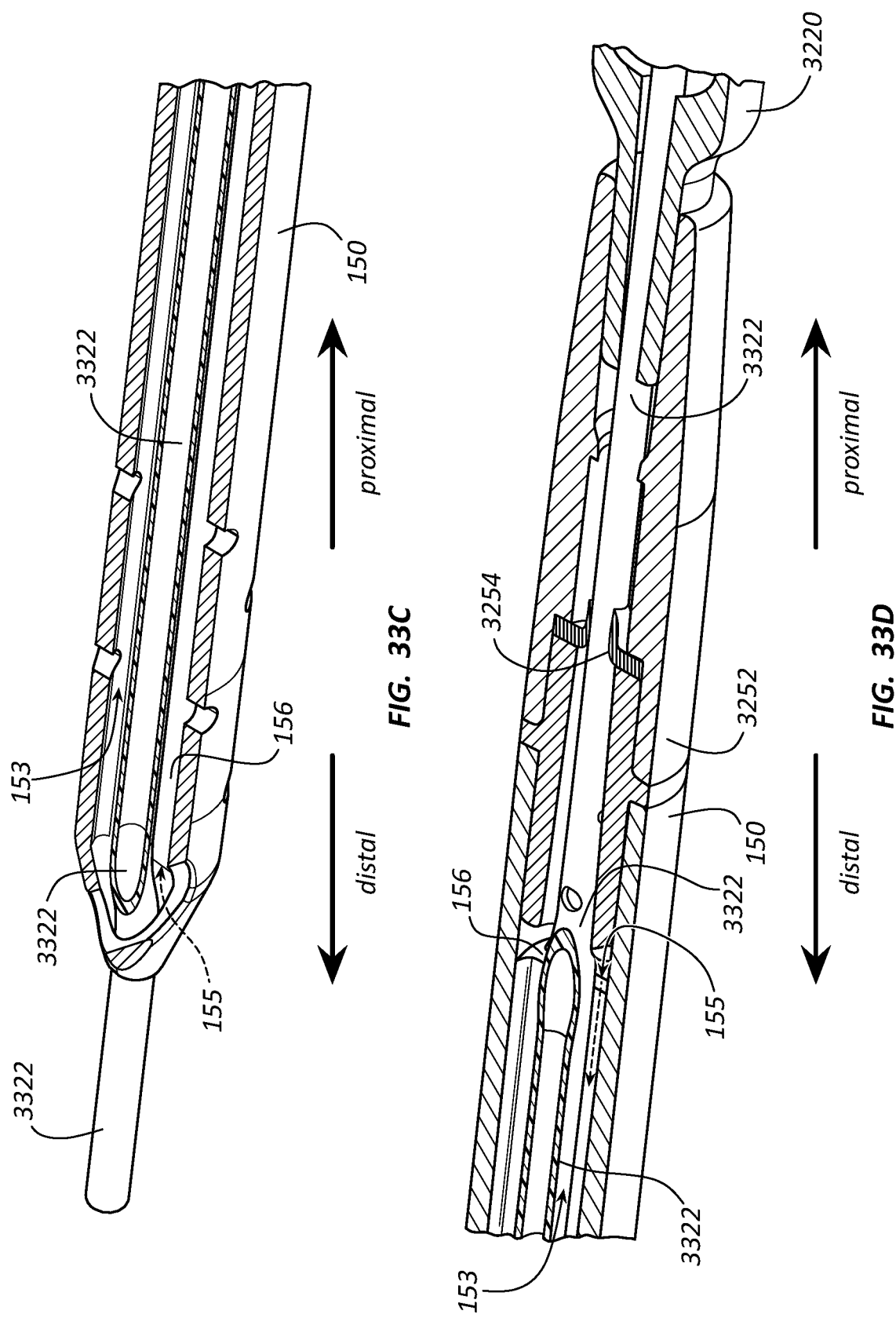

PRIMING AND TUNNELING SYSTEM FOR A RETROGRADE CATHETER ASSEMBLY

PRIORITY

This application is a U.S. national stage from International Application No. PCT/US2018/047831, which claims the benefit of priority to the following: 1) U.S. Provisional Application No. 62/549,354, filed Aug. 23, 2017, and titled, "Priming and Tunneling System for a Retrograde Catheter Assembly;" 2) U.S. Provisional Application No. 62/549,359, filed Aug. 23, 2017, and titled, "Connection System for a Proximally Trimmable Catheter Assembly;" and 3) U.S. Provisional Application No. 62/631,471, filed Feb. 15, 2018, and also titled, "Connection System for a Proximally Trimmable Catheter Assembly," each of which applications is incorporated by reference in its entirety into this application.

BACKGROUND

When placing a catheter assembly such as a hemodialysis catheter in a patient by way of a retrograde tunneling technique, a clinician primes a catheter tube of the catheter to safeguard against air embolism, places a distal end of the catheter tube in a vessel of the patient, and cuts off a proximal end portion of the catheter tube to customize a length of the catheter tube according to the patient's anatomy. Afterward, a freshly cut proximal end of the catheter tube is tunneled under the patient's skin in a retrograde fashion to a location on the patient's chest where the catheter tube is connected to a remainder of the catheter assembly. When the catheter tube is connected to a remainder of the catheter assembly such as a hub and any extension tubes connected thereto, the catheter tube should be attached to the remainder of the catheter assembly in a simple, secure, and leakproof manner.

Disclosed herein are catheter assemblies and methods thereof that address various aspects of at least the retrograde tunneling technique. The catheter assemblies include, but are not limited to, catheter assemblies configured for vascular access, catheter assemblies configured for priming, catheter assemblies configured for tunneling, and mechanisms for connecting catheter tubes to their respective catheter assemblies. The methods include, but are not limited to, priming, tunneling, and connecting catheter tubes to their respective catheter assemblies.

SUMMARY

Disclosed herein is catheter assembly including, in some embodiments, a proximal portion of the catheter assembly, a distal portion of the catheter assembly, and a connection mechanism configured to connect the proximal portion of the catheter assembly to the distal portion of the catheter assembly. The proximal portion of the catheter assembly includes a bifurcated hub, a pair of polymer-coated cannulas partially disposed in and extending from the bifurcated hub, and a pair of extension tubes disposed in and extending from the bifurcated hub. The pair of cannulas and the pair of extension tubes form a proximal pair of lumens extending through the proximal portion of the catheter assembly. The distal portion of the catheter assembly includes a catheter tube having a distal pair of lumens extending through the distal portion of the catheter assembly. The catheter tube is configured to fit over the pair of cannulas to extend the proximal and distal pairs of lumens through an entirety of the catheter assembly as an extended pair of lumens. The connection mechanism is further configured to connect the catheter tube to the pair of cannulas, thereby providing a fluid-tight connection between the catheter tube and the pair of cannulas.

In some embodiments, the polymer of the polymer-coated cannulas is polyurethane.

In some embodiments, the extended pair of lumens includes an arterial lumen and a venous lumen. At least an arterial cannula of the pair of cannulas and an arterial extension tube of the pair of extension tubes form a proximal portion of the arterial lumen. At least a venous cannula of the pair of cannulas and a venous extension tube of the pair of extension tubes form a proximal portion of the venous lumen.

In some embodiments, a distal portion of the arterial lumen and a distal portion of the venous lumen form the distal pair of lumens extending through the distal portion of the catheter assembly.

In some embodiments, the bifurcated hub includes an inner hub and an outer hub. The inner hub is molded over the pair of cannulas. The outer hub is molded over the pair of extension tubes and the inner hub. The inner hub has a higher durometer than the outer hub.

In some embodiments, the connection mechanism is a collarless connection mechanism or a collared connection mechanism including a collar configured to fit over a proximal end portion of the catheter tube.

In some embodiments, the connection mechanism is a collarless connection mechanism including a hub-based securement feature selected from one or more circumferential protrusions, a number of radial protrusions, and a combination thereof. The circumferential protrusions include rings or barbs, and the number of radial protrusions include pillars, spikes, or barbs.

In some embodiments, the connection mechanism is a collarless connection mechanism including a hub-based securement feature configured to interlock with a catheter tube-based securement feature. The hub-based securement features includes at least a lip at a distal end of a socket, and the catheter tube-based securement feature includes at least a circumferential barb configured to interlock with the lip of the socket.

In some embodiments, the connection mechanism is a collarless connection mechanism including a hub-based securement feature configured as a clamping-style hub for clamping the catheter tube on the pair of cannulas.

In some embodiments, the connection mechanism is a collared connection mechanism including a hub-based securement feature configured to interlock with a catheter tube-based securement feature. The hub-based securement feature includes a circumferential groove, and the catheter tube-based securement feature includes an over-the-hub interlocking collar.

In some embodiments, the connection mechanism is a collared connection mechanism including a hub-based securement feature configured to interlock with a catheter tube-based securement feature. One securement feature of the hub-based securement feature and the catheter tube-based securement feature includes interlocking arms and another securement feature of the hub-based securement feature and the catheter tube-based securement feature includes receiving slots for the interlocking arms.

In some embodiments, the connection mechanism is a collared connection mechanism including a hub-based securement feature configured to interlock with a catheter tube-based securement feature. The hub-based securement feature includes a receiver, and the catheter tube-based securement feature includes a collet proper configured for disposal in the receiver.

In some embodiments, the connection mechanism is a collared connection mechanism including a hub-based securement feature configured to interlock with a catheter tube-based securement feature. The hub-based securement feature includes a collet proper, and the catheter tube-based securement feature includes a collet cap and integrated receiver configured to accept the collet proper.

Also disclosed herein is catheter assembly including, in some embodiments, a catheter tube, a flow-directing cap, and a priming adapter. The catheter tube includes a pair of lumens extending from a distal end portion to a proximal end portion of the catheter tube. The flow-directing cap is about the proximal end portion of the catheter tube. The flow-directing cap includes a valve at a proximal end of the catheter tube. The priming adapter includes a priming stylet configured for priming both an arterial lumen and a venous lumen of the pair of lumens when the priming stylet is inserted into either the arterial lumen or the venous lumen.

In some embodiments, the catheter assembly further includes an over-the-wire ("OTW") adapter including an OTW stylet. The OTW adapter and the OTW stylet are configured for advancing the catheter tube in a patient over a guidewire in the OTW stylet when the OTW stylet is inserted into either the arterial lumen or the venous lumen of the pair of lumens. The OTW stylet includes a plurality of openings in an end portion of the OTW stylet coupled to the OTW adapter.

In some embodiments, the valve at the proximal end of the catheter tube is configured to remain closed when the OTW stylet is not inserted into either the arterial lumen or the venous lumen of the pair of lumens. This enables priming both the arterial lumen and the venous lumen from the distal end portion of the catheter tube when the priming stylet is inserted into either the arterial lumen or the venous lumen.

In some embodiments, the valve at the proximal end of the catheter tube is configured to open when the OTW stylet is inserted through the valve and into either the arterial lumen or the venous lumen of the pair of lumens. The openings in the end portion of the OTW stylet enables priming each of the arterial lumen, the venous lumen, and a stylet lumen when the priming stylet is inserted into either the arterial lumen or the venous lumen at the distal end portion of the catheter tube.

In some embodiments, the catheter tube is configured to be cut to length at a location on the catheter tube distal to the flow-directing cap for attaching the catheter tube to a pair of cannulas.

Also disclosed herein is catheter-tube tunneling assembly including, in some embodiments, a tunneling shaft, an ambidextrous handle, and a lock collar. The ambidextrous handle includes a hub disposed in and extending from a distal end portion of the handle. The hub is configured for insertion of a first end portion or a second end portion of the tunneling shaft into a socket of the hub. The lock collar is configured to slide over the tunneling shaft and interlock with the hub to lock the tunneling shaft on the handle.

In some embodiments, the first end portion and the second portion of the tunneling shaft are configured for insertion into a flow-directing cap about a proximal end portion of a catheter tube.

In some embodiments, the first end portion and the second portion of the tunneling shaft are each configured with a circumferential or wedge-shaped barb configured to interlock with a complementary feature in the flow-directing cap about a proximal end portion of a catheter tube.

In some embodiments, the first end portion and the second portion of the tunneling shaft are each configured with a circumferential or wedge-shaped barb configured to interlock with a complementary feature in the socket of the hub and restrict axial rotation of the tunneling shaft relative to the handle.

In some embodiments, the first end portion and the second portion of the tunneling shaft are each configured with a circumferential or wedge-shaped barb configured for subcutaneously tunneling the tunneling shaft in a patient.

Also disclosed herein is a catheter assembly including, in some embodiments, a distal portion of the catheter assembly and a proximal portion of the catheter assembly. The distal portion of the catheter assembly includes a catheter tube and a flow-directing cap. The catheter tube includes a pair of lumens extending from a distal end portion to a proximal end portion of the catheter tube. The flow-directing cap is about the proximal end portion of the catheter tube. The flow-directing cap includes a valve in the flow-directing cap at a proximal end of the catheter tube. The proximal portion of the catheter assembly includes a tunneling shaft. The tunneling shaft has a first end portion and a second end portion configured for insertion into the flow-directing cap for subcutaneously tunneling the tunneling shaft and the catheter tube in a patient using a retrograde tunneling technique.

In some embodiments, the first end portion and the second portion of the tunneling shaft are each configured with a circumferential or wedge-shaped barb configured to interlock with a complementary feature in the flow-directing cap about the proximal end portion of the catheter tube.

In some embodiments, the proximal portion of the catheter assembly further includes an ambidextrous handle and a lock collar. The ambidextrous handle includes a hub disposed in and extending from a distal end portion of the handle. The hub is configured for insertion of the first end portion or the second end portion of the tunneling shaft into a socket of the hub. The lock collar is configured to slide over the tunneling shaft and interlock with the hub to lock the tunneling shaft on the handle.

In some embodiments, the first end portion and the second portion of the tunneling shaft are each configured with a circumferential or wedge-shaped barb configured to interlock with a complementary feature in the socket of the hub.

In some embodiments, the catheter tube is configured to be cut to length at a location on the catheter tube distal to the flow-directing cap for attaching the catheter tube to a pair of cannulas.

Also disclosed herein is a method of placing a catheter assembly for vascular access including, in some embodiments, priming a pair of lumens of a catheter tube of a first catheter assembly with a priming fluid from a distal end portion of the catheter tube; accessing a vessel in a vasculature of a patient from an access site on a neck of the patient; inserting the distal end portion of the catheter tube into the vessel of the patient; creating an exit site on a chest of the patient; tunneling a proximal end portion of the catheter tube as part of a second catheter assembly from the access site to the exit site; and connecting the proximal end portion of the catheter tube to a proximal portion of a third catheter assembly by way of a connection mechanism of the third catheter assembly, wherein the catheter tube forms a distal portion of the third catheter assembly.

In some embodiments, the first catheter assembly includes a flow-directing cap about the proximal end portion of the catheter tube, a priming adapter coupled to a priming stylet disposed in the distal end portion of the catheter tube, and an over-the-wire ("OTW") stylet extending from the proximal end portion of the catheter tube beyond the distal end portion of the catheter tube. Priming the pair of lumens includes priming both an arterial lumen and a venous lumen of the pair of lumens through the priming stylet inserted into either the arterial lumen or the venous lumen while the OTW stylet is disposed in another of the arterial lumen or the venous lumen.

In some embodiments, the method further includes removing the priming adapter and the priming stylet before inserting the distal end portion of the catheter tube into the vessel of the patient. Inserting the distal end portion of the catheter tube into the vessel of the patient includes advancing the distal end portion of the catheter tube into the vessel of the patient over a guidewire disposed in the OTW stylet.

In some embodiments, the first catheter assembly includes a flow-directing cap about the proximal end portion of the catheter tube and a priming adapter coupled to a priming stylet disposed in the distal end portion of the catheter tube. Priming the pair of lumens includes priming both an arterial lumen and a venous lumen of the pair of lumens through the priming stylet inserted into either the arterial lumen or the venous lumen.

In some embodiments, the priming adapter is configured with a Luer-tapered connector. Priming the pair of lumens includes connecting a syringe to the priming adapter by way of the Luer-tapered connector and priming the pair of lumens with sterile saline as the priming fluid from the syringe.

In some embodiments, the method further includes removing the priming adapter and the priming stylet before inserting the distal end portion of the catheter tube into the vessel of the patient; tunneling a tunneling shaft from the access site to the exit site; and connecting the tunneling shaft to the flow-directing cap to form the second catheter assembly for tunneling the proximal end portion of the catheter tube from the access site to the exit site.

In some embodiments, the method further includes connecting a handle to the tunneling shaft for tunneling the tunneling shaft from the access site to the exit site, tunneling the proximal end portion of the catheter tube from the access site to the exit site, or both.

In some embodiments, the method further includes cutting the catheter tube to length distal to the flow-directing cap, thereby cutting off the flow-directing cap and exposing the arterial lumen and the venous lumen of the pair of lumens of the catheter tube.

In some embodiments, the method further includes cutting the catheter tube to length distal to the flow-directing cap, thereby cutting off the flow-directing cap and exposing the arterial lumen and the venous lumen of the pair of lumens of the catheter tube; and connecting the arterial lumen and the venous lumen at the proximal end portion of the catheter tube to an arterial lumen and a venous lumen of a pair cannulas disposed in and extending from a bifurcated hub of the proximal portion of the third catheter assembly.

In some embodiments, the connection mechanism is a collared connection mechanism including a collar configured to fit over a proximal end portion of the catheter tube.

These and other features of the concepts provided herein will become more apparent to those of skill in the art in view of the accompanying drawings and following description, which disclose particular embodiments of such concepts in greater detail.

DRAWINGS

FIG. 10A illustrates a side view of a clamping-style hub for an eighth connection mechanism of a catheter assembly in accordance with some embodiments.

FIG. 10B illustrates a top view of the clamping-style hub for the eighth connection mechanism of the catheter assembly in accordance with some embodiments.

FIG. 16A illustrates a fourteenth connection mechanism of a catheter assembly in accordance with some embodiments.

FIG. 16B illustrates a hub-based securement feature of the fourteenth connection mechanism in accordance with some embodiments.

FIG. 16C illustrates a close-up of the fourteenth connection mechanism of the catheter assembly in accordance with some embodiments.

FIG. 18A illustrates a sixteenth connection mechanism of a catheter assembly in accordance with some embodiments.

FIG. 18B illustrates a fastener of a catheter tube-based securement feature of the sixteenth connection mechanism in accordance with some embodiments.

FIG. 21A illustrates a nineteenth connection mechanism of a catheter assembly in accordance with some embodiments.

FIG. 21B illustrates a collet proper of the nineteenth connection mechanism in accordance with some embodiments.

FIG. 25A illustrates a twenty-third connection mechanism of a catheter assembly in accordance with some embodiments.

FIG. 25B illustrates a collet proper of the twenty-third connection mechanism in accordance with some embodiments.

FIG. 25C illustrates a longitudinal cross section of the collet proper of the twenty-third connection mechanism in accordance with some embodiments.

FIG. 28 illustrates a twenty-seventh connection mechanism of a catheter assembly in accordance with some embodiments.

FIG. 29 illustrates a twenty-eighth connection mechanism of a catheter assembly in accordance with some embodiments.

FIG. 30A illustrates a twenty-ninth connection mechanism of a catheter assembly including a compression insert in accordance with some embodiments.

FIG. 30B illustrates a perspective view of the compression insert of FIG. 30A.

FIG. 33A illustrates a catheter assembly for priming a catheter tube in accordance with some embodiments.

FIG. 33B illustrates a transverse cross section of the catheter tube of the catheter assembly of FIG. 33A.

FIG. 33C illustrates a longitudinal cross section of a distal end portion of the catheter tube of the catheter assembly of FIG. 33A.

FIG. 33D illustrates a longitudinal cross section of a proximal end portion of the catheter tube of the catheter assembly of FIG. 33A.

DESCRIPTION

Figure 1A:
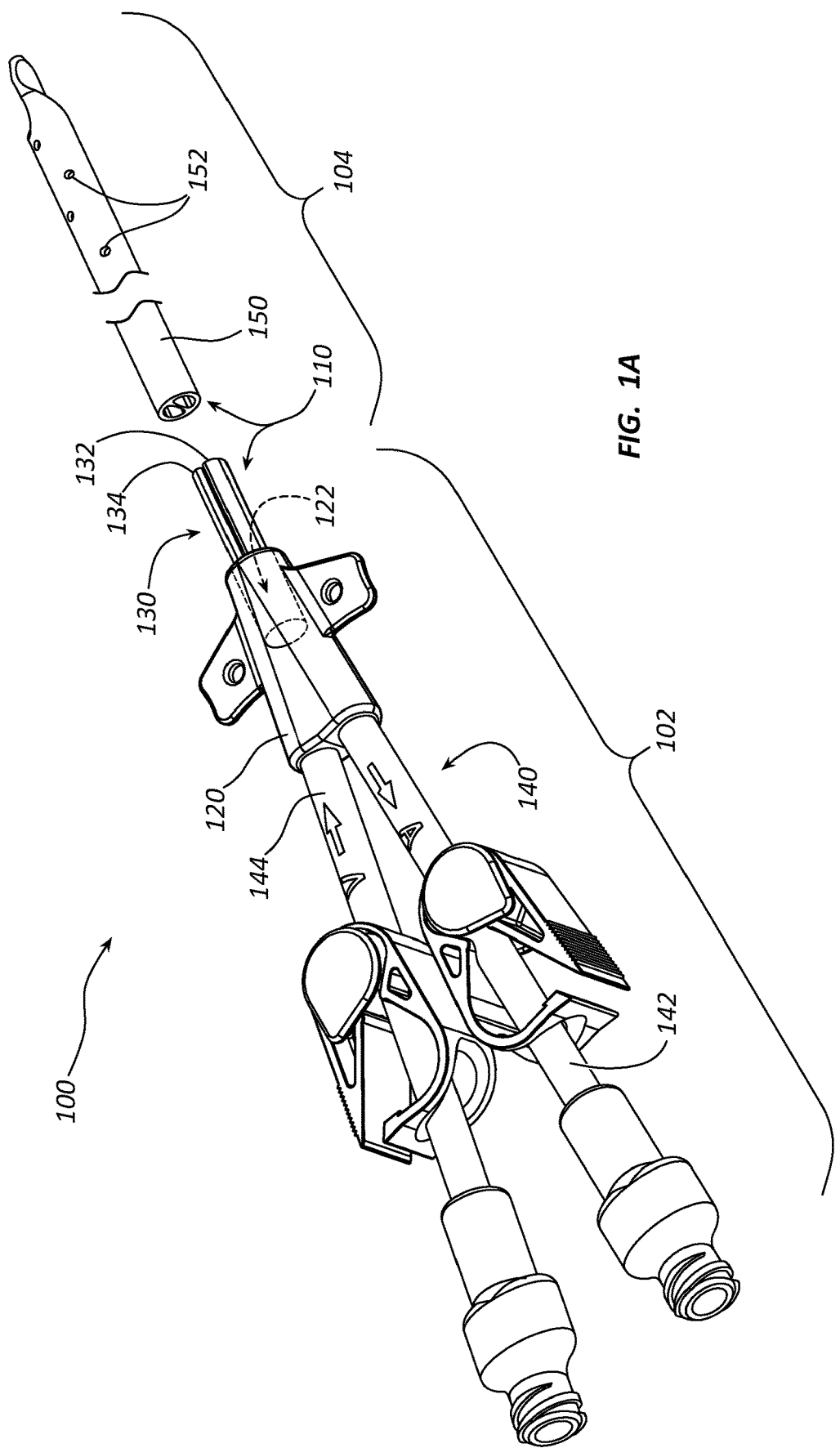
FIG. 1A illustrates a catheter assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

When placing a catheter assembly such as a hemodialysis catheter in a patient by way of a retrograde tunneling technique, a clinician primes a catheter tube of the catheter to safeguard against air embolism, places a distal end of the catheter tube in a vessel of the patient, and cuts off a proximal end portion of the catheter tube to customize a length of the catheter tube according to the patient's anatomy. Afterward, a freshly cut proximal end of the catheter tube is tunneled under the patient's skin in a retrograde fashion to a location on the patient's chest where the catheter tube is connected to a remainder of the catheter assembly. When the catheter tube is connected to a remainder of the catheter assembly such as a hub and any extension tubes connected thereto, the catheter tube should be attached to the remainder of the catheter assembly in a simple, secure, and leakproof manner.

Disclosed herein are catheter assemblies and methods thereof that address various aspects of at least the retrograde tunneling technique. The catheter assemblies include, but are not limited to, catheter assemblies configured for vascular access, catheter assemblies configured for priming, catheter assemblies configured for tunneling, and mechanisms for connecting catheter tubes to their respective catheter assemblies. The methods include, but are not limited to, priming, tunneling, and connecting catheter tubes to their respective catheter assemblies.

The catheter assemblies and methods thereof for the retrograde tunneling technique are generally presented in accordance with the following outline:

A. Catheter assemblies for vascular access
   B. Hubs for vascular-access catheter assemblies
   C. Connection mechanisms for vascular-access catheter assemblies
      1. Collarless connection mechanisms
         a. Hub-based securement features
         b. Interlocking hub-based and catheter-tube based securement features
         c. Clamping-style hubs
      2. Collared connection mechanisms
         a. Compression sleeves
         b. Over-the-hub interlocking collars
         c. Hub-based interlocking arms
         d. Collar-based interlocking arms
         e. Collet-type: Hub-based receivers
         f. Collet-type: Collar-based receivers
      3. Other connection mechanisms
      4. Compression inserts in connection mechanisms
      5. Coatings for connection mechanisms
   D. Catheter assemblies for priming
   E. Catheter assemblies for tunneling
   F. Methods While the foregoing outline is provided, the outline does not limit the scope of the concepts presented herein. Again, it should also be understood that a particular embodiment disclosed herein can have features that can be readily separated from the particular embodiment and optionally combined with or substituted for features of any of a number of other embodiments disclosed herein.

A. Catheter Assemblies for Vascular Access

Figure 1B:
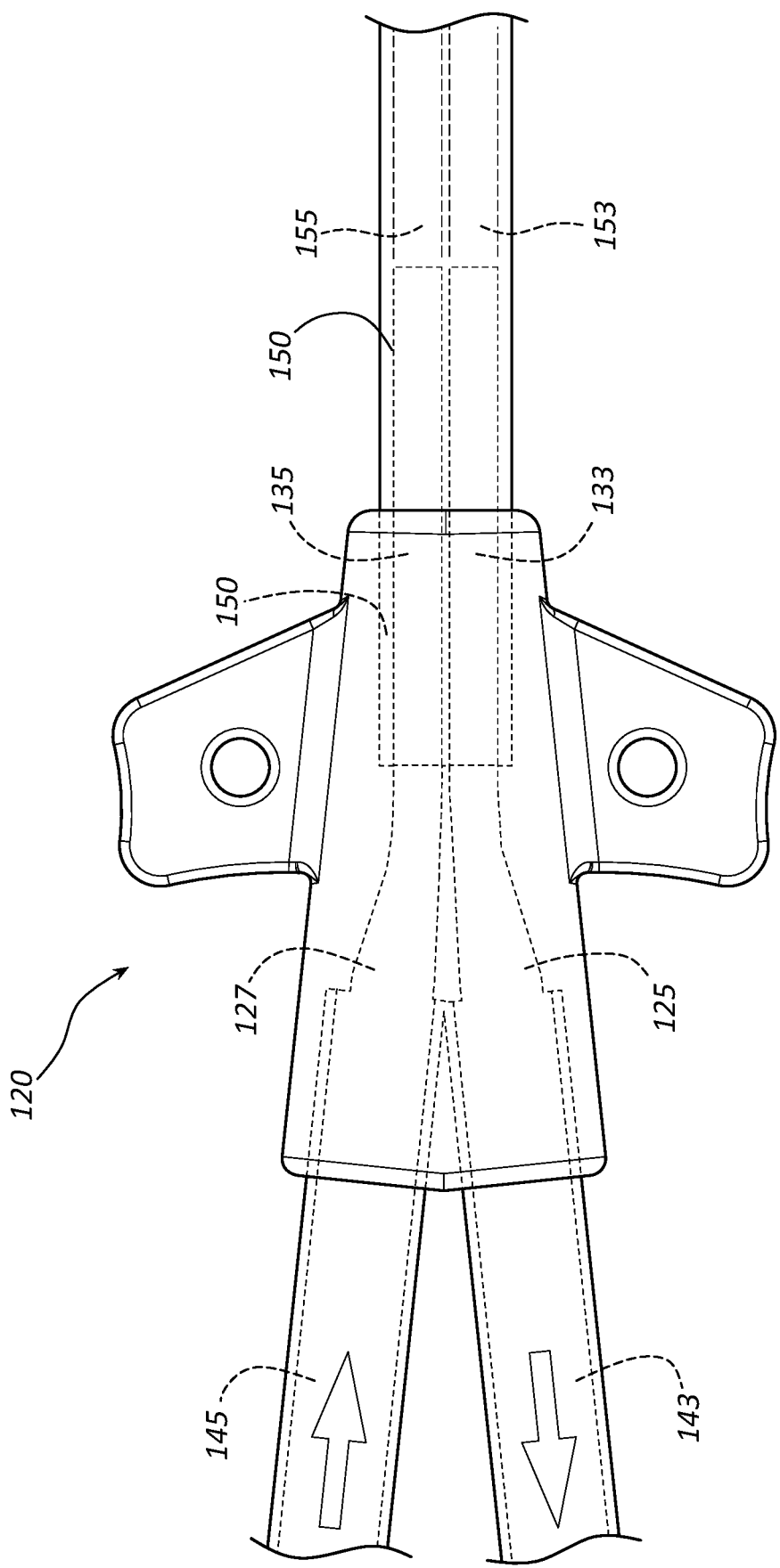
FIG. 1B illustrates a hub of a catheter assembly in accordance with some embodiments.

FIG. 1A illustrates a catheter assembly 100 in accordance with some embodiments. FIG. 1B illustrates a hub 120 of the catheter assembly 100 in accordance with some embodiments.

As shown, the catheter assembly 100 includes a proximal portion 102 of the catheter assembly 100, a distal portion 104 of the catheter assembly 100, and a connection mechanism 110 configured to connect the proximal portion 102 of the catheter assembly 100 to the distal portion 104 of the catheter assembly 100. The proximal portion 102 of the catheter assembly 100 includes the hub 120 as a bifurcated hub 120, a pair of cannulas 130 partially disposed in and distally extending from the bifurcated hub 120, and a pair of extension tubes 140 disposed in and proximally extending from the bifurcated hub 120. The distal portion 104 of the catheter assembly 100 includes a catheter tube 150. The connection mechanism 110 is further configured to connect the catheter tube 150 of the distal portion 104 of the catheter assembly 100 to the pair of cannulas 130 of the proximal portion 102 of the catheter assembly 100, thereby providing a fluid-tight connection between the catheter tube 150 and the pair of cannulas 130.

At least the pair of cannulas 130 and the pair of extension tubes 140 form a proximal pair of lumens (see FIG. 1B) extending through the proximal portion 102 of the catheter assembly 100. The distal portion 104 of the catheter assembly 100 includes the catheter tube 150 with a distal pair of lumens (see FIG. 1B) extending through the distal portion 104 of the catheter assembly 100. The catheter tube 150 is configured to fit over the pair of cannulas 130 to extend the proximal and distal pairs of lumens through an entirety of the catheter assembly 100 as an extended pair of lumens (see FIG. 1B). The extended pair of lumens includes an arterial lumen and a venous lumen.

At least an arterial cannula 132 of the pair of cannulas 130 and an arterial extension tube 142 of the pair of extension tubes 140 form a proximal portion of the arterial lumen by way of their lumens. That is, the proximal portion of the arterial lumen includes at least arterial-cannula lumen 133 and arterial-extension-tube lumen 143. At least a venous cannula 134 of the pair of cannulas 130 and a venous extension tube 144 of the pair of extension tubes 140 form a proximal portion of the venous lumen by way of their lumens. That is, the proximal portion of the venous lumen includes at least venous-cannula lumen 135 and venous-extension-tube lumen 145. If the arterial cannula 132 and the arterial extension tube 142 are not directly connected in the hub 120, an arterial internal-fluid passageway 125 of the hub 120 connects the arterial-cannula lumen 133 and the arterial-extension-tube lumen 143 to form the proximal portion of the arterial lumen. Likewise, if the venous cannula 134 and the venous extension tube 144 are not directly connected in the hub 120, a venous internal-fluid passageway 127 of the hub 120 connects the venous-cannula lumen 135 and the venous-extension-tube lumen 145 to form the proximal portion of the venous lumen.

At least the catheter tube 150 forms a distal portion of both the arterial lumen and a distal portion of the venous lumen by way of its lumens. That is, the distal portion of the arterial lumen includes at least an arterial-catheter-tube lumen 153, and the distal portion of the venous lumen includes at least a venous-catheter-tube lumen 155, thereby forming the distal pair of lumens extending through the distal portion 104 of the catheter assembly 100.

While the catheter assembly 100 shown in FIG. 1A is in accordance with certain embodiments of catheter assemblies having a bifurcated hub, it should be understood that other intended embodiments of the catheter assemblies need not include the bifurcated hub 120. That is, the hub need not be furcated in the other intended embodiments of the catheter assemblies, or the hub can be more extensively furcated (i.e., multifurcated such as trifurcated, quadrifurcated, etc.) in the other intended embodiments of the catheter assemblies. It follows that a degree of furcation of the hub prescribes a number of cannulas and a number of extension tubes in the catheter assemblies. For example, a catheter assembly with a nonfurcated hub includes one cannula and one extension tube, a catheter assembly such as the catheter assembly 100 with the bifurcated hub 120 includes two cannulas (e.g., the pair of cannulas 130) and two extension tubes (e.g., the pair of extension tubes 140), a catheter assembly with a trifurcated hub includes three cannulas and three extension tubes, and so on.

While the catheter assembly 100 shown in FIG. 1A is in accordance with certain embodiments of the catheter assemblies having the connection mechanism 110 with a bore 122 sized to accommodate the catheter tube 150, it should be understood that other intended embodiments of the catheter assemblies need not include the connection mechanism 110. That is, a connection mechanism need not include the bore 122 in the other intended embodiments of the catheter assemblies, or the connection mechanism can include the bore 122, or a socket, along with one or more additional features in the other intended embodiments of the catheter assemblies. Indeed, the other intended embodiments of the catheter assemblies can be configured with any connection mechanism or combination of connection mechanisms disclosed herein.

B. Hubs for Vascular-Access Catheter Assemblies

Figure 2A:
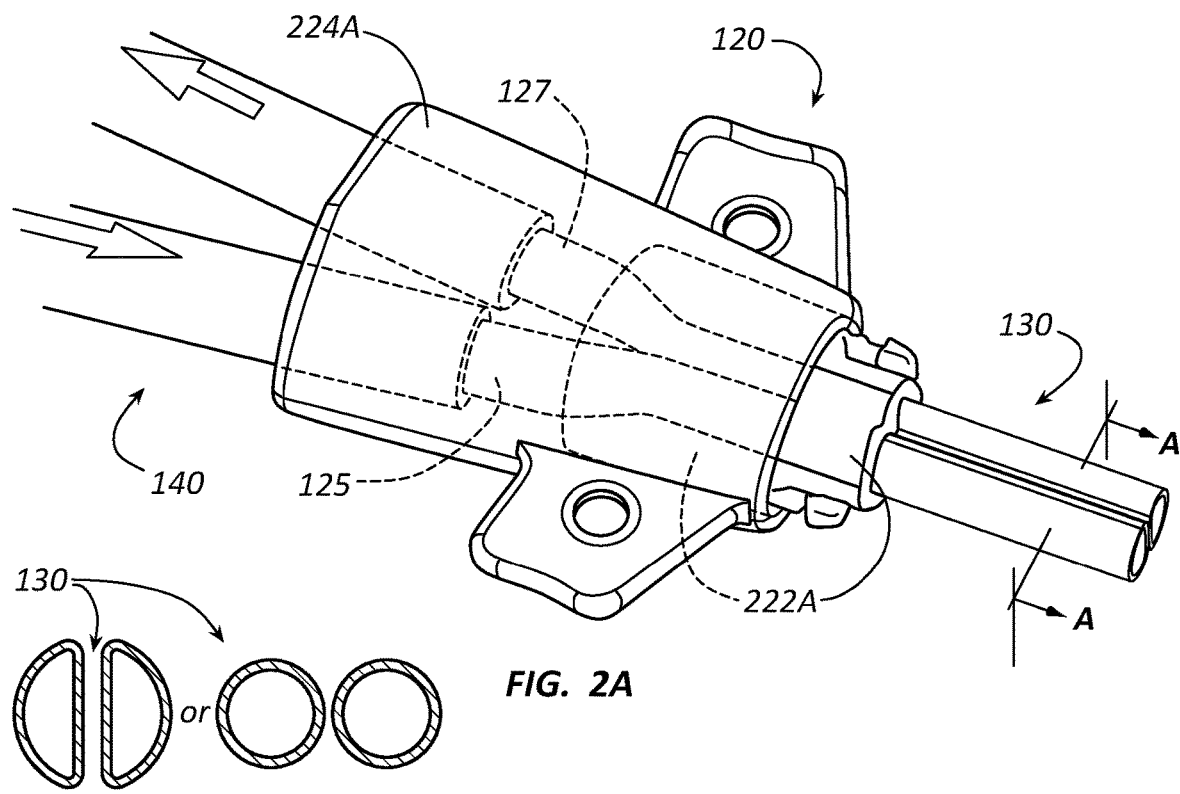
FIG. 2A illustrates a hub including a pair of straight cannulas in accordance with some embodiments.
Figure 2B:
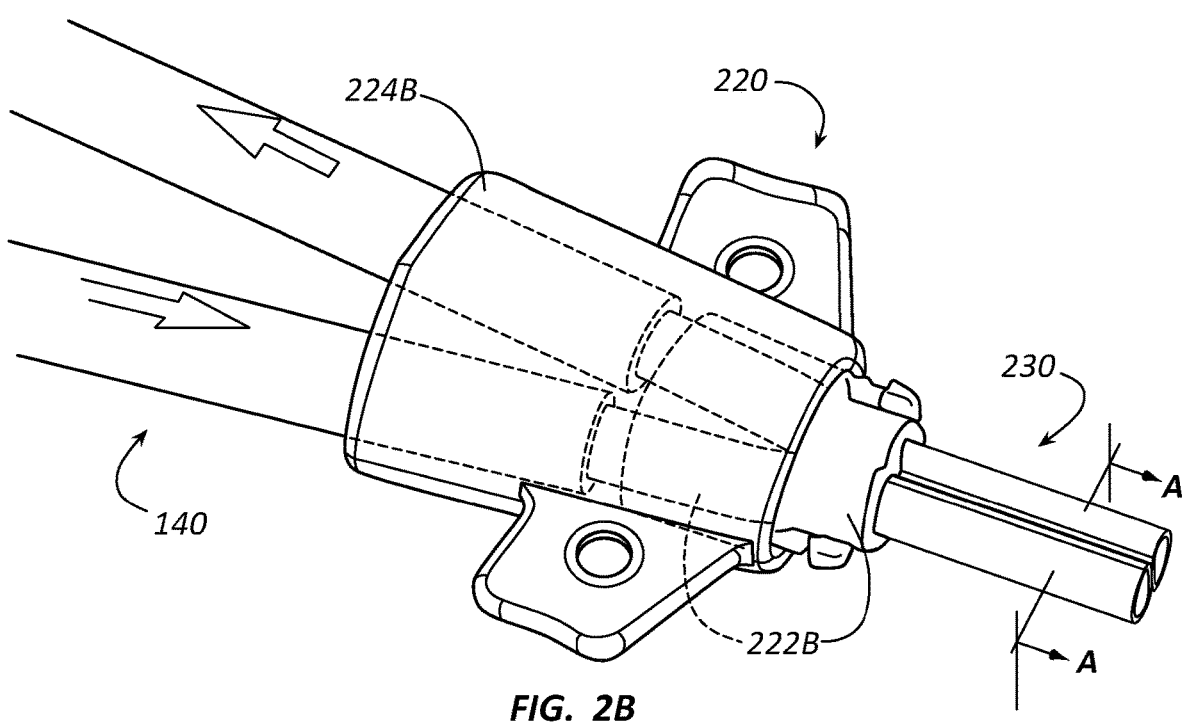
FIG. 2B illustrates a hub including a pair of bent cannulas in accordance with some embodiments.

FIG. 2A illustrates the hub 120 including a pair of straight cannulas 130 in accordance with some embodiments. FIG. 2B illustrates a hub 220 including a pair of bent cannulas 230 in accordance with some embodiments.

As described in reference to FIGS. 1A and 1B, the hub 120 can be a bifurcated hub 120 as shown in FIG. 2A. A catheter assembly including such a hub (e.g., the catheter assembly 100) can include the pair of straight cannulas 130 partially disposed in and distally extending from the bifurcated hub 120, as well as the pair of extension tubes 140 disposed in and proximally extending from the bifurcated hub 120. Likewise, a catheter assembly including the hub 220, which can also be a bifurcated hub as shown in FIG. 2B, can include the pair of bent cannulas 230 partially disposed in and distally extending from the bifurcated hub 220, as well as the pair of extension tubes 140 disposed in and proximally extending from the bifurcated hub 220. Each cannula of the pair of cannulas 130 or 230 can be either 'D'-shaped or circular in cross section as shown in FIGS. 2A and 2B. While the 'D'-shaped cannulas can provide compact hubs that are useful for narrower catheter tubes, the circular cannulas can be configured with larger diameters for greater flow rates with flow parameters that are more easily controlled. In addition, the circular cannulas can have more uniform catheter-tube connections and be more easily manufactured than the 'D'-shaped cannulas. Whether the pair of cannulas 130 or 230 are 'D'-shaped or circular in cross section, the pair of cannulas 130 or 230 can include a thin coating, sleeves, or shrink wrap or another compliant material over the exposed portions of the pair of cannulas 130 or 320 to aid in both disposing the catheter tube 150 thereover as well as forming a better, more compliant seal between the pair of cannulas 130 or 230 and the catheter tube 150.

Each hub of the bifurcated hubs 120 and 220 further includes two portions of the hub, namely an inner hub and an outer hub. Each of the inner hub and the outer hub can be a same or different molded plastic with a same or different durometer. For example, the bifurcated hub 120 can include an inner hub 222A of a first plastic molded over and optionally bonded to the pair of cannulas 130, which can be the pair of straight cannulas 130 as shown. An outer hub 224A of a lower-durometer plastic can, in turn, be molded over the inner hub 222A. Likewise, the bifurcated hub 220 can include an inner hub 222B of a first plastic molded over and optionally bonded the pair of cannulas 230, which can be the pair of bent cannulas 230 as shown. An outer hub 224B of a lower-durometer plastic can, in turn, be molded over the inner hub 222B. As described in reference to FIGS. 1A and 1B, if the arterial cannula 132 and the arterial extension tube 142 are not directly connected in a hub like they are in the hub 220, the arterial internal-fluid passageway 125 connects the arterial-cannula lumen 133 and the arterial-extension-tube lumen 143 as in the hub 120. Likewise, if the venous cannula 134 and the venous extension tube 144 are not directly connected in a hub like they are in the hub 220, the venous internal-fluid passageway 127 of the hub 120 connects the venous-cannula lumen 135 and the venous-extension-tube lumen 145 as in the hub 120.

C. Connection Mechanisms for Vascular-Access Catheter Assemblies

As described in reference to FIGS. 1A and 1B, a catheter assembly such as the catheter assembly 100 can include the connection mechanism 110, which is configured to fluidly connect the catheter tube 150 of the distal portion 104 of the catheter assembly 100 to the pair of cannulas 130 of the proximal portion 102 of the catheter assembly 100. Indeed, connection mechanisms including the connection mechanism 110 provide fluid-tight connections between catheter tubes and cannulas in catheter assemblies when connected. Again, it should be understood that other intended embodiments of catheter assemblies need not include the connection mechanism 110. That is, connection mechanisms in the other intended embodiments of the catheter assemblies need not include the bore 122, or the connection mechanisms can include the bore 122, or a socket, along with one or more additional features in the other intended embodiments of the catheter assemblies. Indeed, the other intended embodiments of the catheter assemblies can be configured with any connection mechanism or combination of connection-mechanism features disclosed herein, which connection mechanisms include at least collarless connection mechanisms (e.g., the connection mechanism 110) or collared connection mechanisms as set forth herein.

1. Collarless Connection Mechanisms

Collarless connection mechanisms for catheter assemblies such as the catheter assembly 100 include, but are not limited to, connection mechanisms including hub-based securement features including clamping-style hubs, catheter tube-based securement features, hub-based securement features with interlocking catheter tube-based securement features, or combinations thereof. As set forth herein, the hub-based and catheter tube-based securement features, which can also be considered hub-based and catheter tube-based securement devices, can further include features of their own. For example, a connection mechanism can include both hub-based and catheter tube-based securement features, wherein at least the hub-based securement feature is configured as a clamp, which in turn, includes a hinged piece of the clamp.

a. Hub-Based Securement Features

Figure 3A:
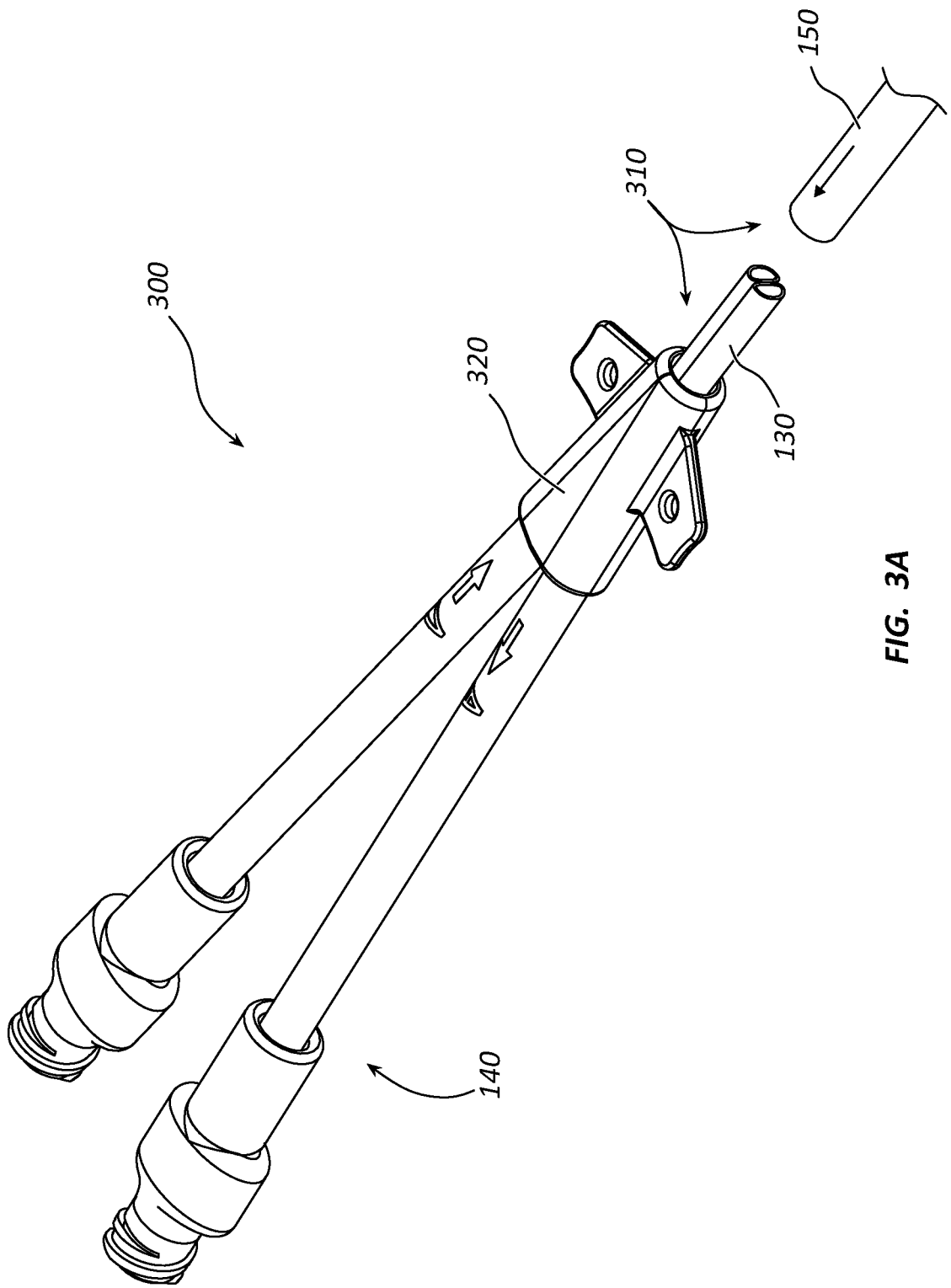
FIG. 3A illustrates a first connection mechanism of a catheter assembly in accordance with some embodiments.
Figure 3B:
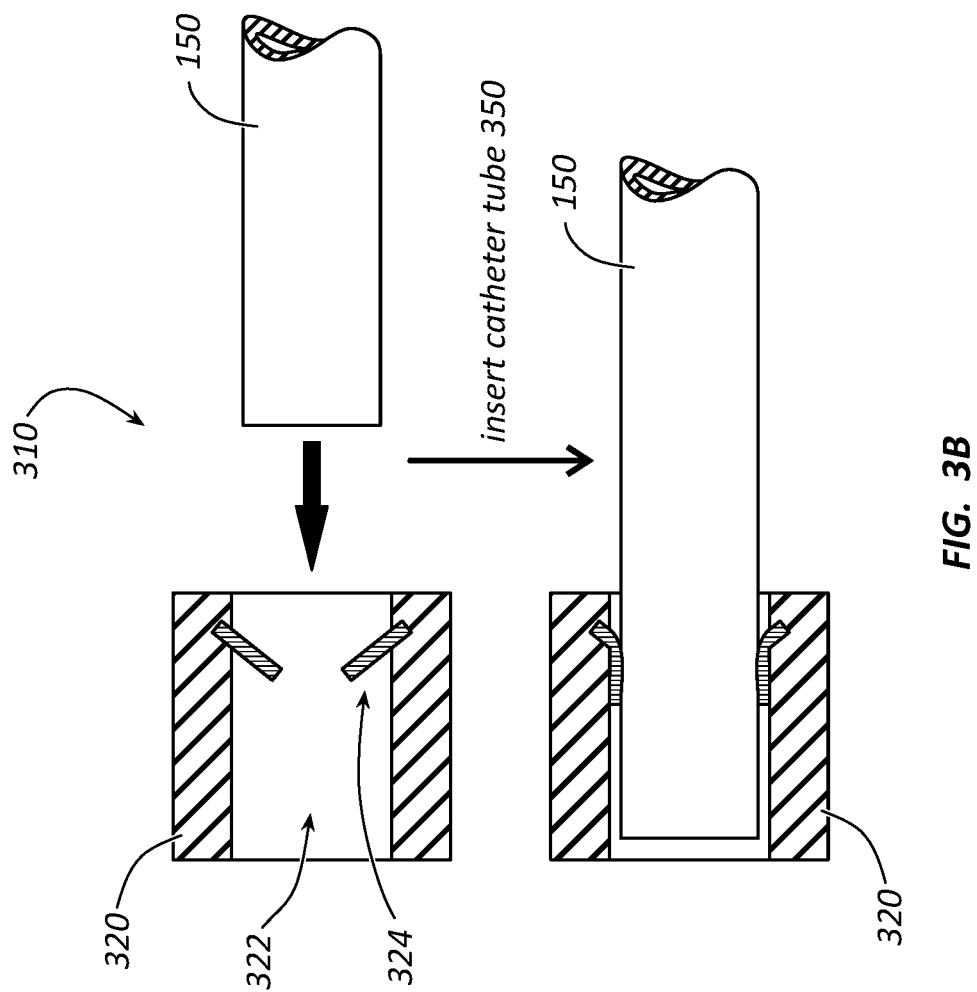
FIG. 3B illustrates the first connection mechanism of the catheter assembly of FIG. 3A in additional detail.

FIG. 3A illustrates a first connection mechanism 310 of a catheter assembly 300 in accordance with some embodiments. FIG. 3B illustrates the first connection mechanism 310 of the catheter assembly 300 of FIG. 3A in additional detail.

As shown, the connection mechanism 310 of the catheter assembly 300 includes a hub 320 with a hub-based securement feature 324 including a bore 322 with one or more circumferential protrusions such as rings, a number of radial protrusions such as pillars, or a combination thereof radially oriented inward toward an axis of the bore 322. The one or more circumferential protrusions, the number of radial protrusions, or the combination thereof of the hub-based securement feature 324 can be configured to displace in a proximal direction upon insertion of the catheter tube 150 into the bore 322 over the pair of cannulas 130 or 230. Displacement of the one or more circumferential protrusions, the number of radial protrusions, or the combination thereof of the hub-based securement feature 324 also serves to compress the catheter tube 150 to a certain degree. The one or more circumferential protrusions, the number of radial protrusions, or the combination thereof of the hub-based securement feature 324 can be further configured with a structural integrity (e.g., thickness) sufficient to resist displacement of the catheter tube 150, once connected, under normal operating conditions, thereby providing a secure fluid-tight connection between the catheter tube 150 and the pair of cannulas 130 or 230 within the hub 320.

Figure 4:
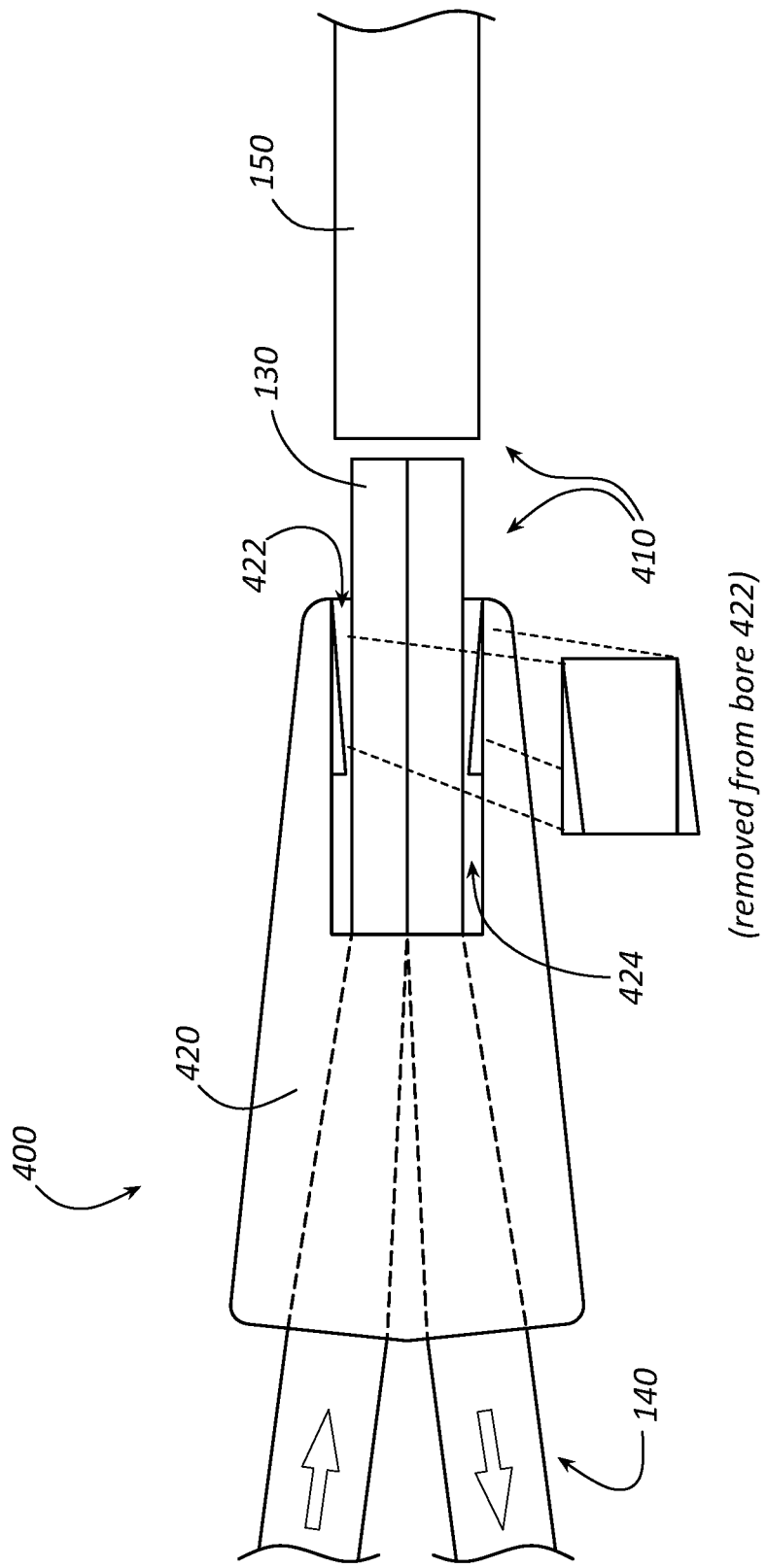
FIG. 4 illustrates a second connection mechanism of a catheter assembly in accordance with some embodiments.

FIG. 4 illustrates a second connection mechanism 410 of a catheter assembly 400 in accordance with some embodiments.

As shown, the connection mechanism 410 of the catheter assembly 400 includes a hub 420 with a hub-based securement feature 424 including a bore 422. The hub-based securement feature 424 can include the bore 422 with an integral protrusion such as circumferential barb radially oriented inward toward an axis of the bore 422, or, in more of a collared connection mechanism, the hub-based securement feature 424 can include a discrete (e.g., separable, detachable, etc.) holed plug (i.e., a plug having a hole) with a similar protrusion configured to fit in the bore 422 with an interference fit such as a press fit. Whether the hub-based securement feature 424 is an integral protrusion of the bore 422 or a discrete holed plug, the bore 422 includes a taper in which a diameter of the bore 422 is greater at a distal end of the bore 422 than the diameter of the bore 422 at a proximal end of the bore 422. A reverse taper is also possible in which the diameter of the bore 422 is greater at the proximal end of the bore 422 than the diameter of the bore 422 at the distal end of the bore 422. The taper or the reverse taper of the bore 422 can be configured to provide compression of the catheter tube 150 upon insertion of the catheter tube 150 into the bore 422 over the pair of cannulas 130 or 230, thereby providing a secure fluid-tight connection between the catheter tube 150 and the pair of cannulas 130 or 230 within the hub 420.

Figure 5:
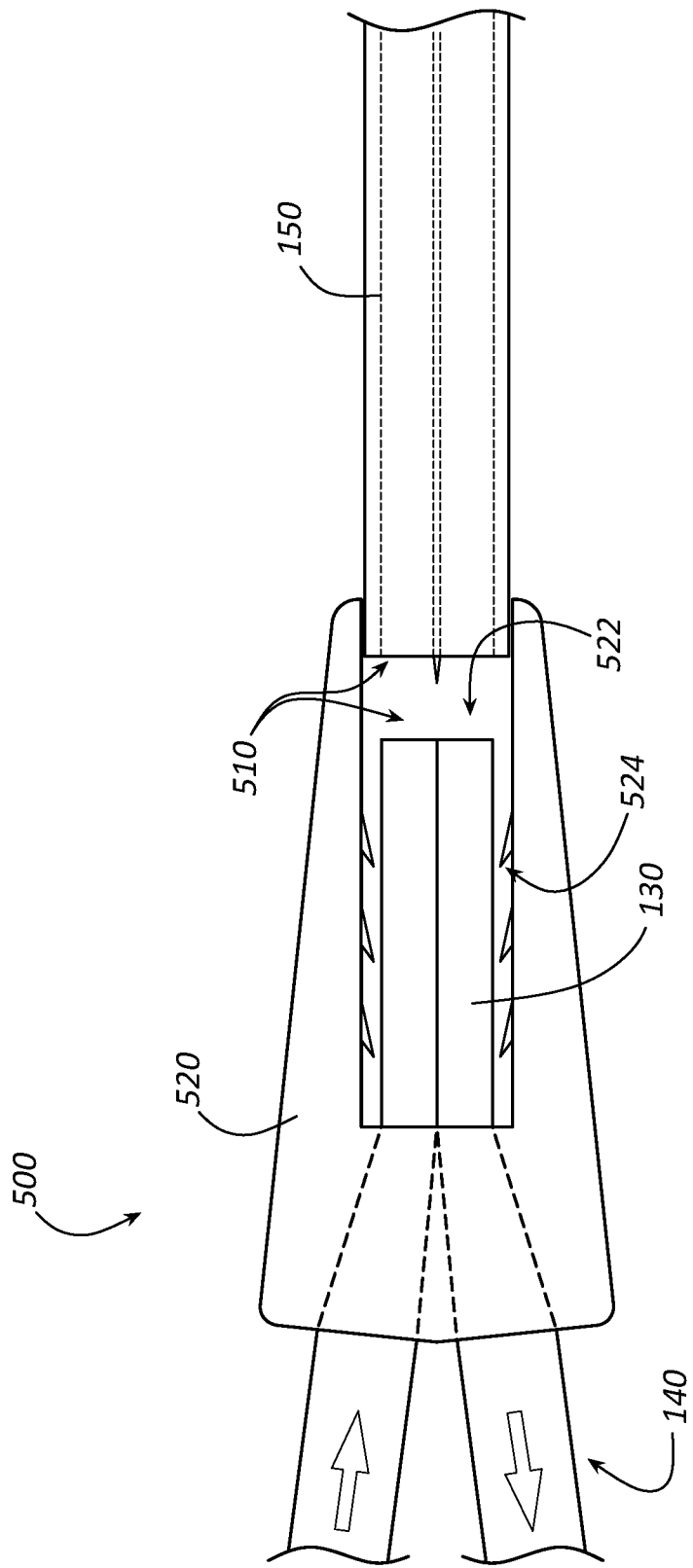
FIG. 5 illustrates a third connection mechanism of a catheter assembly in accordance with some embodiments.

FIG. 5 illustrates a third connection mechanism 510 of a catheter assembly 500 in accordance with some embodiments.

As shown, the connection mechanism 510 of the catheter assembly 500 includes a hub 520 with a hub-based securement feature 524 including a number of pointed protrusions (e.g., barbs or spikes) in a bore 522 oriented inward toward an axis of the bore 522 and backward toward a proximal end portion of the catheter assembly 500. The number of pointed protrusions of the hub-based securement feature 524 can be configured by way of at least their orientation to easily allow insertion of the catheter tube 150 into the bore 522 over the pair of cannulas 130 or 230. Displacement of the number of pointed protrusions in the bore 522 also serves to compress the catheter tube 150 to a certain degree. The number of pointed protrusions in the bore 522 can be further configured with a structural integrity (e.g., thickness) sufficient to resist displacement of the catheter tube 150, once connected, under normal operating conditions, thereby providing a secure fluid-tight connection between the catheter tube 150 and the pair of cannulas 130 or 230 within the hub 320.

b. Interlocking Hub and Catheter-Tube Based Securement Features

Figure 6A:
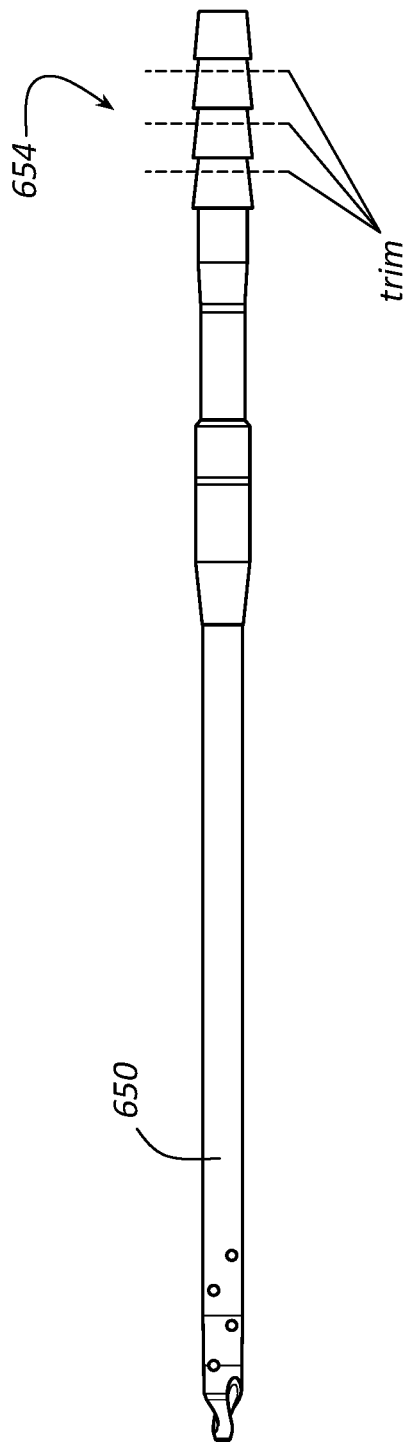
FIG. 6A illustrates a catheter tube for a fourth connection mechanism of a catheter assembly in accordance with some embodiments.
Figure 6B:
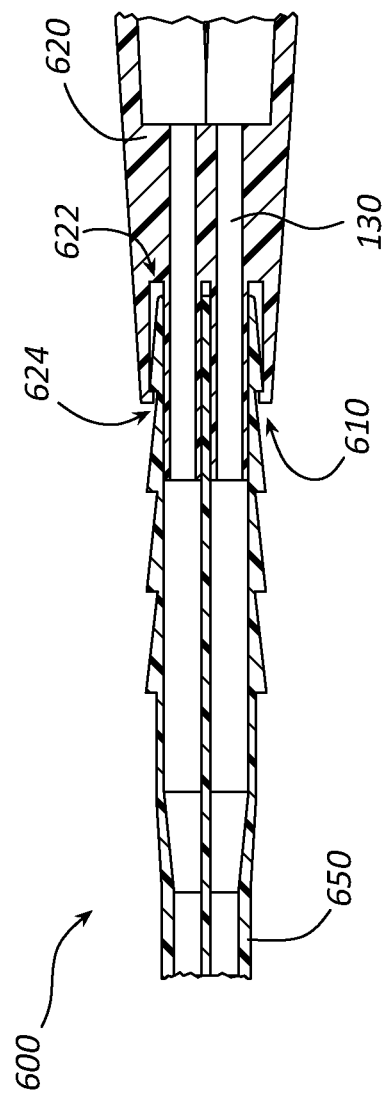
FIG. 6B illustrates the fourth connection mechanism of the catheter assembly in additional detail.

FIG. 6A illustrates a catheter tube 650 for a fourth connection mechanism 610 of a catheter assembly 600 in accordance with some embodiments. FIG. 6B illustrates the fourth connection mechanism 610 of the catheter assembly 600 in additional detail.

As shown, the connection mechanism 610 of the catheter assembly 600 includes a hub 620 with a hub-based securement feature 624 disposed in a socket 622 configured to interlock with a catheter tube 650 having a catheter tube-based securement feature 654. The hub-based securement feature 622 can be one or more circumferential protrusions disposed in the socket 622 such as at a lip of a distal end of the socket 622 and oriented inward toward an axis of the socket 622. The one or more circumferential protrusions in the socket 622 can be configured by way of at least their spacing to interlock with the catheter tube-based securement feature 654 upon insertion of the catheter tube 650 into the socket 622 over the pair of cannulas 130 or 230. The catheter-based securement feature 654 can be one or more circumferential barbs at a proximal end of the catheter tube 650, wherein the one or more circumferential barbs are orientated for retrograde tunneling. When the catheter tube 650 has two or more circumferential barbs as shown, the catheter tube 650 is configured for trimming the proximal end of the catheter tube 650 to a desired length up to a last circumferential barb. The one or more circumferential barbs at the proximal end of the catheter tube 650 can also be configured by way of at least their spacing to interlock with the hub-based securement feature 624 upon insertion of the catheter tube 650 into the socket 622 over the pair of cannulas 130 or 230. The one or more circumferential protrusions in the socket 622 and the one or more circumferential barbs at the proximal end of the catheter tube 650 can be further configured with a structural integrity (e.g., thickness, durometer, etc.) sufficient to resist displacement of the catheter tube 650, once connected, under normal operating conditions, thereby providing a secure fluid-tight connection between the catheter tube 650 and the pair of cannulas 130 or 230 within the hub 620.

c. Clamping-Style Hubs

Figure 7:
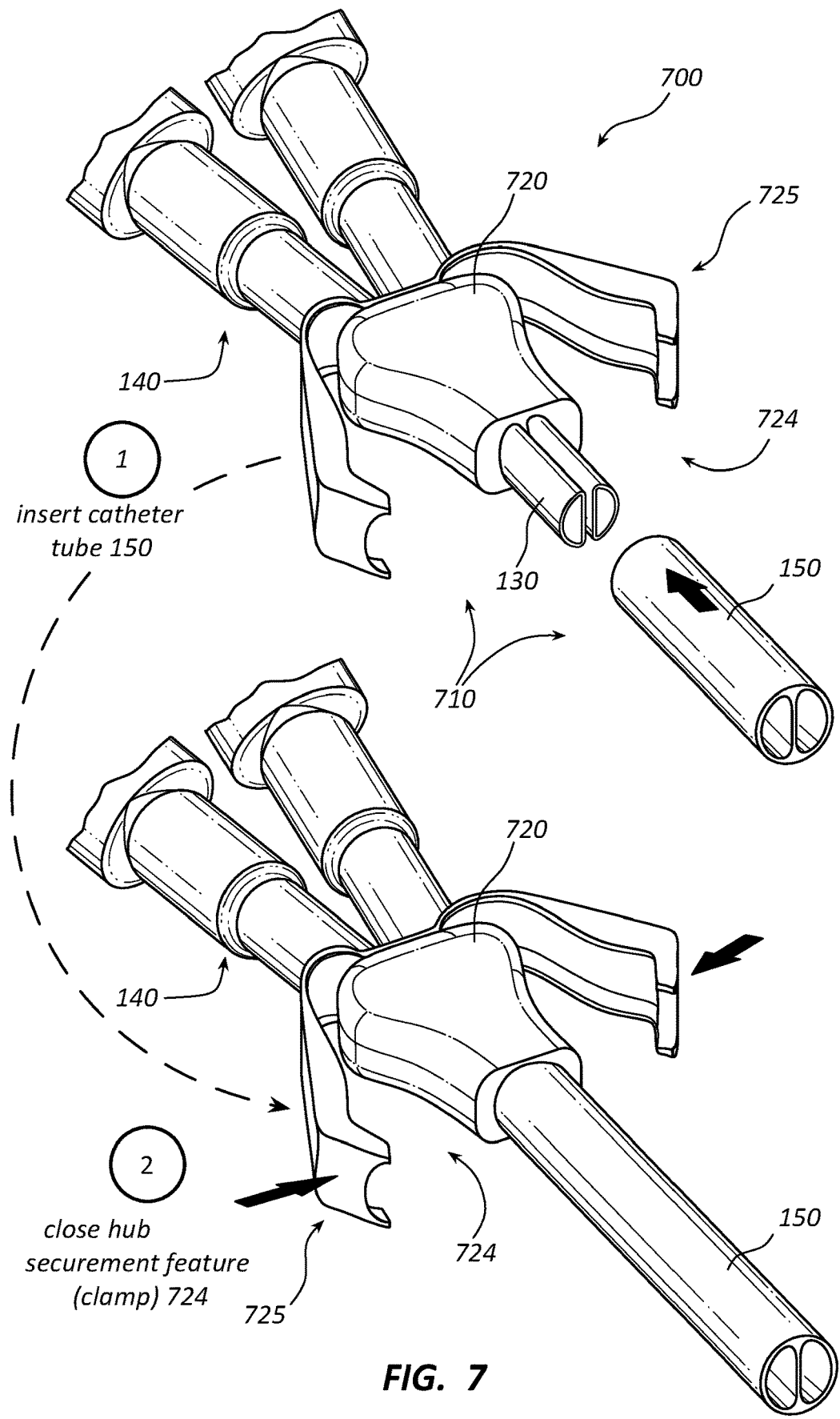
FIG. 7 illustrates a clamping-style hub for a fifth connection mechanism of a catheter assembly in accordance with some embodiments.

FIG. 7 illustrates a clamping-style hub 720 for a fifth connection mechanism 710 of a catheter assembly 700 in accordance with some embodiments.

As shown, the connection mechanism 710 of the catheter assembly 700 includes a hub 720 with a hub-based securement feature 724 configured as a clamp. The hub-based securement feature 724 can include two hinged arms 725 such as two arms on living hinges at a proximal end portion of the hub 720, wherein the two arms 725 are configured to close around the catheter tube 150 upon insertion of the catheter tube 150 over the pair of cannulas 130 or 230. While not shown, the hub 720 can include one or more fasteners such as snaps configured to fasten the two arms 725 to a body of the hub 720 when the two arms 725 are closed. Alternatively, the two arms 725 can include one or more fasteners such as a ratchet system configured to fasten the two arms 725 together around the body of the hub 720 when the two 725 arms are closed. The ratchet system can include at least an integrated gear rack on one arm and a ratchet on the other arm. Closing the two arms 725 around the catheter tube 150 also serves to compress the catheter tube 150 to a certain degree. The hub-based securement feature 724 configured as the clamp including the two arms 725 is configured with a structural integrity and tensile strength sufficient to resist displacement of the catheter tube 150, once connected, under normal operating conditions, thereby providing a secure fluid-tight connection between the catheter tube 150 and the pair of cannulas 130 or 230 within the hub 720.

Figure 8:
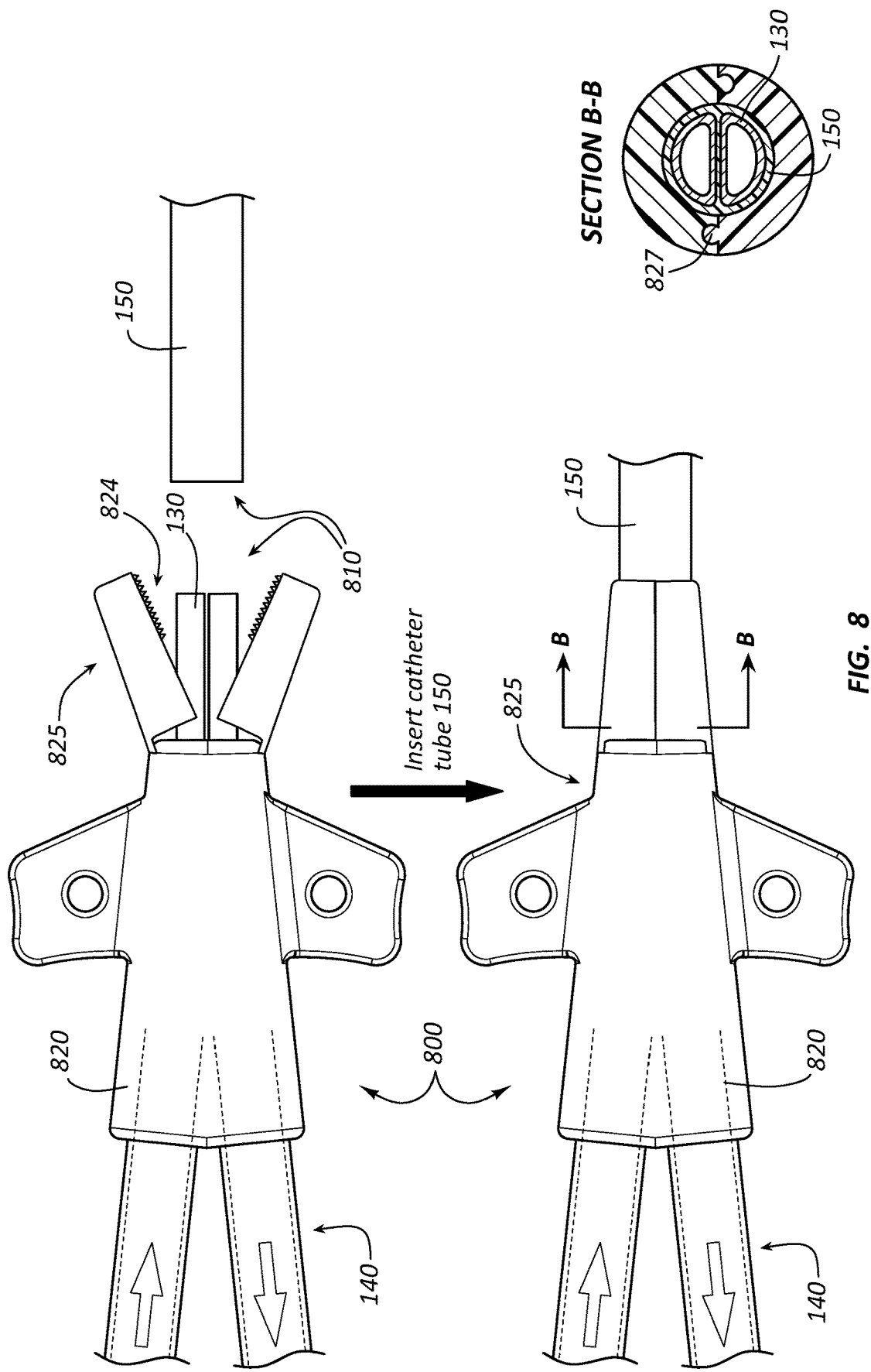
FIG. 8 illustrates a clamping-style hub for a sixth connection mechanism of a catheter assembly in accordance with some embodiments.

FIG. 8 illustrates a clamping-style hub 820 for a sixth connection mechanism 810 of a catheter assembly 800 in accordance with some embodiments.

As shown, the connection mechanism 810 of the catheter assembly 800 includes a hub 820 with a hub-based securement feature 824 configured as a clamp. The hub-based securement feature 824 can include two hinged arms 825 such as two arms on living hinges, wherein the two arms 825 are at a distal end portion of the hub 820 configured to enclose at least a volume commensurate with that of a bore of a hub such as the bore 122 of the hub 120 of the catheter assembly 100. The two arms 825 are configured to close down on the catheter tube 150 upon insertion of the catheter tube 150 over the pair of cannulas 130 or 230. In addition, the two arms 825 are configured with textured surfaces to grip the catheter tube 150 when the two arms 825 are closed around the catheter tube 150. The two arms 825 can also include one or more fasteners such as snaps 827 (see SECTION A-A) configured to fasten the two arms 825 together around the catheter tube 150 and the pair of cannulas 130 or 230 when the two arms 825 are closed. Closing the two arms 825 around the catheter tube 150 also serves to compress the catheter tube 150 to a certain degree. The hub-based securement feature 824 configured as the clamp including the two arms 825 is configured with a structural integrity and tensile strength sufficient to resist displacement of the catheter tube 150, once connected, under normal operating conditions, thereby providing a secure fluid-tight connection between the catheter tube 150 and the pair of cannulas 130 or 230 within the hub 820.

Figure 9:
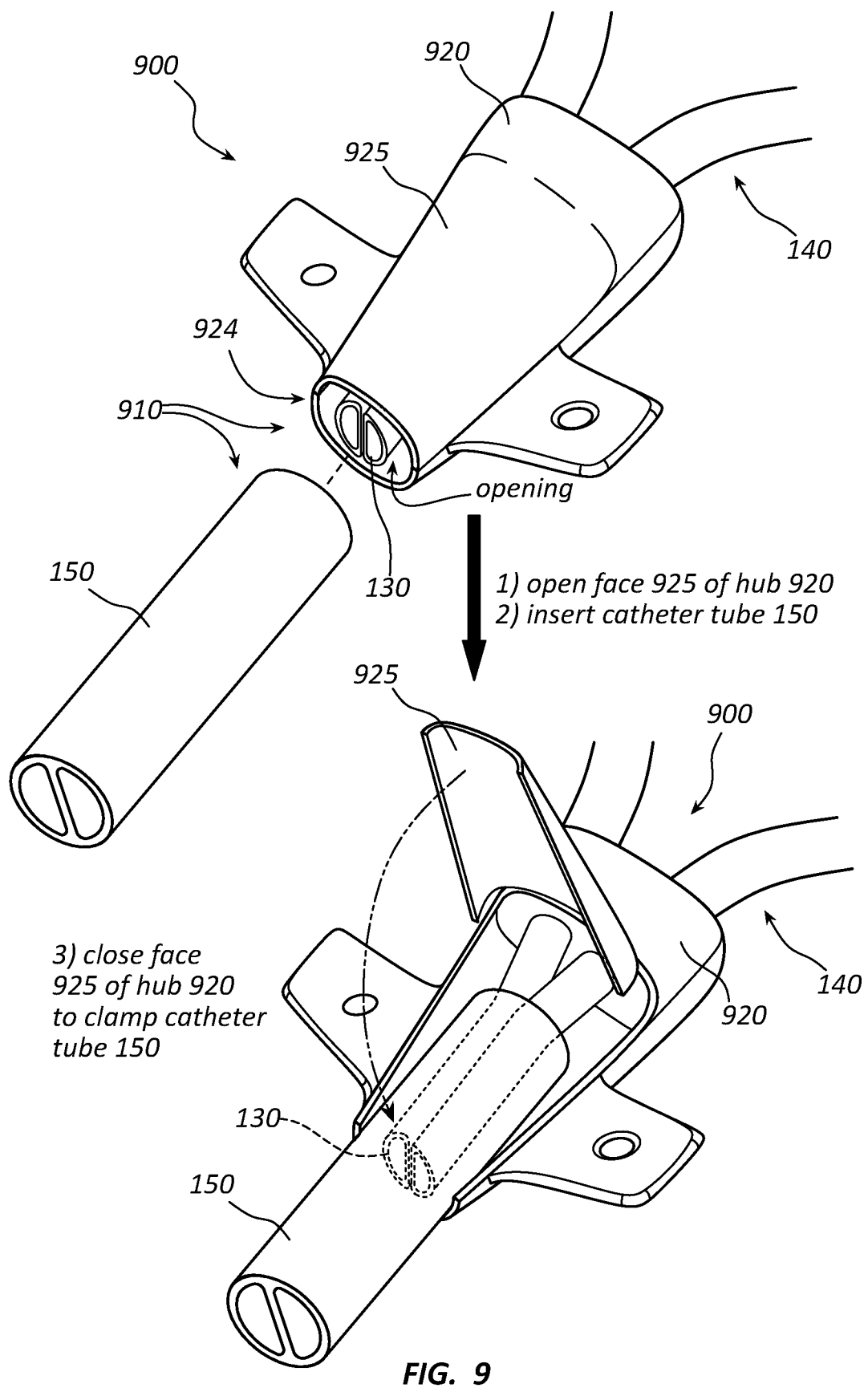
FIG. 9 illustrates a clamping-style hub for a seventh connection mechanism of a catheter assembly in accordance with some embodiments.

FIG. 9 illustrates a clamping-style hub 920 for a seventh connection mechanism 910 of a catheter assembly 900 in accordance with some embodiments.

As shown, the connection mechanism 910 of the catheter assembly 900 includes a hub 920 with a hub-based securement feature 924 configured as a clamp. The hub-based securement feature 924 can include a hub face 925 on a hinge such as a living hinge at a proximal end portion of the hub 920, wherein the hub face 925 is configured to close down on the catheter tube 150 upon insertion of the catheter tube 150 over the pair of cannulas 130 or 230. In addition, a lip around an opening of the hub 920 formed by a body of the hub 920 and the hub face 925 (i.e., the opening configured to accommodate the catheter tube 150) can be configured with a textured surface to grip the catheter tube 150 when the hub face 925 is closed around the catheter tube 150. While not shown, the hub 920 can include one or more fasteners such as snaps configured to fasten the hub face 925 to the body of the hub 920 when the hub face 925 is closed down on the catheter tube 150. Closing the hub face 925 down on the catheter tube 150 also serves to compress the catheter tube 150 to a certain degree. The hub-based securement feature 924 configured as the clamp including the hub face 925 is configured with a structural integrity and tensile strength sufficient to resist displacement of the catheter tube 150, once connected, under normal operating conditions, thereby providing a secure fluid-tight connection between the catheter tube 150 and the pair of cannulas 130 or 230 within the hub 920.

FIG. 10A illustrates a side view of a clamping-style hub 1020 for an eighth connection mechanism 1010 of a catheter assembly 1000 in accordance with some embodiments. FIG. 10B illustrates a top view of the clamping-style hub 1020 for the eighth connection mechanism 1010 of the catheter assembly 1000 in accordance with some embodiments.

As shown, the connection mechanism 1010 of the catheter assembly 1000 includes a hub 1020 with a hub-based securement feature 1024 configured as a clamp. The hub-based securement feature 1024 can include a hub door 1025 on a hinge such as a living hinge, wherein the hub door 1025 is at a distal end portion of the hub 1020 configured to cover at least a volume of the hub 1020 commensurate with that of a bore of a hub such as the bore 122 of the hub 120 of the catheter assembly 100. The hub door 1025 is configured to close down on the catheter tube 150 upon insertion of the catheter tube 150 over the pair of cannulas 130 or 230. In addition, a lip around an opening of the hub 1020 formed by a body of the hub 1020 and the hub door 1025 (i.e., the opening configured to accommodate the catheter tube 150) can be configured with a textured surface to grip the catheter tube 150 when the hub door 1025 is closed around the catheter tube 150. While not shown, the hub 1020 can include one or more fasteners such as snaps configured to fasten the hub door 1025 to the body of the hub 1020 when the hub door 1025 is closed down on the catheter tube 150. Closing the hub door 1025 down on the catheter tube 150 also serves to compress the catheter tube 150 to a certain degree. The hub-based securement feature 1024 configured as the clamp including the hub door 1025 has a structural integrity and tensile strength sufficient to resist displacement of the catheter tube 150, once connected, under normal operating conditions, thereby providing a secure fluid-tight connection between the catheter tube 150 and the pair of cannulas 130 or 230 within the hub 1020.

Figure 11:
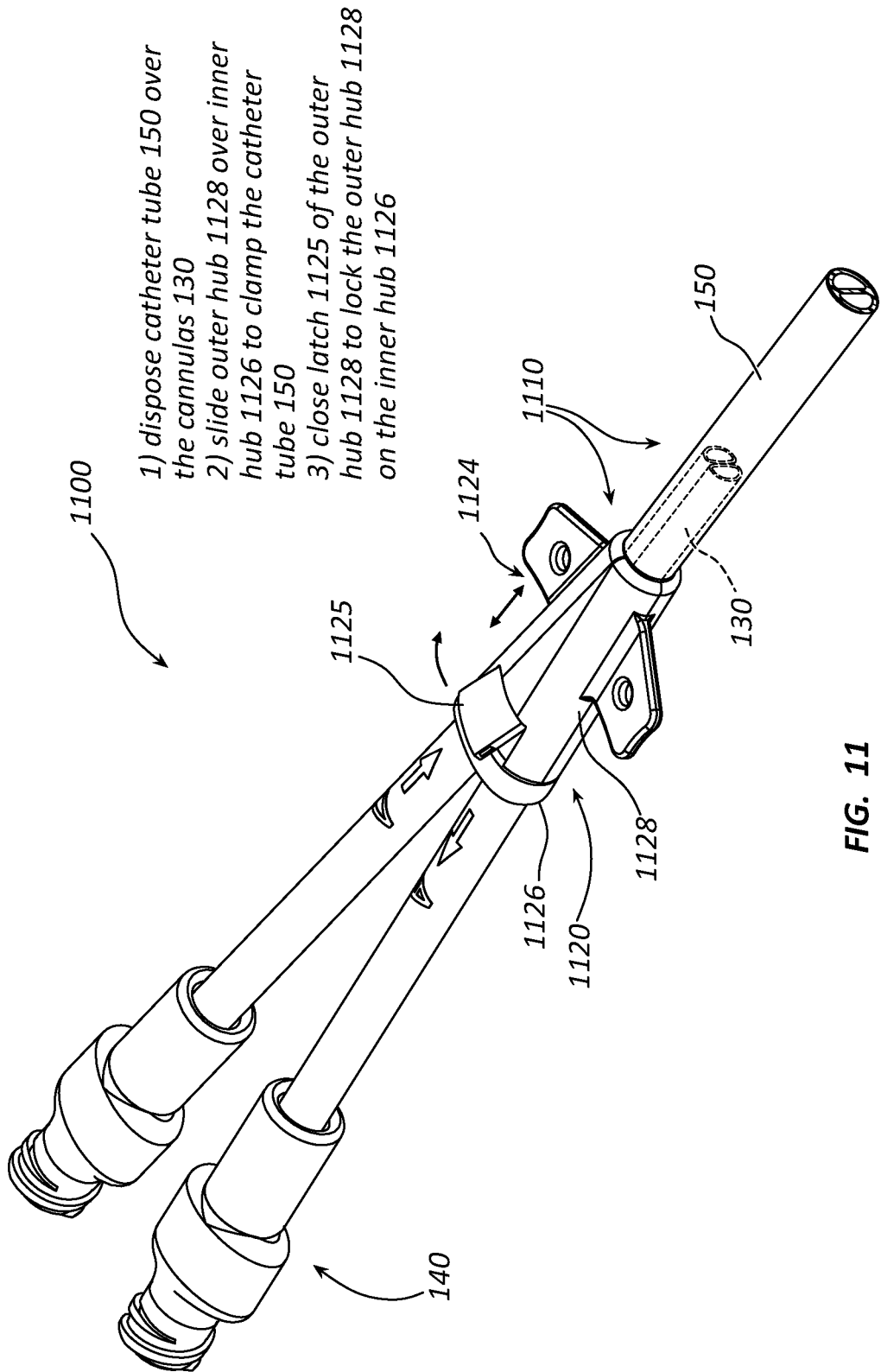
FIG. 11 illustrates a clamping-style hub for a ninth connection mechanism of a catheter assembly in accordance with some embodiments.

FIG. 11 illustrates a clamping-style hub 1120 for a ninth connection mechanism 1110 of a catheter assembly 1100 in accordance with some embodiments.

As shown, the connection mechanism 1110 of the catheter assembly 1100 includes a hub 1120 with a hub-based securement feature 1124 (not shown) configured as a slideable clamp. The hub-based securement feature 1124 can include a stationary inner hub 1126, a slideable outer hub 1128, and a latch 1125 on a hinge such as a living hinge at a proximal end portion of the outer hub 1128. While not shown, the hub-based securement feature 1124 can further include a catch at a proximal end portion of the inner hub 1126 to interlock with the latch 1125 of the outer hub 1128. Upon insertion of the catheter tube 150 over the pair of cannulas 130 or 230, the outer hub 1128 is configured to slide over the catheter tube 150 until stopped by the proximal end portion of the inner hub 1126, whereby the outer hub closes down on the catheter tube 150 around the pair of cannulas 130 or 230 and compresses the catheter tube 150 thereon. The latch 1125 of the outer hub 1128 is configured to interlock with the catch of the inner hub 1126 to lock the outer hub 1128 on the inner hub 1126. A lip around an opening of the hub 1120 formed by at least the outer hub 1128 (i.e., the opening configured to accommodate the catheter tube 150) can be configured with a textured surface to grip the catheter tube 150 when the outer hub 1128 is locked on the inner hub 1126 around the catheter tube 150. The hub-based securement feature 1124 configured as the slideable clamp has a structural integrity and tensile strength sufficient to resist displacement of the catheter tube 150, once connected, under normal operating conditions, thereby providing a secure fluid-tight connection between the catheter tube 150 and the pair of cannulas 130 or 230 within the hub 1120.

While the catheter tube 150 is shown in FIGS. 3A, 3B, 4, 5, 7, 8, 9, 10A, 10B, and 11 with a feature-free abluminal surface, the catheter tube 150 can have one or more interlocking catheter tube-based securement features such as a textured surface at a proximal end of the catheter tube 150 or the one or more circumferential barbs shown in FIGS. 6A and 6B.

2. Collared Connection Mechanisms

Collared connection mechanisms for catheter assemblies such as the catheter assembly 100 include, but are not limited to, connection mechanisms including hub-based securement features, catheter tube-based securement features, hub-based securement features with interlocking catheter tube-based securement features, or combinations thereof. As set forth herein, the hub-based and catheter tube-based securement features, which can also be considered hub-based and catheter tube-based securement devices, can further include features of their own. For example, a connection mechanism can include both hub-based and catheter tube-based securement features, wherein at least the hub-based securement feature or device is configured as a clamp, which in turn, includes arms of the clamp configured to close around a catheter tube.

a. Compression Sleeves as Collared Connection Mechanisms

Figure 12:
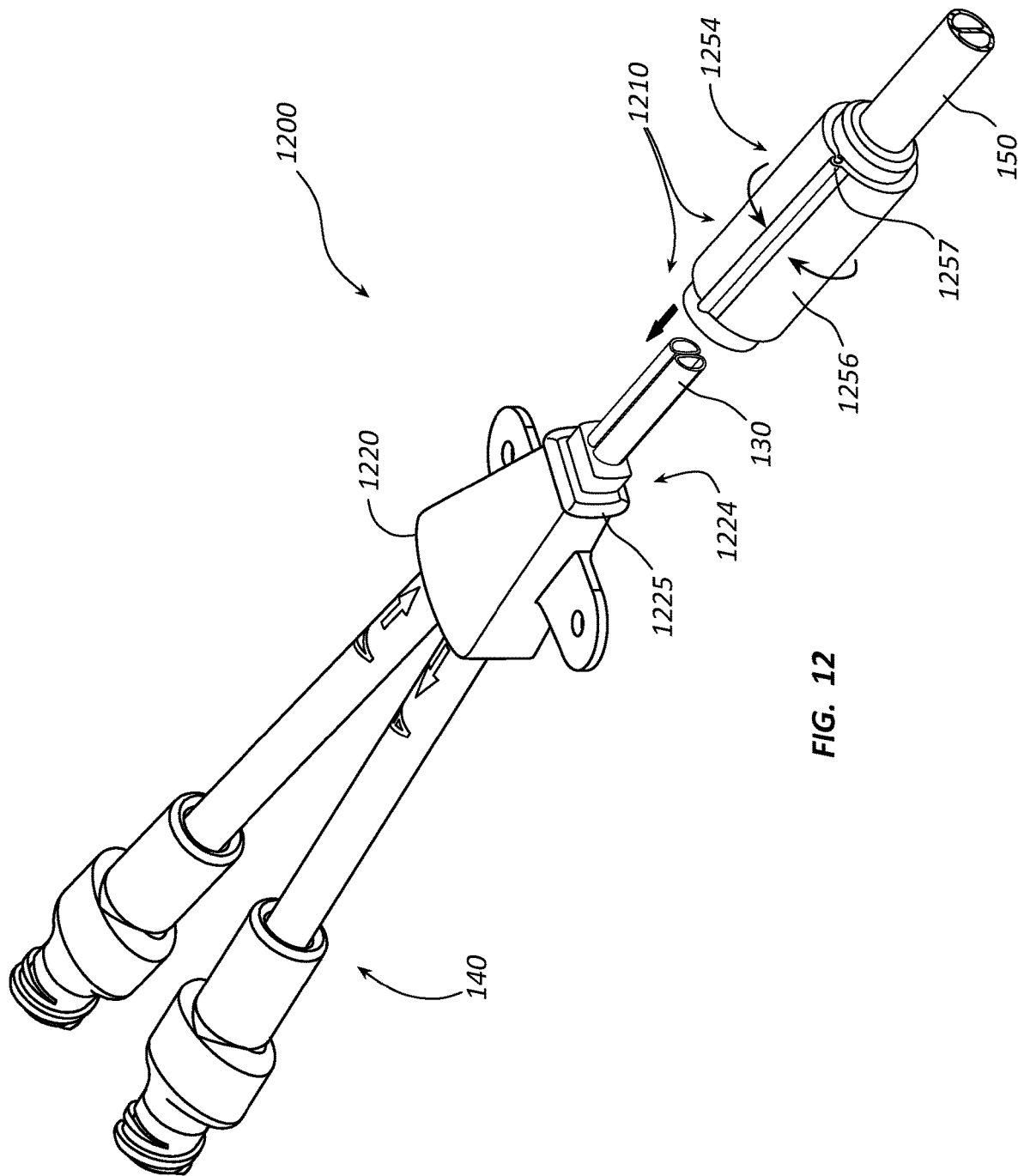
FIG. 12 illustrates a tenth connection mechanism of a catheter assembly in accordance with some embodiments.

FIG. 12 illustrates a tenth connection mechanism 1210 of a catheter assembly 1200 in accordance with some embodiments.

As shown, the connection mechanism 1210 of the catheter assembly 1200 includes the catheter tube 150 having a catheter tube-based securement feature 1254 configured as a compression sleeve 1256 for compressing the catheter tube 150 on the pair of cannulas 130 or 230. The compression sleeve 1256 can have a length commensurate with a length of the pair of cannulas 130 or 230 extending from a hub 1220 of the catheter assembly 1200, which length allows the compression sleeve 1256 to provide a compressive force over a greater area than a compression collar, thereby providing a greater total compressive force. The compression sleeve 1256 can include one or more fasteners such as a longitudinal snap 1257 configured to fasten end portions of the sleeve 1256 together along the longitudinal snap 1257 to produce the compressive force on the catheter tube 150 and, in turn, on the pair of cannulas 130 or 230 along the length of the pair of cannulas 130 or 230. Thus, the compression sleeve 1256 provides a secure fluid-tight connection between the catheter tube 150 and the pair of cannulas 130 or 230.

The connection mechanism 1210 of the catheter assembly 1200 can further include a hub-based securement feature 1224 configured as a receiver 1225 for a proximal end portion of the compression sleeve 1256, which protects at least the proximal end portion of the sleeve 1256 from unfastening once fastened and in position in the receiver 1225. In addition, the receiver 1225 can act as a stop when advancing a combination of the catheter tube 150 and the compression sleeve 1256 (unfastened) over the pair of cannulas 103 or 230.

b. Over-the-Hub Interlocking Collars

Figure 13:
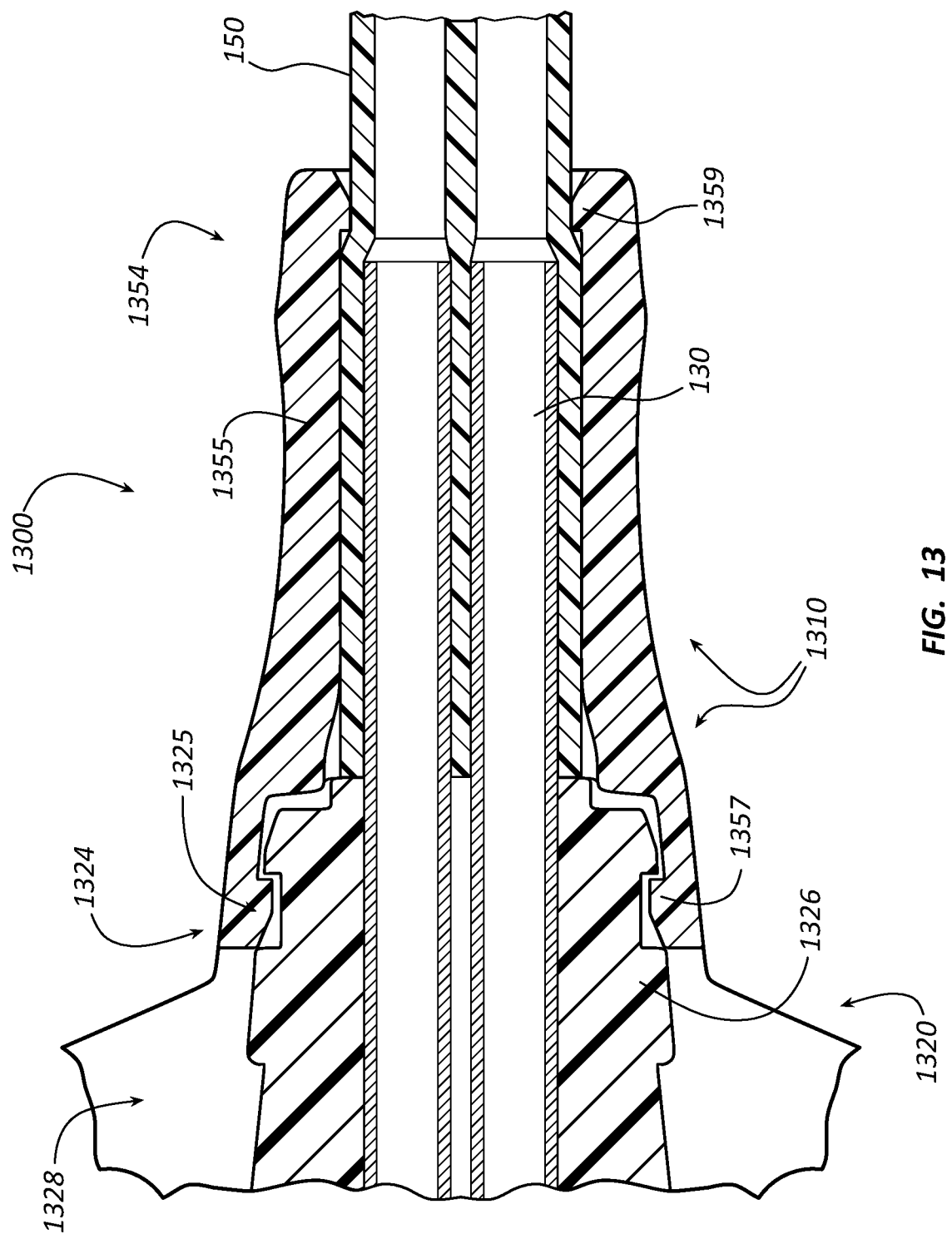
FIG. 13 illustrates an eleventh connection mechanism of a catheter assembly in accordance with some embodiments.

FIG. 13 illustrates an eleventh connection mechanism 1310 of a catheter assembly 1300 in accordance with some embodiments.

As shown, the connection mechanism 1310 of the catheter assembly 1300 includes a hub 1320 with a hub-based securement feature 1324 configured to interlock with a catheter tube-based securement feature 1354 over the catheter tube 150. The hub-based securement feature 1324 can include an inner hub 1326 and an outer hub 1328 molded over at least a portion of the inner hub 1326, wherein the inner hub 1326 can include one or more circumferential grooves such as circumferential groove 1325 in an outer surface of the inner hub 1326. The catheter tube-based securement feature 1354 can be configured as a collar 1355 through which the catheter tube 150 can pass, wherein the collar 1355 can be configured with one or more protrusions such as circumferential protrusion 1357 in an inner surface at a proximal end portion of the collar 1355 for interlocking with the one or more circumferential grooves of the inner hub 1326. The one or more protrusions in the inner surface at the proximal end portion of the collar 1355 can be, for example, a single circumferential protrusion such as the circumferential protrusion 1357 or two or more bump-type protrusions. In a proximal direction from a first protrusion of the one or more protrusions in the inner surface at the proximal end portion of the collar 1355, the inner surface of the collar 1355 can further include one or more circumferential grooves that alternate with the one or more protrusions. Such alternating protrusions and grooves are configured to interlock with one or more protrusions in the outer surface of the inner hub 1326 resulting from the one or more circumferential grooves in the outer surface of the inner hub 1326.

FIG. 13 shows a start of such a pattern. The collar 1355 can also be configured with one or more protrusions such as a circumferential protrusion 1359 in an inner surface at a distal end portion of the collar 1355 for interlocking with the pair of cannulas 130 or 230 under the catheter tube 150 at a location where each cannula of the pair of cannulas 130 or 230 steps down in diameter. Upon insertion of the catheter tube 150 over the pair of cannulas 130 or 230, the collar 1355 can be configured to slide over the catheter tube 150 until the collar 1355 interlocks with the inner hub 1326, whereby, due to the one or more protrusions in the inner surface at the distal end portion of the collar 1355, the collar 1355 closes down on the catheter tube 150 around the pair of cannulas 130 or 230 and compresses the catheter tube 150 thereon. The hub-based securement feature 1324 including the inner hub 1326 and the catheter tube-based securement feature 1354 including the collar 1355 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 14:
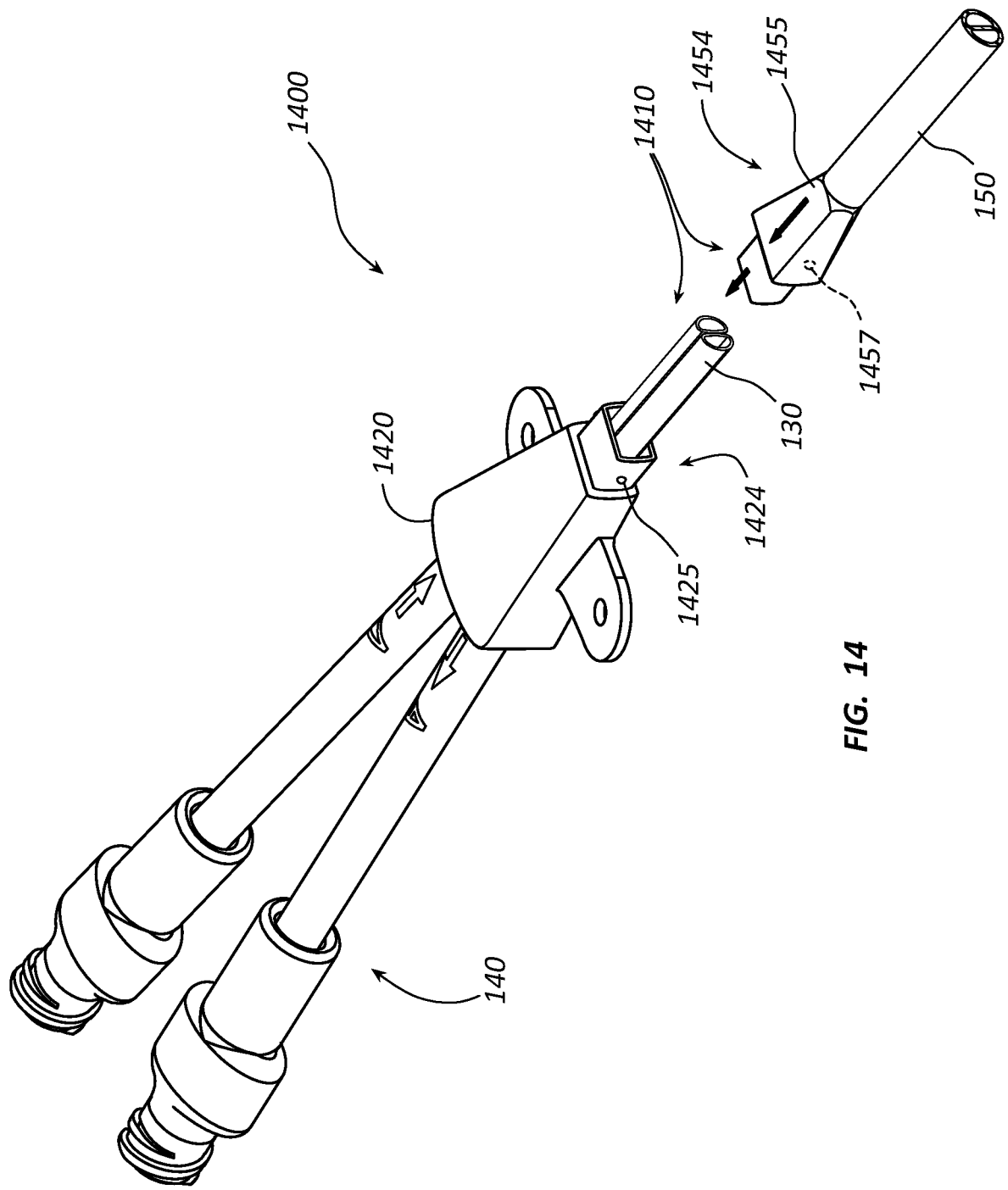
FIG. 14 illustrates a twelfth connection mechanism of a catheter assembly in accordance with some embodiments.

FIG. 14 illustrates a twelfth connection mechanism 1410 of a catheter assembly 1400 in accordance with some embodiments.

As shown, the connection mechanism 1410 of the catheter assembly 1400 includes a hub 1420 with a hub-based securement feature 1424 configured to interlock with a catheter tube-based securement feature 1454 over the catheter tube 150. The hub-based securement feature 1424 can include two or more protrusions 1425 in an outer surface of the hub 1420 such as the outer surface of an inner hub (see FIGS. 2A, 2B, and 13). The catheter tube-based securement feature 1454 can be configured as a collar 1455 through which the catheter tube 150 can pass, wherein the collar 1455 can be configured with one or more indentations 1457 in an inner surface (or one or more holes therethrough) at a proximal end portion of the collar 1455 for interlocking with the two or more protrusions 1425 in the outer surface of the hub 1420. While not shown, the collar 1455 can be further configured with one or more protrusions such as a circumferential protrusion in an inner surface at a distal end portion of the collar 1455 for interlocking with the pair of cannulas 130 or 230 under the catheter tube 150 at a location where each cannula of the pair of cannulas 130 or 230 steps down in diameter (see FIG. 13). Upon insertion of the catheter tube 150 over the pair of cannulas 130 or 230, the collar 1455 can be configured to slide over the catheter tube 150 until the collar 1455 interlocks with the hub 1420, whereby, due to a narrowing inner diameter of the collar 1455 or the one or more protrusions in the inner surface at the distal end portion of the collar 1455, the collar 1455 closes down on the catheter tube 150 around the pair of cannulas 130 or 230 and compresses the catheter tube 150 thereon. The hub-based securement feature 1424 including the inner hub and the catheter tube-based securement feature 1454 including the collar 1455 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 15:
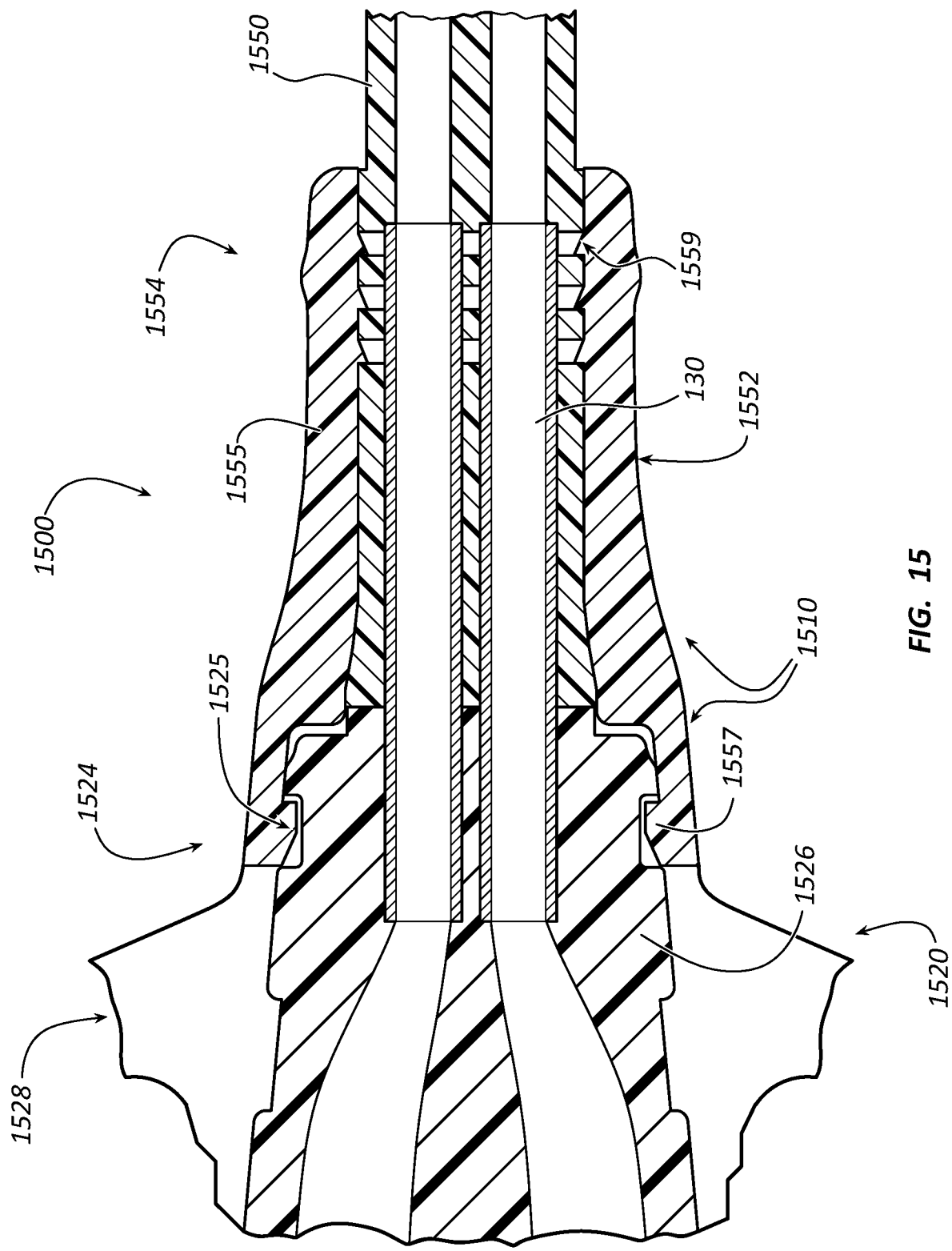
FIG. 15 illustrates a thirteenth connection mechanism of a catheter assembly in accordance with some embodiments.

FIG. 15 illustrates a thirteenth connection mechanism 1510 of a catheter assembly 1500 in accordance with some embodiments.

As shown, the connection mechanism 1510 of the catheter assembly 1500 includes a hub 1520 with a hub-based securement feature 1524 configured to interlock with a catheter tube-based securement feature 1554 over a catheter tube 1550. The hub-based securement feature 1524 can include an inner hub 1526 and an outer hub 1528 molded over at least a portion of the inner hub 1526, wherein the inner hub 1526 can include one or more circumferential grooves such as circumferential groove 1525 in an outer surface of the inner hub 1526. The catheter tube-based securement feature 1554 can be configured as a collar 1555 through which the catheter 1550 can pass, wherein the collar 1555 can be configured with one or more protrusions such as a circumferential protrusion 1557 in an inner surface at a proximal end portion of the collar 1555 for interlocking with the one or more circumferential grooves of the inner hub 1526. The one or more protrusions in the inner surface at the proximal end portion of the collar 1555 can be, for example, a single circumferential protrusion such as the circumferential protrusion 1557 or two or more bump-type protrusions. In a distal end portion of the collar 1555, the inner surface of the collar 1555 can further include one or more circumferential grooves 1559 configured to interlock with another catheter tube-based securement feature 1554 including one or more protrusions 1552 in an outer surface of the catheter tube 1550. Upon insertion of the catheter tube 1550 over the pair of cannulas 130 or 230, the collar 1555 can be configured to slide over the catheter tube 1550 until the collar 1555 interlocks with the inner hub 1526 and the catheter tube 1550. The hub-based securement feature 1524 including the inner hub 1526 and the catheter tube-based securement feature 1554 including the collar 1555 can be further configured with a structural integrity (e.g., thickness, durometer, etc.) and tensile strength sufficient to resist displacement of the catheter tube 1550, once connected, under normal operating conditions, thereby providing a secure fluid-tight connection between the catheter tube 1550 and the pair of cannulas 130 or 230.

FIG. 16A illustrates a fourteenth connection mechanism 1610 of a catheter assembly 1600 in accordance with some embodiments. FIG. 16B illustrates a hub-based securement feature 1624 of the fourteenth connection mechanism in accordance with some embodiments. FIG. 16C illustrates a close-up of the fourteenth connection mechanism 1610 of the catheter assembly 1600 in accordance with some embodiments.

As shown, the connection mechanism 1610 of the catheter assembly 1600 includes a hub 1620 with the hub-based securement feature 1624 configured to interlock with a catheter tube-based securement feature 1654 over the catheter tube 150. The hub-based securement feature 1624 can include an inner hub 1626 and an outer hub 1628 (not shown) molded over at least a portion of the inner hub 1626, wherein the inner hub 1626 can include a threaded portion in an outer surface of the inner hub 1626 (i.e., external threads). In addition, the threaded portion of the inner hub 1626 can include 2-4 longitudinal slits through the threaded portion of the inner hub 1626 as exemplified by longitudinal slit 1627, which 2-4 longitudinal slits divides the threaded portion of the inner hub 1626 into a corresponding 2-4 compressible pieces. The catheter tube-based securement feature 1654 can be configured as a collar 1655 through which the catheter tube 150 can pass, wherein the collar 1655 can include a threaded portion in an inner surface of the collar 1655 (i.e., internal threads) for interlocking with the threaded portion of the inner hub 1626. Furthermore, the collar 1655 can have a slightly smaller inner diameter than an outer diameter of the threaded portion of the inner hub 1626, thereby providing differential diameters. Upon insertion of the catheter tube 150 over the pair of cannulas 130 or 230, the collar 1655 can be configured to slide over the catheter tube 150 until the collar 1655 can be screwed onto the threaded portion of the inner hub 1626. Due to the longitudinal slits and the differential diameters, the action of screwing the collar 1655 onto the threaded portion of the inner hub 1626 compresses the compressible pieces onto a rubber ring or sleeve 1629 (see FIG. 16B), which, in turn, compresses the catheter tube 150 on the pair of cannulas 130 or 230. The hub-based securement feature 1624 including the inner hub 1626 and the catheter tube-based securement feature 1654 including the collar 1655 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

c. Hub-Based Interlocking Arms

Figure 17:
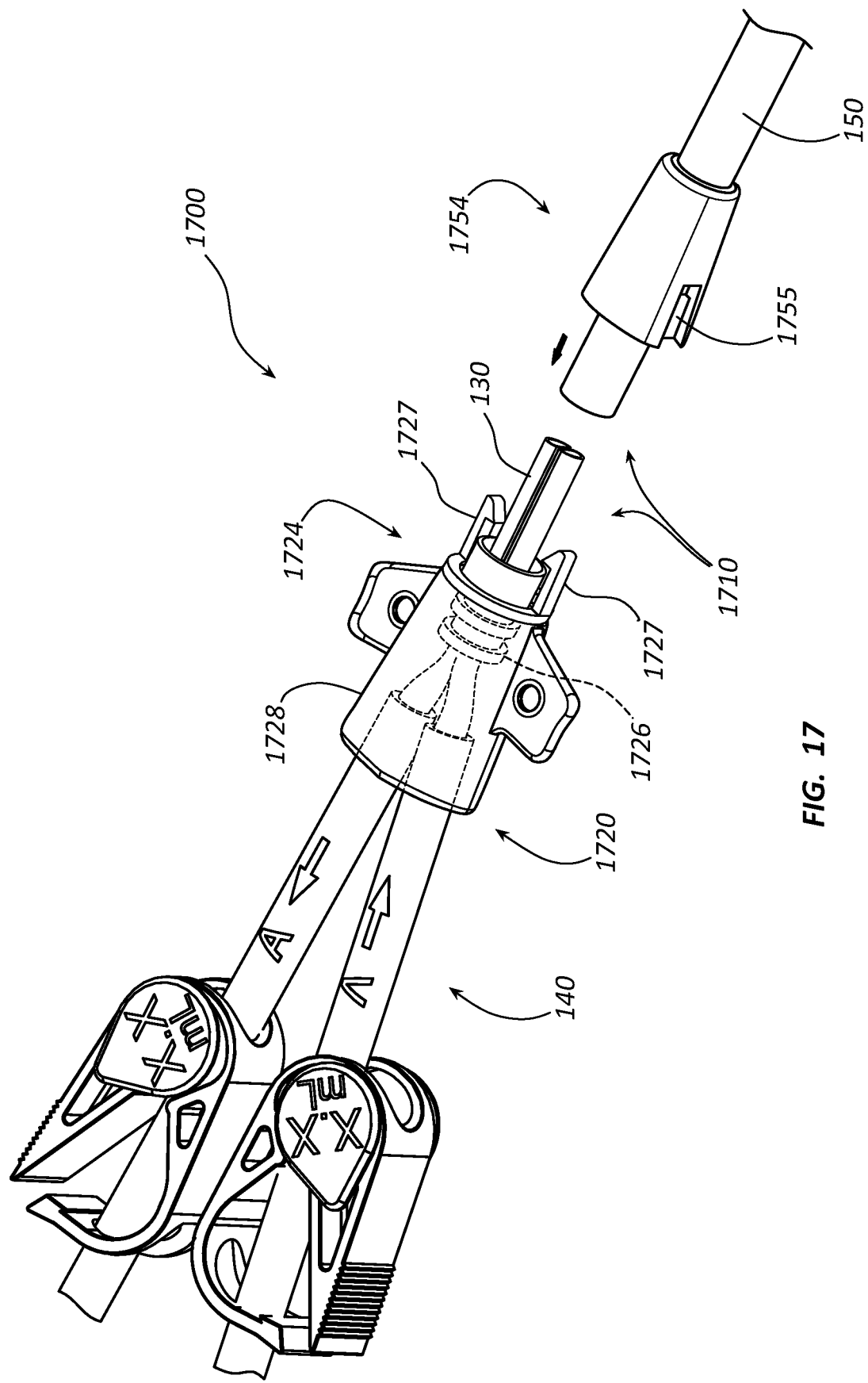
FIG. 17 illustrates a fifteenth connection mechanism of a catheter assembly in accordance with some embodiments.

FIG. 17 illustrates a fourteenth connection mechanism 1710 of a catheter assembly 1700 in accordance with some embodiments.

As shown, the connection mechanism 1710 of the catheter assembly 1700 includes a hub 1720 with the hub-based securement feature 1724 configured to interlock with a catheter tube-based securement feature 1754 over the catheter tube 150. The hub-based securement feature 1724 can include an inner hub 1726 and an outer hub 1728 molded over at least a portion of the inner hub 1726, wherein the inner hub 1726 can include a pair of interlocking arms 1727 extending from the inner hub 1726. Each interlocking arm of the pair of interlocking arms 1727 extends from a side of the inner hub 1726. The catheter tube-based securement feature 1754 can be configured as a collar 1755 through which the catheter tube 150 can pass, wherein the collar 1755 can include a pair of receiving slots in an outer surface of the collar 1755 for interlocking with the interlocking arms 1727 of the inner hub 1726. Each receiving slot (see receiving slot 1755) of the pair of receiving slots is disposed in a side of the collar 1755. Upon insertion of the catheter tube 150 over the pair of cannulas 130 or 230, the collar 1755 can be configured to slide over the catheter tube 150 until the interlocking arms 1727 can be seated and locked in the receiving slots of the collar 1755. Due to a narrowing inner diameter of the collar 1755, the collar 1755 closes down on the catheter tube 150 around the pair of cannulas 130 or 230 and compresses the catheter tube 150 thereon. The hub-based securement feature 1724 including the inner hub 1726 and the catheter tube-based securement feature 1754 including the collar 1755 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

d. Collar-Based Interlocking Arms

FIG. 18A illustrates a sixteenth connection mechanism 1810 of a catheter assembly 1800 in accordance with some embodiments. FIG. 18B illustrates a fastener 1859 of a catheter tube-based securement feature 1854 of the sixteenth connection mechanism in accordance with some embodiments.

As shown, the connection mechanism 1810 of the catheter assembly 1800 includes a hub 1820 with the hub-based securement feature 1824 configured to interlock with the catheter tube-based securement feature 1854 over the catheter tube 150. The hub-based securement feature 1824 can include a pair of receiving slots in an outer surface of the hub 1820. Each receiving slot (see receiving slot 1827) of the pair of receiving slots can be disposed in a side of the hub 1820. The catheter tube-based securement feature 1854 can be configured as a collar 1855 through which the catheter tube 150 can pass, wherein the collar 1855 can include a pair of interlocking arms 1857 extending from the collar 1855 for interlocking with the receiving slots of the hub 1820. Each interlocking arm of the pair of interlocking arms 1857 can extend from a side of the collar 1855, and the collar 1855 can be fastened onto the catheter tube 150 with one or more fasteners such as the fastener 1859, which includes a clasp as shown. With the collar 1855 at least loosely fastened onto the catheter tube 150, the catheter tube 150 can be disposed over the pair of cannulas 130 or 230, and the collar 1855 can be advanced over the hub 1820 until the interlocking arms 1857 are seated and locked in the receiving slots of the hub 1820. Due to the collar 1855 being at least loosely fastened onto the catheter tube 150 upon disposal of the catheter tube 150 over the pair of cannulas 130 or 230, the clasp of the collar 1855 can be subsequently closed down on the catheter tube 150 around the pair of cannulas 130 or 230 to compress the catheter tube 150 thereon. The hub-based securement feature 1824 including the hub 1820 and the catheter tube-based securement feature 1854 including the collar 1855 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 19A:
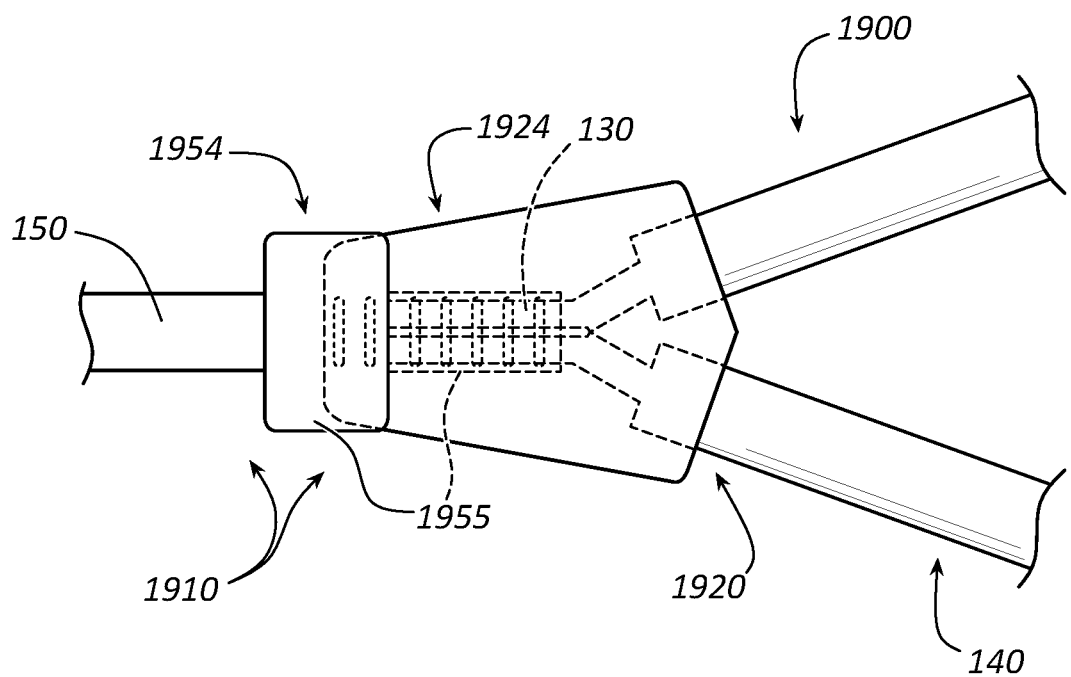
FIG. 19A illustrates a seventeenth connection mechanism of a catheter assembly in accordance with some embodiments.
Figure 19B:
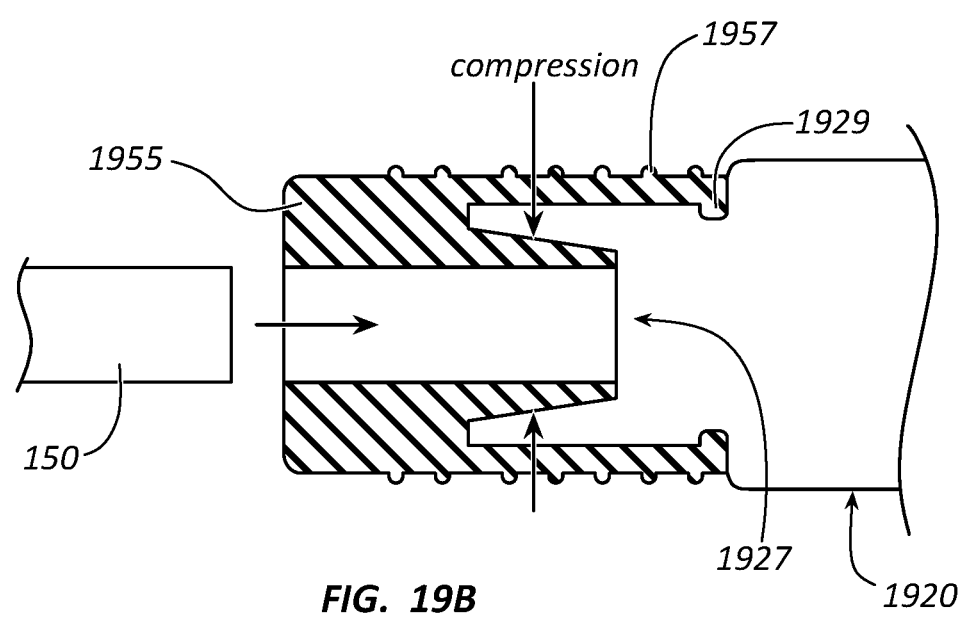
FIG. 19B illustrates a locking arm engaged with a receiving slot of the seventeenth connection mechanism in accordance with some embodiments.

FIG. 19A illustrates a seventeenth connection mechanism 1910 of a catheter assembly 1900 in accordance with some embodiments. FIG. 19B illustrates a locking arm 1957 engaged with a receiving slot 1927 of the seventeenth connection mechanism 1910 in accordance with some embodiments.

As shown, the connection mechanism 1910 of the catheter assembly 1900 includes a hub 1920 with a hub-based securement feature 1924 configured to interlock with a catheter tube-based securement feature 1954 over the catheter tube 150. The hub-based securement feature 1924 can include a receiving slot 1927 in an outer surface of the hub 1920 such as in an outer surface of an inner hub (see FIGS. 2A and 2B). The receiving slot 1927 can be disposed in a top of the hub 1920, a bottom of the hub 1920, or both the top and bottom of the hub 1920. The catheter tube-based securement feature 1954 can be configured as a collar 1955 through which the catheter tube 150 can pass, wherein the collar 1955 can include an interlocking arm 1957 for interlocking with the receiving slot 1927 in the top of the hub 1920 or the bottom of the hub 1920 depending upon the location of the receiving slot 1927. Alternatively, the collar 1955 can include a pair of interlocking arms, each of which can be identical to the locking arm 1957 (for symmetry and ease of use), wherein the pair of interlocking arms are configured to interlock with the receiving slot 1927 when the receiving slot 1927 occupies both the top of the hub 1920 and the bottom of the hub 1920. Alternatively, the collar 1955 can be configured as a partial-collar insert configured to be inserted into the receiving slot 1927 in the top of the hub 1920 or the bottom of the hub 1920 depending upon the location of the receiving slot 1927.

The partial-collar insert can be disposed in the receiving slot 1927 adjacent to the catheter tube 150 once the catheter tube 150 is disposed over the pair of cannulas 130 or 230. Two of such partial-collar inserts can be combined for a full-type collar like the collar 1955, wherein a top partial-collar insert is configured to be inserted into the receiving slot 1927 in the top of the hub 1920 and a bottom partial-collar insert is configured to be inserted into the receiving slot 1927 in the bottom of the hub 1920. Regardless of the configuration of the collar 1955, each locking arm exemplified by the locking arm 1957 includes a portion of a fastener 1929 (e.g., a snap) configured to interlock with another portion of the fastener on the hub 1920 as shown. Once the catheter tube 150 is disposed over the pair of cannulas 130 or 230, the collar 1955, or a partial-collar insert thereof, can be advanced across the catheter tube 150 and the hub 1920 until the seated and locked with the hub 1920, thereby compressing the catheter tube 150 on the pair of cannulas 130 or 230. The hub-based securement feature 1924 including the hub 1920 and the catheter tube-based securement feature 1954 including the collar 1955 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

e. Collet-Type: Hub-Based Receivers

Figure 20A:
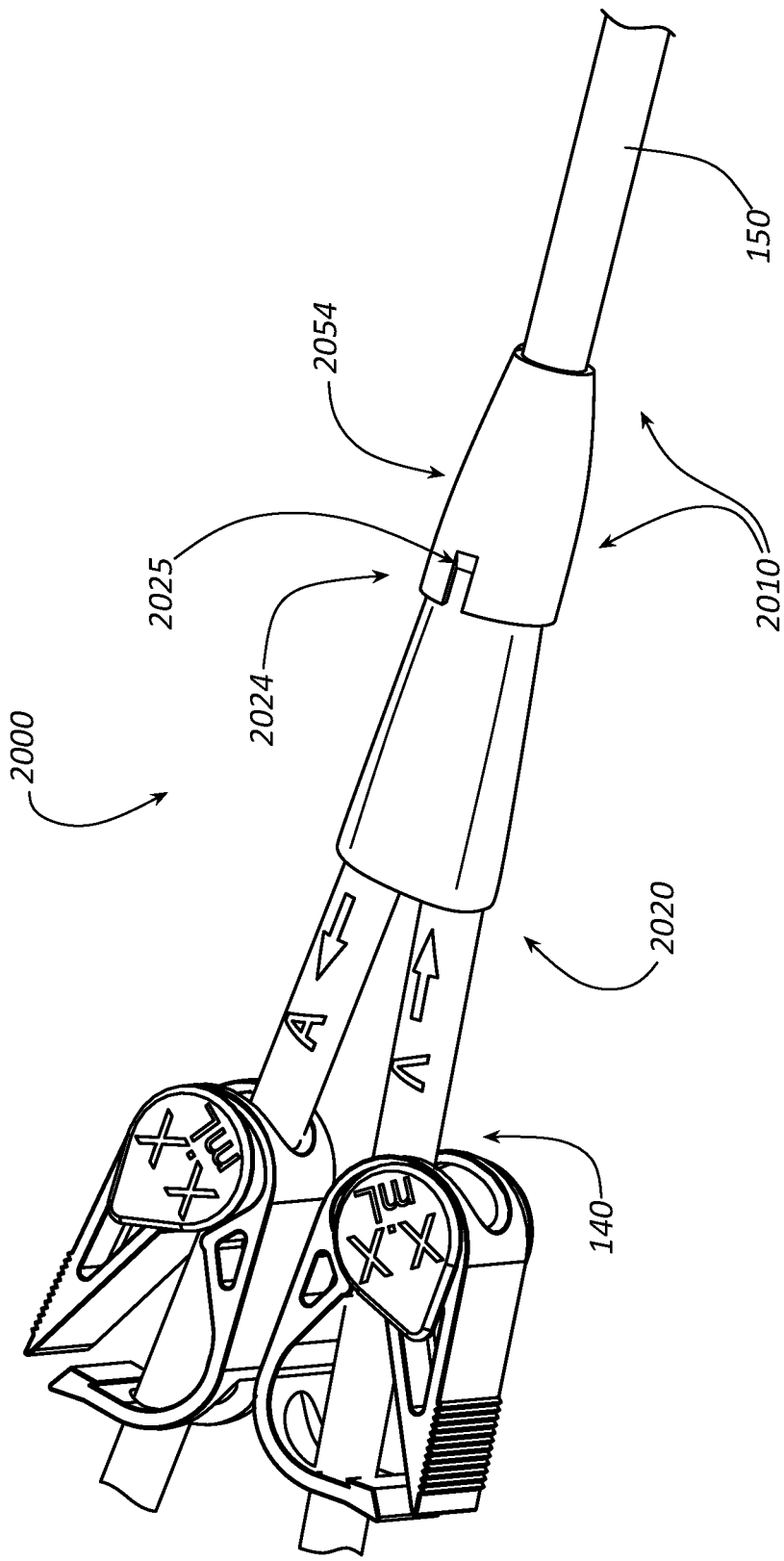
FIG. 20A illustrates an eighteenth connection mechanism of a catheter assembly in accordance with some embodiments.
Figure 20B:
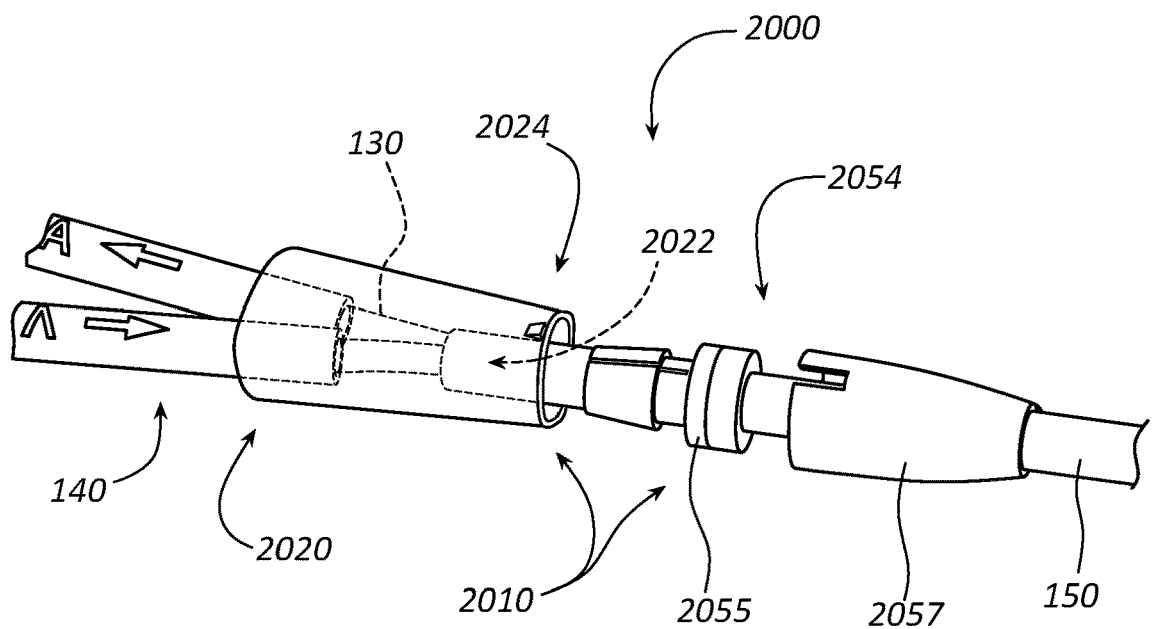
FIG. 20B illustrates another view of the eighteenth connection mechanism of the catheter assembly of FIG. 20A.
Figure 20C:
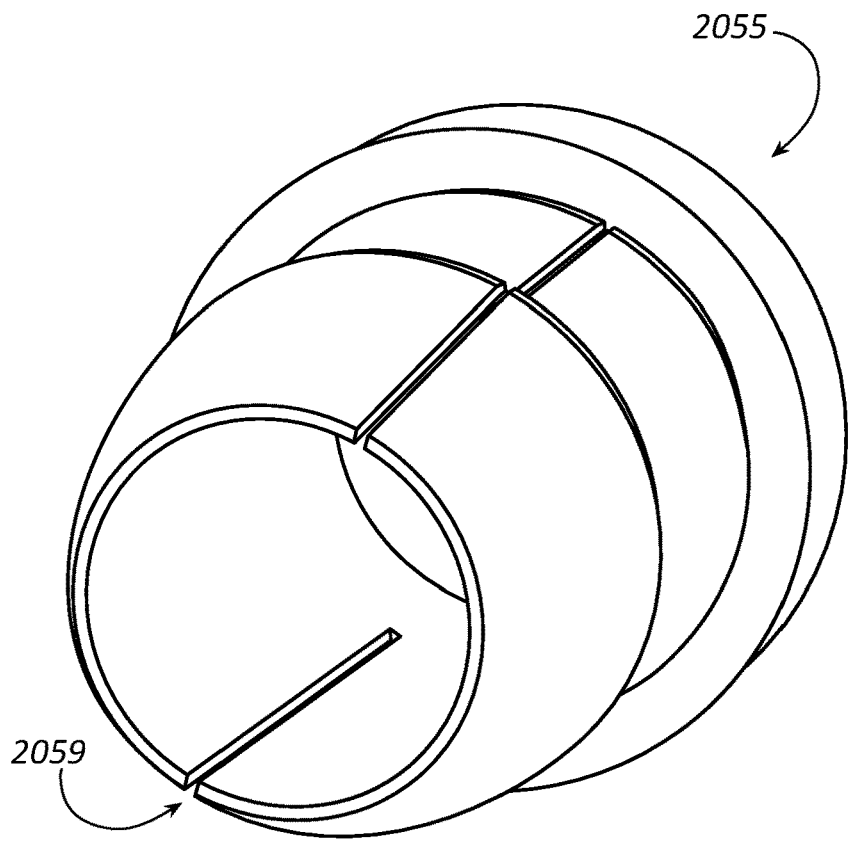
FIG. 20C illustrates a collet proper of the eighteenth connection mechanism in accordance with some embodiments.

FIGS. 20A and 20B illustrate an eighteenth connection mechanism 2010 of a catheter assembly 2000 in accordance with some embodiments. FIG. 20C illustrates a collet proper 2055 of the eighteenth connection mechanism 2010 in accordance with some embodiments.

As shown, the connection mechanism 2010 of the catheter assembly 2000 includes a hub 2020 with a hub-based securement feature 2024 configured to interlock with a catheter tube-based securement feature 2054 over the catheter tube 150. The hub-based securement feature 2024 can include a bore 2022 in the hub 2020, wherein the bore 2022 is configured with a taper in which a diameter of the bore 2022 is greater at a distal end of the bore 2022 than the diameter of the bore 2022 at a proximal end of the bore 2022. With such a taper, the bore 2022 can function as a receiver for the collet proper 2055. The catheter tube-based securement feature 2054 can include the collet proper 2055 and a collet cap 2057 through both of which the catheter tube 150 can pass. The collet proper 2055 can include 2-4 longitudinal slits through a side wall of the collet proper 2055 as exemplified by longitudinal slit 2059. The 2-4 longitudinal slits divide the side wall of the collet proper 2055 into a corresponding 2-4 compressible pieces that are configured to be compressed by the taper of the bore 2022 when the collet proper 2055 is inserted therein.

Upon insertion of the catheter tube 150 over the pair of cannulas 130 or 230, the collet proper 2055 can be configured to slide over the catheter tube 150 until the collet proper 2055 is completely seated in the bore 2022, whereby, due to the taper of the bore 2022, the 2-4 compressible pieces of the collet proper 2050 close down on the catheter tube 150 around the pair of cannulas 130 or 230 and compresses the catheter tube 150 thereon. Between the collet cap 2057 and the hub 2020 are one or more fasteners such as fastener 2025 (e.g., a protrusion on an outer surface of the hub 2020 and a groove in a side wall of the collet cap 2057 to capture the protrusion) configured to lock the resulting three-piece collet together. The hub-based securement feature 2024 including the hub 2020 and the catheter tube-based securement feature 2054 including the collet proper 2055 and the collet cap 2057 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 21C:
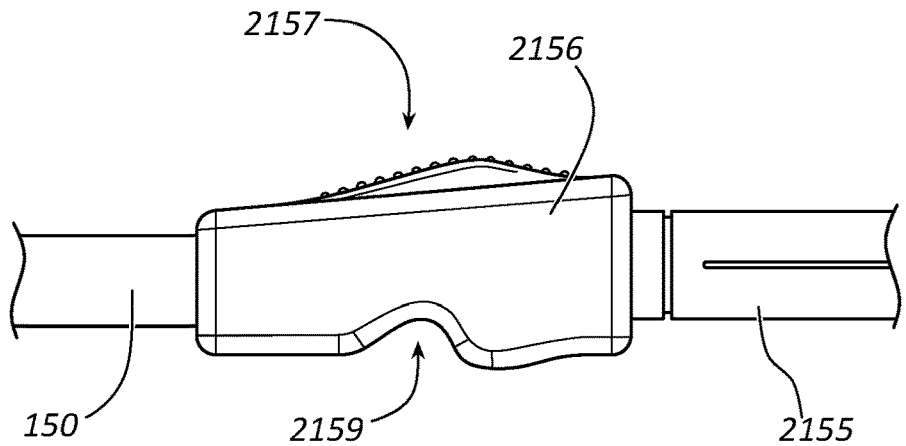
FIG. 21C illustrates a side view of an extension for the collet proper of the nineteenth connection mechanism in accordance with some embodiments.
Figure 21D:
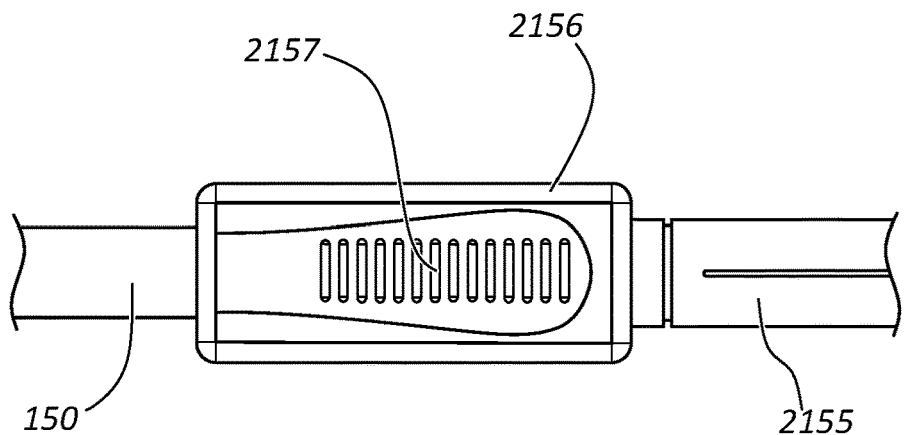
FIG. 21D illustrates a top view of the extension for the collet proper of the nineteenth connection mechanism in accordance with some embodiments.
Figure 21E:
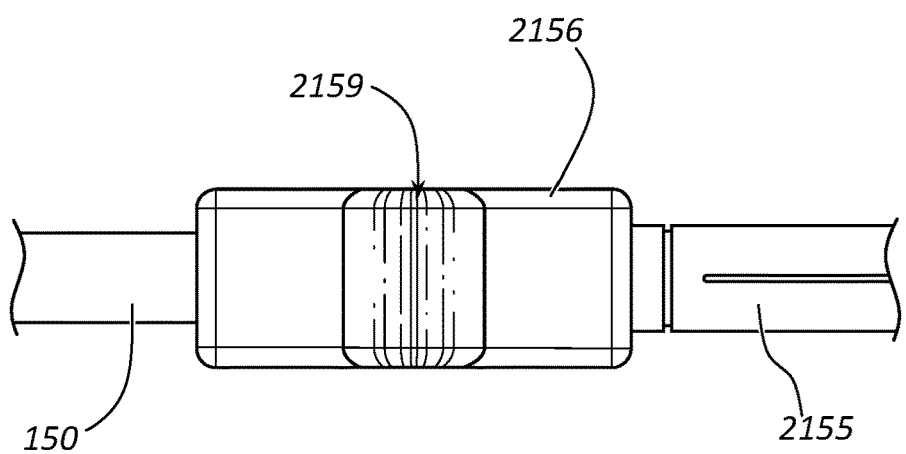
FIG. 21E illustrates a bottom view of an extension for the collet proper of the nineteenth connection mechanism in accordance with some embodiments.

FIG. 21A illustrates a nineteenth connection mechanism 2110 of a catheter assembly 2100 in accordance with some embodiments. FIG. 21B illustrates a collet proper 2155 of the nineteenth connection mechanism 2110 in accordance with some embodiments. FIG. 21C illustrates a side view of an extension 2156 for the collet proper 2155 of the nineteenth connection mechanism 2110 in accordance with some embodiments, whereas FIGS. 21D and 21E respectively illustrate top and bottom views of the extension 2156 for the collet proper 2155.

As shown, the connection mechanism 2110 of the catheter assembly 2100 includes a hub 2120 with a hub-based securement feature 2124 configured to interlock with a catheter tube-based securement feature 2154 over the catheter tube 150. The hub-based securement feature 2124 can include a bore 2122 in the hub 2120, wherein the bore 2122 is configured with a taper in which a diameter of the bore 2122 is greater at a distal end of the bore 2122 than the diameter of the bore 2122 at a proximal end of the bore 2122. With such a taper, the bore 2122 can function as a receiver for the collet proper 2155. The catheter tube-based securement feature 2154 can include the collet proper 2155 through which the catheter tube 150 can pass. The collet proper 2155 can include 2-4 longitudinal slits through a side wall of the collet proper 2155 as exemplified by longitudinal slit 2153. The 2-4 longitudinal slits divide the side wall of the collet proper 2155 into a corresponding 2-4 compressible pieces that are configured to be compressed by the taper of the bore 2122 when the collet proper 2155 is inserted therein. To better manipulate the collet proper 2155, the collet proper 2155 can further include the extension 2156. The extension 2156—as with any component set forth herein configured for direct handling—can include one or more handling features including, but not limited to, a thumb grip 2157, a finger indentation 2159, or both to further better manipulate the collet proper 2155. Upon insertion of the catheter tube 150 over the pair of cannulas 130 or 230, the collet proper 2155 can be configured to slide over the catheter tube 150 until the collet proper 2155 is completely seated in the bore 2122, whereby, due to the taper of the bore 2122, the 2-4 compressible pieces of the collet proper 2155 close down on the catheter tube 150 around the pair of cannulas 130 or 230 and compresses the catheter tube 150 thereon. Between the hub 2120 and the collet proper 2125 are one or more fasteners such as fastener 2125, which can be a combination of i) one or more protrusions such as two or more bumps or one circumferential protrusion of an inner surface of the bore 2122 with ii) one or more circumferential grooves in an outer surface of the collet proper 2155 configured to lock the resulting two-piece collet together. Alternatively, the fastener 2125 can have an opposite orientation than the foregoing; that is, the fastener 2125 can be a combination of one or more protrusions such as two or more bumps or one circumferential protrusion of an outer surface of the collet proper 2155 with one or more circumferential grooves in an inner surface of the bore 2122 configured to lock the resulting two-piece collet together. The hub-based securement feature 2124 including the hub 2120 and the catheter tube-based securement feature 2154 including the collet proper 2155 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 22A:
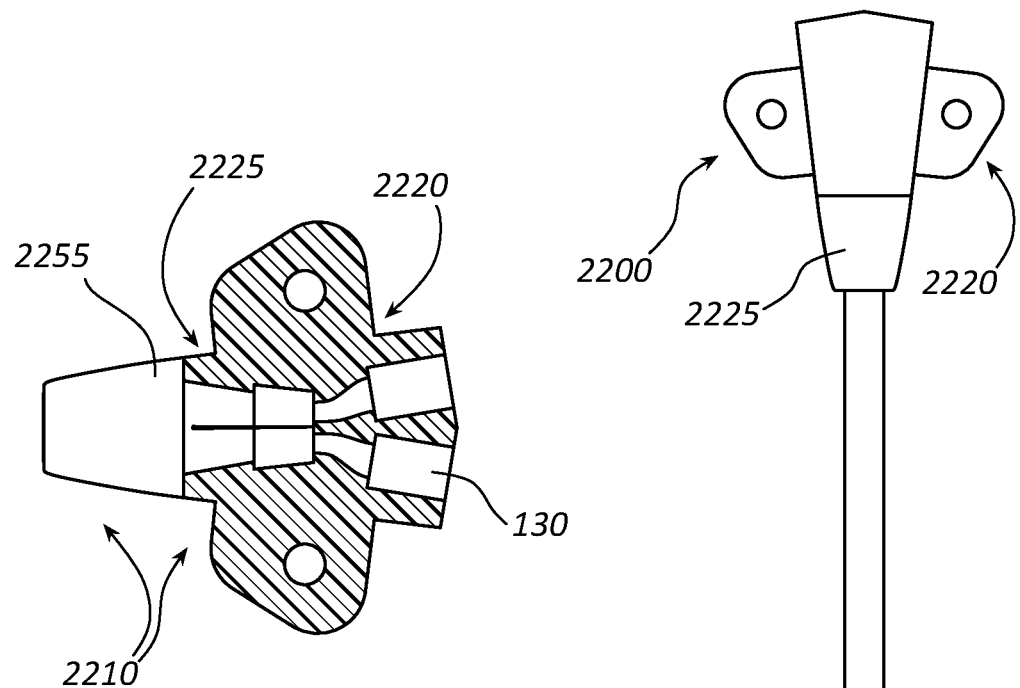
FIG. 22A illustrates a top cross-sectional view of a twentieth connection mechanism in accordance with some embodiments.
Figure 22B:
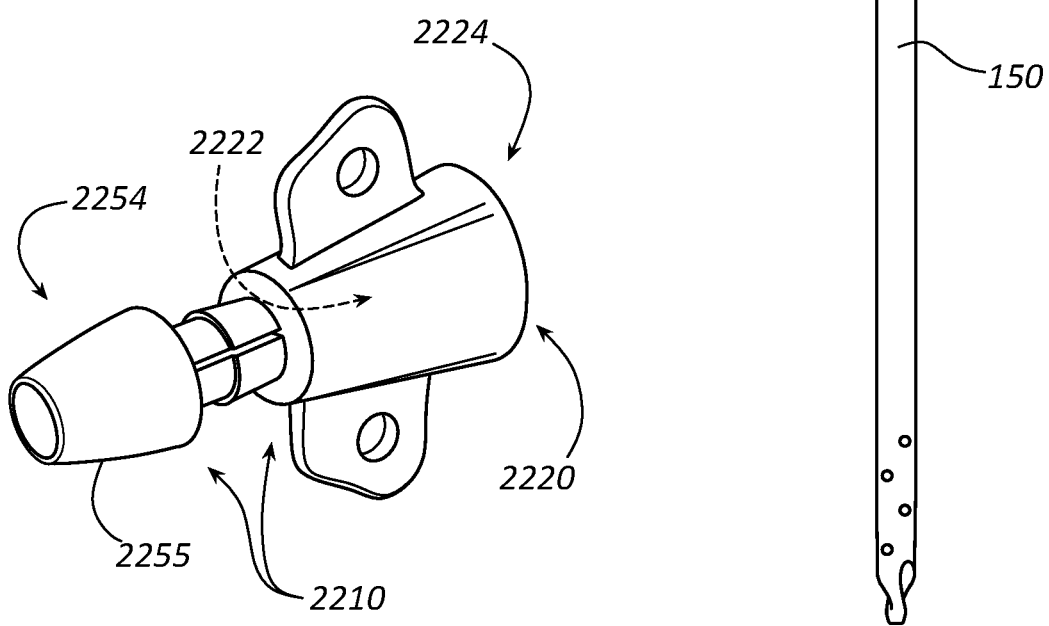
FIG. 22B illustrates a perspective view of the twentieth connection mechanism in accordance with some embodiments.
Figure 22C:
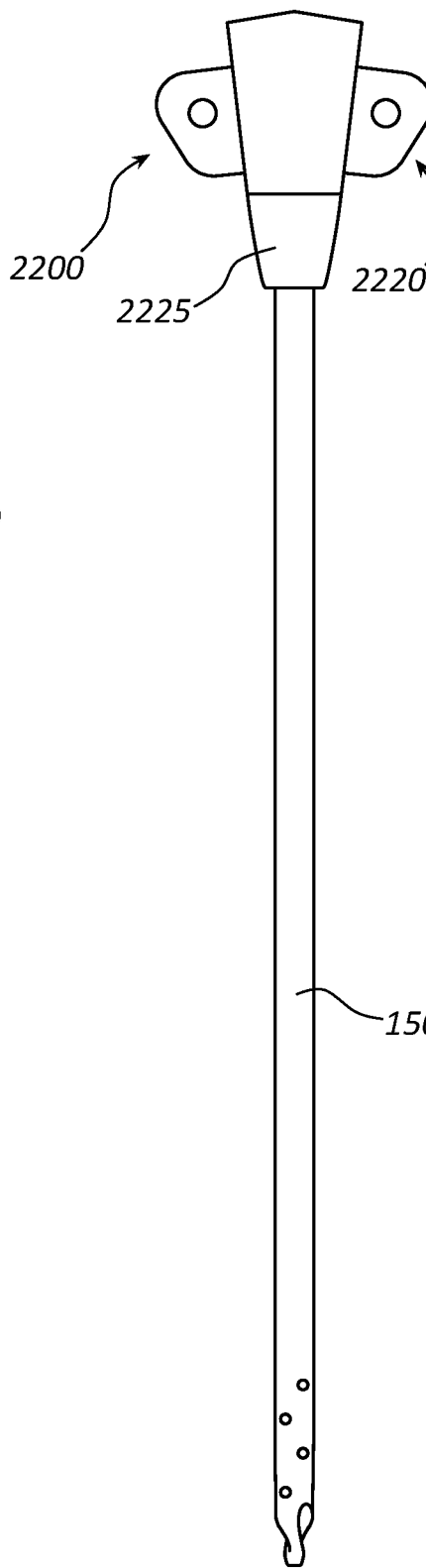
FIG. 22C illustrates the twentieth connection mechanism of as part of a catheter assembly in accordance with some embodiments.

FIG. 22A illustrates a top cross-sectional view of a twentieth connection mechanism 2210 in accordance with some embodiments. FIG. 22B illustrates a perspective view of the twentieth connection mechanism 2210 in accordance with some embodiments. FIG. 22C illustrates the twentieth connection mechanism 2210 of as part of a catheter assembly 2200 in accordance with some embodiments.

As shown, the connection mechanism 2210 of the catheter assembly 2200 is similar to the connection mechanism 2110 of the catheter assembly 2100 in that the connection mechanism 2210 includes a hub 2220 with a hub-based securement feature 2224 configured to interlock with a catheter tube-based securement feature 2254 over the catheter tube 150. The hub-based securement feature 2224 can likewise include a bore 2222 in the hub 2220, wherein the bore 2222 is configured with a taper in which a diameter of the bore 2222 is greater at a distal end of the bore 2222 than the diameter of the bore 2222 at a proximal end of the bore 2222. With such a taper, the bore 2222 can also function as a receiver for a collet proper 2255. The catheter tube-based securement feature 2254 can likewise include the collet proper 2255 through which the catheter tube 150 can pass. The collet proper 2255 can optionally include 2-4 longitudinal slits through a side wall of the collet proper 2255 but need not include such longitudinal slits like the collet proper 2155 of the connection mechanism 2110. This is because the collet proper 2255 can have a lower durometer than at least a portion of the hub 2220 including the bore 2222. (The connection mechanism 2110 of the catheter assembly 2100 can also feature a difference in durometers.) Between the hub 2220 and the collet proper 2225 are one or more fasteners such as fastener 2225, which can be a combination of i) a relatively wide circumferential protrusion of an inner surface of the bore 2222 with ii) a relatively wide circumferential groove in an outer surface of the collet proper 2255 configured to lock the resulting two-piece collet together.

The relatively wide circumferential protrusion and the relatively wide circumferential groove, as compared to the relatively narrow fastener 2125 of the connection mechanism 2110, provides a deep seat for the collet proper 2225 in the bore 2222 that is easy to find by feel. Upon insertion of the catheter tube 150 over the pair of cannulas 130 or 230, the collet proper 2255 can be configured to slide over the catheter tube 150 until the collet proper 2255 is completely seated in the bore 2222, whereby, due to the taper of the bore 2222 and a difference in durometers, the collet proper 2255 closes down on the catheter tube 150 around the pair of cannulas 130 or 230 and compresses the catheter tube 150 thereon. The hub-based securement feature 2224 including the hub 2220 and the catheter tube-based securement feature 2254 including the collet proper 2255 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 23A:
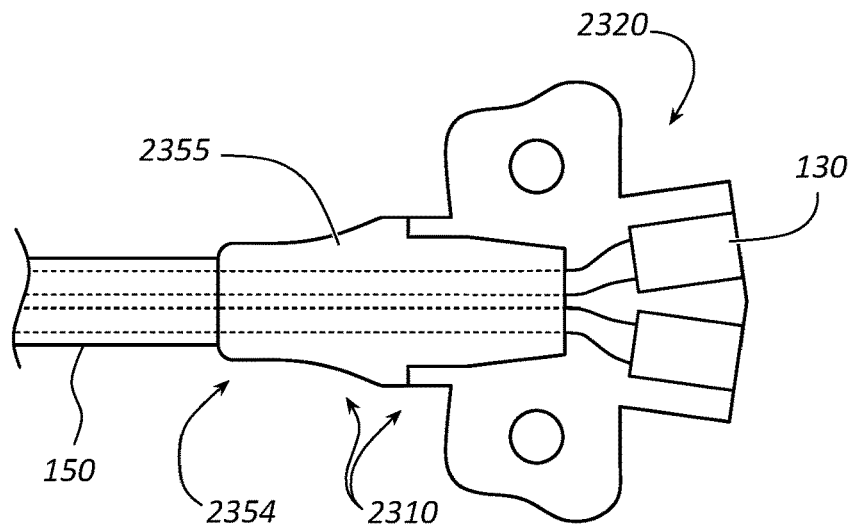
FIG. 23A illustrates a top cross-sectional view of a twenty-first connection mechanism in accordance with some embodiments.
Figure 23B:
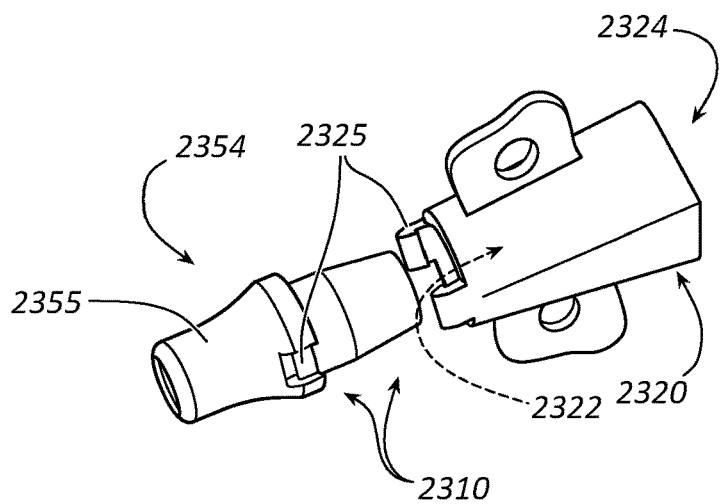
FIG. 23B illustrates a perspective view of the twenty-first connection mechanism in accordance with some embodiments.
Figure 23C:
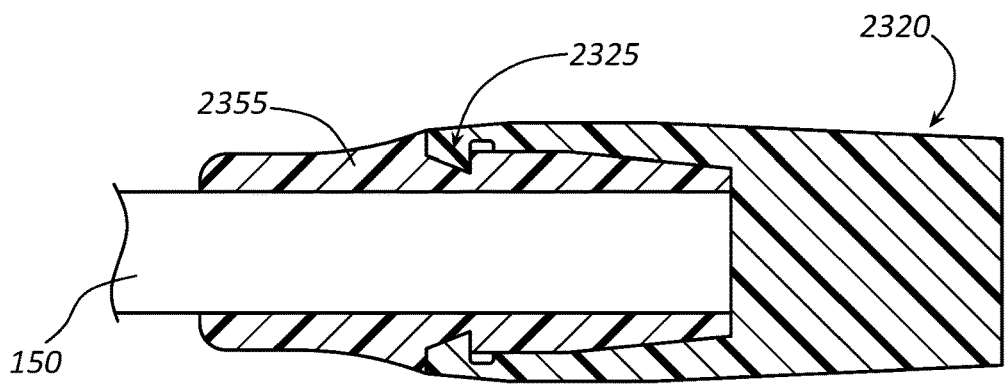
FIG. 23C illustrates a side cross-sectional view of the twenty-first connection mechanism in accordance with some embodiments.

FIG. 23A illustrates a top cross-sectional view of a twenty-first connection mechanism 2310 in accordance with some embodiments. FIG. 23B illustrates a perspective view of the twenty-first connection mechanism 2310 in accordance with some embodiments. FIG. 23C illustrates a side cross-sectional view of the twenty-first connection mechanism 2310 in accordance with some embodiments.

As shown, the connection mechanism 2310 of the catheter assembly 2300 is similar to the connection mechanisms 2110 and 2210 respectively of the catheter assemblies 2100 and 2200 in that the connection mechanism 2310 includes a hub 2320 with a hub-based securement feature 2324 configured to interlock with a catheter tube-based securement feature 2354 over the catheter tube 150. The hub-based securement feature 2324 can likewise include a bore 2322 in the hub 2320, wherein the bore 2322 is configured with a taper in which a diameter of the bore 2322 is greater at a distal end of the bore 2322 than the diameter of the bore 2322 at a proximal end of the bore 2322. With such a taper, the bore 2322 can also function as a receiver for a collet proper 2355. The catheter tube-based securement feature 2354 can likewise include the collet proper 2355 through which the catheter tube 150 can pass. The collet proper 2355 can optionally include 2-4 longitudinal slits through a side wall of the collet proper 2355 but need not include such longitudinal slits like the collet proper 2155 of the connection mechanism 2110. This is because the collet proper 2355 can have a lower durometer than at least a portion of the hub 2320 including the bore 2322. (Again, the connection mechanism 2110 of the catheter assembly 2100 can also feature a difference in durometers.)

Between the hub 2320 and the collet proper 2325 are one or more fasteners such as fastener 2325, which can be a combination of i) at least two overhanging but radially directed protrusions effectively distally extending a portion of the bore 2322 with ii) at least two matching indentations or pockets in an outer surface of the collet proper 2355 configured to lock the resulting two-piece collet together. The overhanging protrusions and the matching indentations or pockets of the fastener 2325 facilitate finding a seat for the collet proper 2325 in the bore 2322 in a way that is easy to see. Upon insertion of the catheter tube 150 over the pair of cannulas 130 or 230, the collet proper 2355 can be configured to slide over the catheter tube 150 until the collet proper 2355 is completely seated in the bore 2322, whereby, due to the taper of the bore 2322 and a difference in durometers, the collet proper 2355 closes down on the catheter tube 150 around the pair of cannulas 130 or 230 and compresses the catheter tube 150 thereon. The hub-based securement feature 2324 including the hub 2320 and the catheter tube-based securement feature 2354 including the collet proper 2355 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 24A:
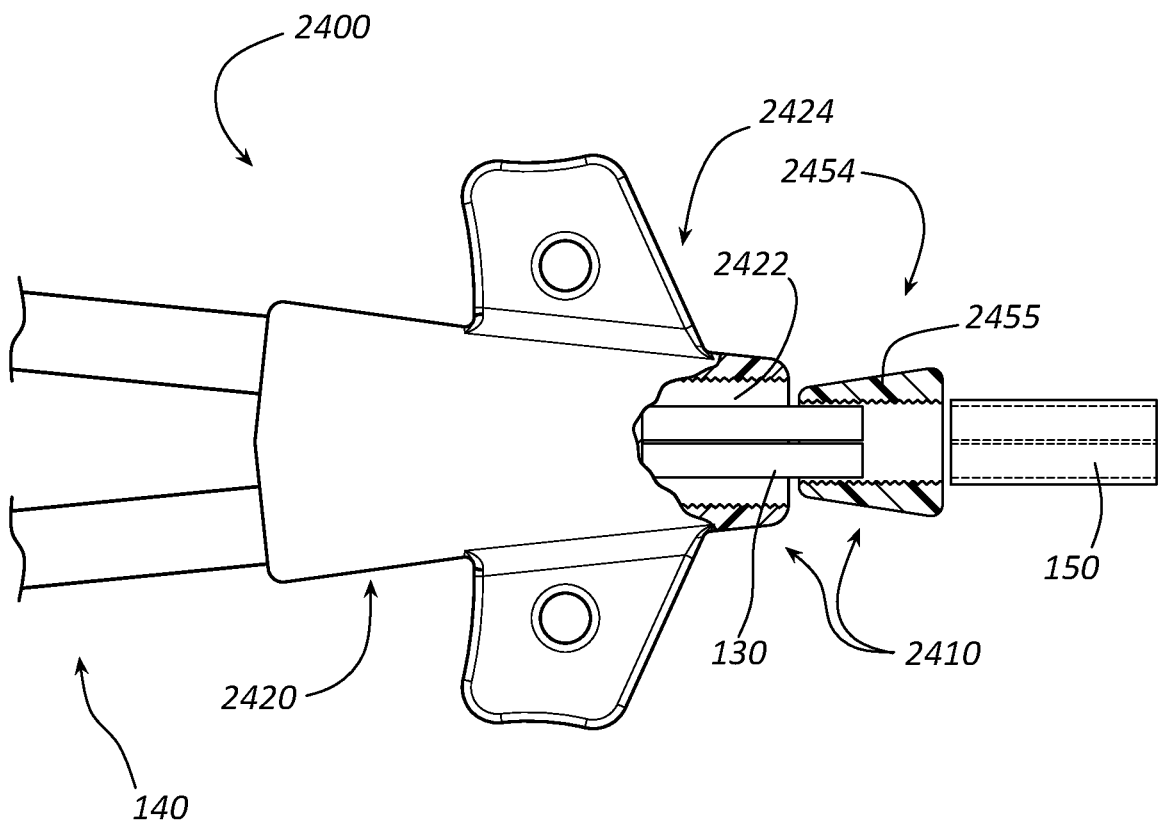
FIG. 24A illustrates a twenty-second connection mechanism of a catheter assembly in accordance with some embodiments.
Figure 24B:
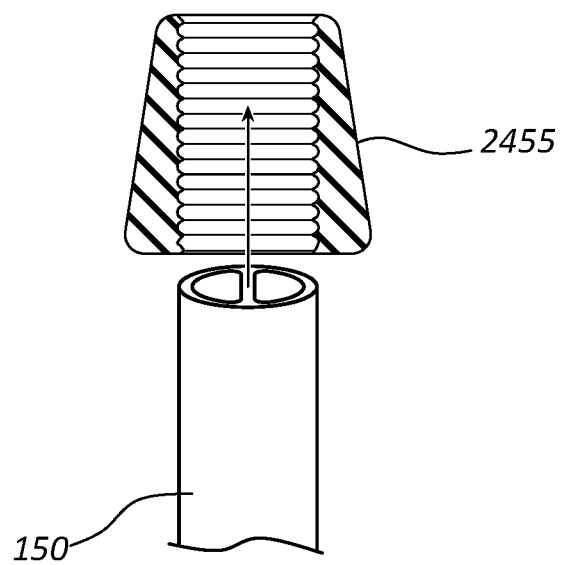
FIG. 24B illustrates a collet proper of the twenty-second connection mechanism in accordance with some embodiments.

FIG. 24A illustrates a twenty-second connection mechanism 2410 of a catheter assembly 2400 in accordance with some embodiments. FIG. 24B illustrates a collet proper 2455 of the twenty-second connection mechanism 2410 in accordance with some embodiments.

As shown, the connection mechanism 2410 of the catheter assembly 2400 includes a hub 2420 with a hub-based securement feature 2424 configured to interlock with a catheter tube-based securement feature 2454 over the catheter tube 150. The hub-based securement feature 2424 can include a bore 2422 in the hub 2420, wherein the bore 2422 is configured with a taper in which a diameter of the bore 2422 is greater at a distal end of the bore 2422 than the diameter of the bore 2422 at a proximal end of the bore 2422. With such a taper, the bore 2422 can function as a receiver for the collet proper 2455. The catheter tube-based securement feature 2454 can include the collet proper 2455 through which the catheter tube 150 can pass. Each of an inner surface of the bore 2422 and an inner surface of the collet proper 2455 can include a number of protrusions such as bumps, ridges such as circumferential protrusions of an internal thread, or a combination thereof configured to bite into or otherwise secure the catheter tube 150 in the collet proper 2455 and, in turn, in the bore 2422.

The collet proper 2355 can have a lower durometer than at least a portion of the hub 2320 including the bore 2322. Upon insertion of the catheter tube 150 over the pair of cannulas 130 or 230, the collet proper 2455 can be configured to slide over the catheter tube 150 until the collet proper 2455 is completely seated in the bore 2422. Due to the taper of the bore 2422, the number of inner-surface protrusions on both the bore 2422 and the collet proper 2455, and a difference in durometers, the collet proper 2455 closes down on the catheter tube 150 around the pair of cannulas 130 or 230 and compresses the catheter tube 150 thereon. The hub-based securement feature 2424 including the hub 2420 and the catheter tube-based securement feature 2454 including the collet proper 2455 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

FIG. 25A illustrates a twenty-third connection mechanism 2510 of a catheter assembly 2500 in accordance with some embodiments. FIG. 25B illustrates a collet proper 2555 of twenty-third connection mechanism 2510 in accordance with some embodiments. FIG. 25C illustrates a longitudinal cross section of the collet proper 2555 of the twenty-third connection mechanism 2510 in accordance with some embodiments.

As shown, the connection mechanism 2510 of the catheter assembly 2500 includes a hub 2520 with a hub-based securement feature 2524 configured to interlock with a catheter tube-based securement feature 2554 over the catheter tube 150. The hub-based securement feature 2524 can include a bore 2522 in the hub 2520, wherein the bore 2522 is configured with a diameter that is slightly smaller than a diameter of the collet proper 2555 for which the bore 2522 is a receiver. The catheter tube-based securement feature 2554 can include the collet proper 2555 through which the catheter tube 150 can pass. To accommodate the collet proper 2555 with the slightly smaller diameter of the bore 2522, each of a top and a bottom of the hub 2520 about the bore 2522 is configured as a flexure 2526 or stiff living hinge, wherein each flexure separates away from the other flexure upon introduction of the collet proper 2555 to the bore 2522.

In addition, each flexure of the top and the bottom flexures can include a ratchet 2527 mounted in a bore-facing surface of the flexure 2526. Each of a top and a bottom of the collet proper 2555 includes an integrated rack 2527 configured to interlock with a ratchet of a flexure when the collet proper 2555 is inserted into the bore 2522. Upon insertion of the catheter tube 150 over the pair of cannulas 130 or 230, the collet proper 2555 can be advanced over the catheter tube 150 until the collet proper 2555 engages with the bore 2522. Due to the slightly smaller diameter of the bore 2522, as well as the ratchets of the flexures and the integrated gear racks of the collet proper 2555, the collet proper 2555 closes down and locks on the catheter tube 150 around the pair of cannulas 130 or 230. The hub-based securement feature 2524 including the hub 2520 and the catheter tube-based securement feature 2554 including the collet proper 2555 can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

f. Collet-Type: Collar-Based Receivers

Figure 26:
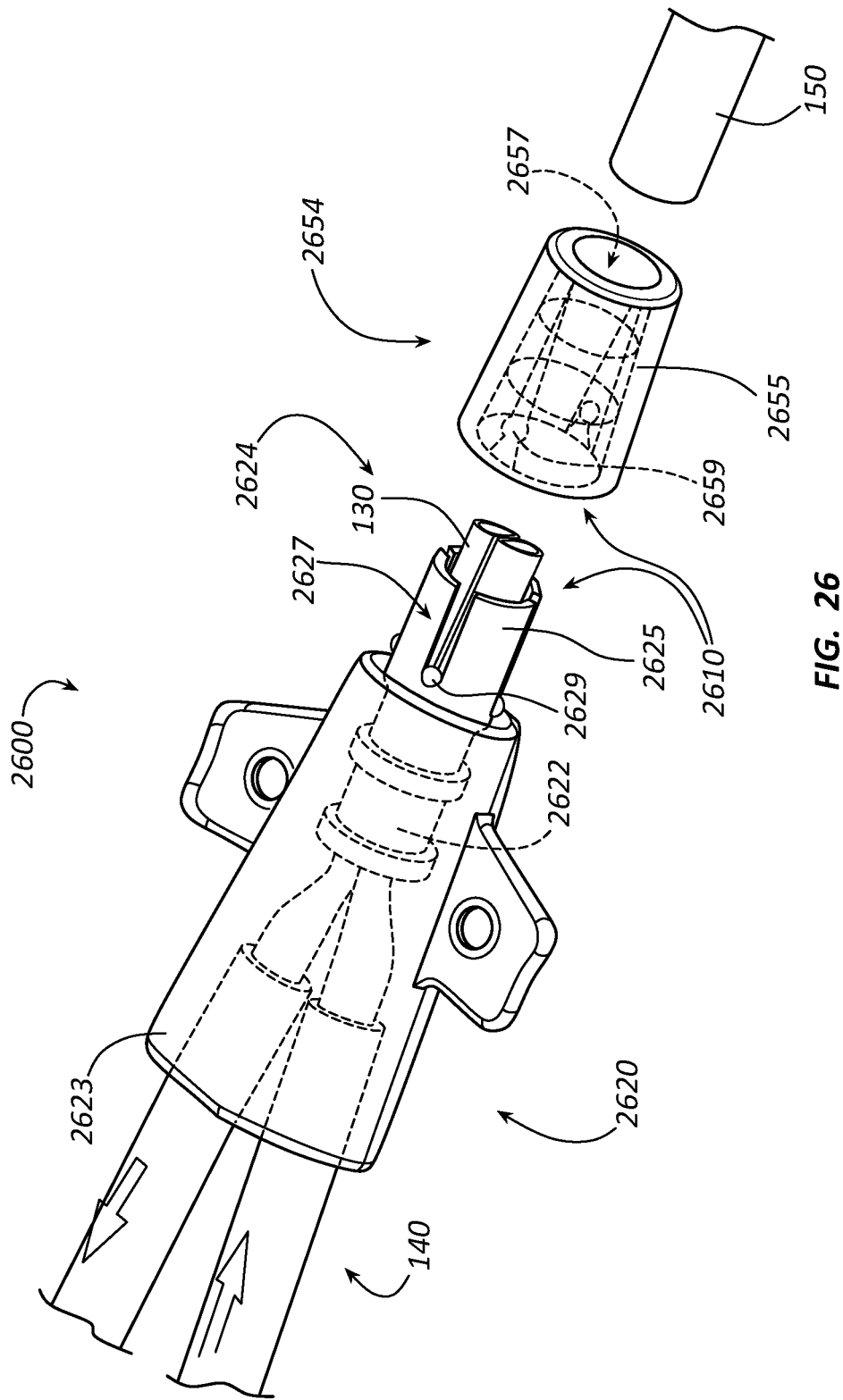
FIG. 26 illustrates a twenty-fourth connection mechanism of a catheter assembly in accordance with some embodiments.

FIG. 26 illustrates a twenty-fourth connection mechanism 2610 of a catheter assembly 2600 in accordance with some embodiments.

As shown, the connection mechanism 2610 of the catheter assembly 2600 includes a hub 2620 with a hub-based securement feature 2624 configured to interlock with a catheter tube-based securement feature 2654 over the catheter tube 150. The hub-based securement feature 2624 can include a collet proper 2625 as part of an inner hub 2622 extending from an outer hub 2623 molded over the inner hub 2622. The collet proper 2625 can include 2-4 longitudinal slits through a side wall of the collet proper 2625 as exemplified by longitudinal slit 2627. The 2-4 longitudinal slits divide the side wall of the collet proper 2625 into a corresponding 2-4 compressible pieces that are configured to be compressed by a taper of a receiver for the collet proper 2625 when the collet proper 2625 is inserted therein. The catheter tube-based securement feature 2654 can include a collet cap 2655 through which the catheter tube 150 can pass. The collet cap 2655 can also include a bore 2657, wherein the bore 2657 is configured with a taper in which a diameter of the bore 2657 is greater at a proximal end of the bore 2657 than the diameter of the bore 2657 at a distal end of the bore 2657. With such a taper of the bore 2657, the collet cap 2655 can also function as the receiver for the collet proper 2625.

Upon insertion of the catheter tube 150 over the pair of cannulas 130 or 230, the collet cap 2655 including the integrated receiver can be configured to slide over the catheter tube 150 until the collet proper 2625 is completely seated in the bore 2657 of the collet cap 2655, whereby, due to the taper of the bore 2657, the 2-4 compressible pieces of the collet proper 2625 close down on the catheter tube 150 around the pair of cannulas 130 or 230 and compresses the catheter tube 150 thereon. Between the collet cap 2655 and the inner hub 2622 are one or more fasteners such as fastener portion 2629 (e.g., a protrusion on an outer surface of the inner hub 2622) and fastener portion 2659 (e.g. a groove in side wall of the collet cap 2655 to capture the protrusion) configured to lock the resulting two-piece collet together. The hub-based securement feature 2624 including the collet proper 2625 and the catheter tube-based securement feature 2654 including the integrated collet cap 2655 receiver can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

Figure 27A:
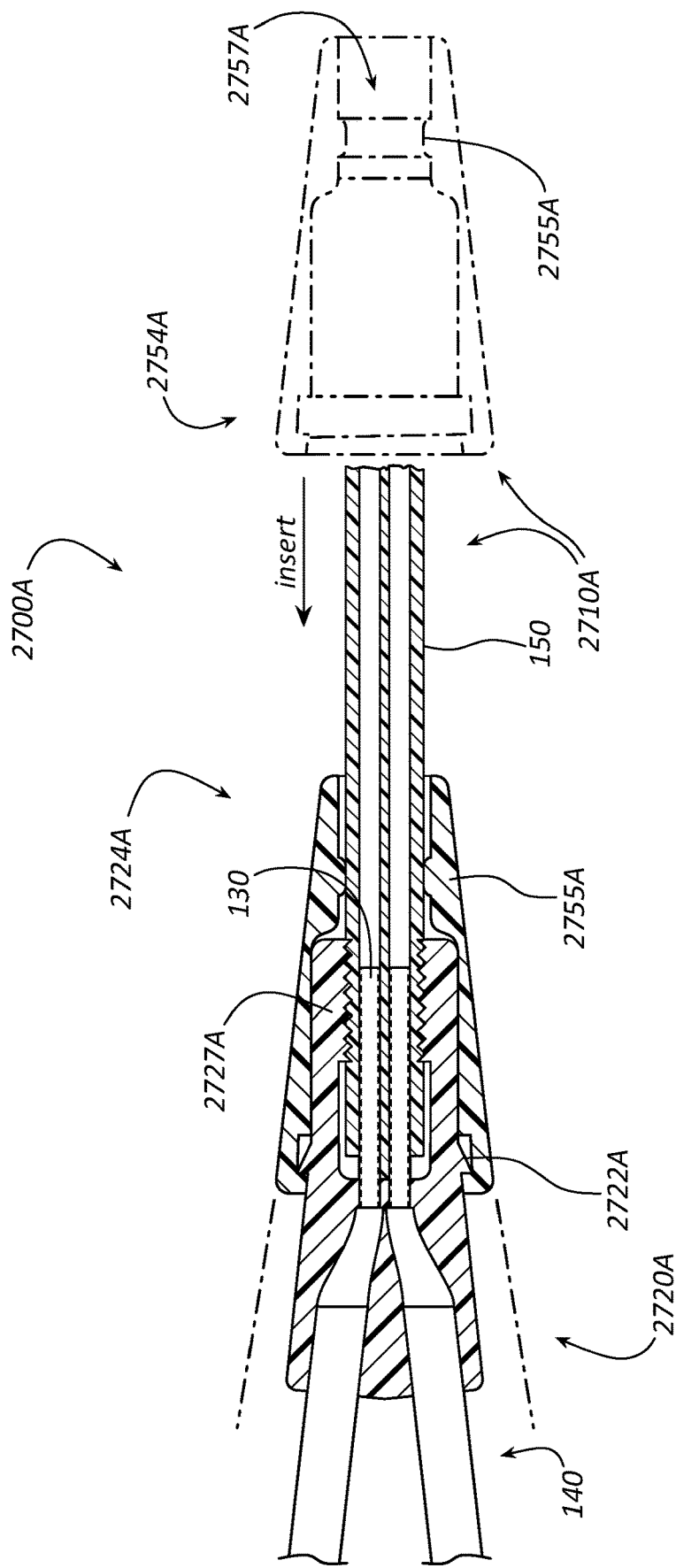
FIG. 27A illustrates a twenty-fifth connection mechanism of a catheter assembly in accordance with some embodiments.
Figure 27B:
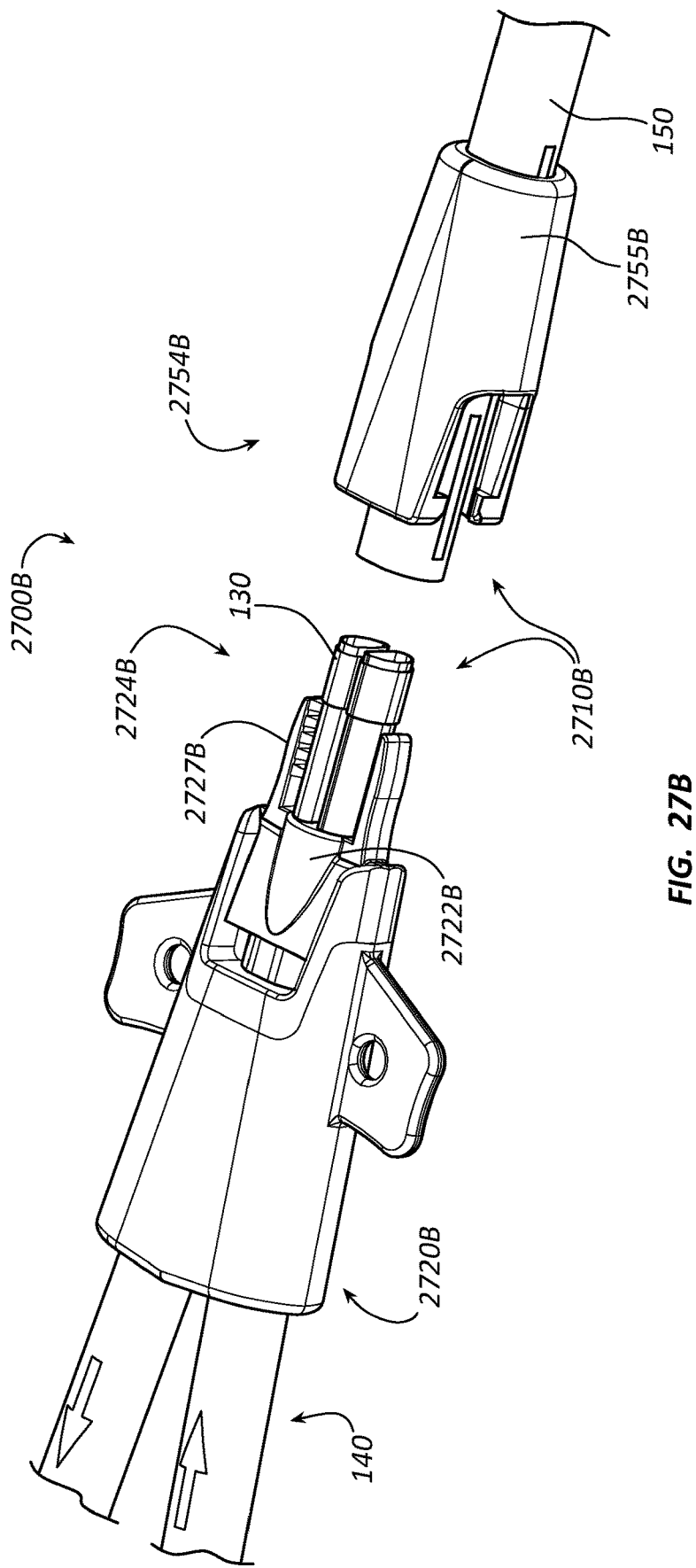
FIG. 27B illustrates a twenty-sixth connection mechanism of a catheter assembly in accordance with some embodiments.

FIG. 27A illustrates a twenty-fifth connection mechanism 2710A of a catheter assembly 2700A in accordance with some embodiments. FIG. 27B illustrates a twenty-sixth connection mechanism 2710B of a catheter assembly 2700B in accordance with some embodiments.

As shown, the connection mechanism 2710A, 2710B of the catheter assembly 2700A, 2700B includes a hub 2720A, 2720B with a hub-based securement feature 2724A, 2724B configured to interlock with a catheter tube-based securement feature 2754A, 2754B over the catheter tube 150. The hub-based securement feature 2724A, 2724B can include a collet proper 2727A, 2727B, or 2-4 compressible arms, as an extension of an inner hub 2722A, 2722B. Pieces of the collet proper 2727A, 2727B, or the compressible arms, can include textured inner surfaces configured to grip the catheter tube 150. Whether the collet proper 2727A, 2727B or the compressible arms, a taper of a receiver for the collet proper 2727A, 2727B or the compressible arms is configured to compress the collet proper 2727A, 2727B or the compressible arms when inserted therein. The catheter tube-based securement feature 2754A, 2754B can include a collet cap 2755A, 2755B through which the catheter tube 150 can pass. The collet cap 2755A, 2755B can also include a bore (e.g., see bore 2757A), wherein the bore is configured with a taper in which a diameter of the bore is greater at a proximal end of the bore than the diameter of the bore at a distal end of the bore. With such a taper of the bore, the collet cap 2755A, 2755B can also function as the receiver for the collet proper 2727A, 2727B or the compressible arms.

Upon insertion of the catheter tube 150 over the pair of cannulas 130 or 230, the collet cap 2755A, 2755B including the integrated receiver can be configured to slide over the catheter tube 150 until the collet proper 2727A, 2727B, or each of the compressible arms, is completely seated in the bore (e.g., see bore 2757A) of the collet cap 2755A, 2755B, whereby, due to the taper of the bore, the pieces of the collet proper 2727A, 2727B, or the compressible arms, close down on the catheter tube 150 around the pair of cannulas 130 or 230 and compresses the catheter tube 150 thereon. While not shown, between the collet cap 2755A, 2755B and the inner hub 2722A, 2722B can be one or more fasteners configured to lock the resulting two-piece collet together. The hub-based securement feature 2724A, 2724B including the collet proper 2727A, 2727B and the catheter tube-based securement feature 2754A, 2754B including the integrated collet cap 2755A, 2755B receiver can be further configured with a structural integrity (e.g., thickness, durometer, etc.) and tensile strength sufficient to resist displacement of the catheter tube 150, once connected, under normal operating conditions, thereby providing a secure fluid-tight connection between the catheter tube 150 and the pair of cannulas 130 or 230.

3. Other Connection Mechanisms

As set forth herein, the catheter assemblies can be configured with any connection mechanism or combination of connection-mechanism features disclosed herein. While certain features are described in association with, for example, collarless connection mechanisms, and while certain other features are described in association with, for example, collared connection mechanisms, such features need not be mutually exclusive. Indeed, FIGS. 28 and 29, for example, illustrate connection mechanisms at least partially resulting from combinations of such connection-mechanism features.

FIG. 28 illustrates a twenty-seventh connection mechanism 2810 of a catheter assembly 2800 in accordance with some embodiments.

As shown, the connection mechanism 2810 of the catheter assembly 2800 includes a hub 2820 with a hub-based securement feature 2824 configured to interlock with a catheter tube-based securement feature 2854 over the catheter tube 650 (see FIG. 6). Like the hub 1820 of the catheter assembly 1800 of FIG. 18, the hub-based securement feature 2824 can include a pair of receiving slots 2827 in an inner hub or outer hub of the hub 2820. The catheter tube-based securement feature 2854 can be configured as a collar 2855 configured, in part, like the socket 622 of the catheter assembly 600 of FIG. 6 to accommodate at least one circumferential barb of the catheter tube 650. Like the collar 1855 of the catheter assembly 1800 of FIG. 17, the collar 2855 can include a pair of interlocking arms 2857 extending from the collar 2855 for interlocking with the receiving slots 2827 in the inner hub or outer hub of the hub 2820.

FIG. 29 illustrates a twenty-eighth connection mechanism 2910 of a catheter assembly 2900 in accordance with some embodiments.

As shown, the connection mechanism 2910 of the catheter assembly 2900 includes a hub 2920 with a hub-based securement feature 2924 configured to interlock with a catheter tube-based securement feature 2954 over the catheter tube 650 (see FIG. 6). Like the hub 1420 of the catheter assembly 1400 of FIG. 14, the hub-based securement feature 2924 can include two or more protrusions 2925 in an outer surface of the hub 2920 such as the outer surface of an inner hub. The catheter tube-based securement feature 2954 can be configured as a collar 2955 configured, in part, like the socket 622 of the catheter assembly 600 of FIG. 6 to accommodate at least one circumferential barb of the catheter tube 650. Like the collar 1455 of the catheter assembly 1400 of FIG. 14, the collar 2955 can be configured with one or more indentations 2957 in an inner surface (or one or more holes therethrough) at a proximal end portion of the collar 2955 for interlocking with the two or more protrusions 2925 in the outer surface of the hub 2920.

4. Compression Inserts in Connection Mechanisms

As set forth herein, the catheter assemblies can be configured with any connection mechanism or combination of connection-mechanism features disclosed herein. In addition to any features described in association with, for example, collarless connection mechanisms, collared connection mechanisms, and the like, a catheter assembly can be configured with a compression insert. Indeed, FIGS. 30A and 30B, for example, illustrate a connection mechanism including such a compression insert.

FIG. 30A illustrates a twenty-ninth connection mechanism 3010 of a catheter assembly 3000 including a compression insert 3055 in accordance with some embodiments. FIG. 30B illustrates a perspective view of the compression insert 3055.

As shown, the connection mechanism 3010 of the catheter assembly 3000 includes a catheter tube-based securement feature 3054 including the compression insert 3055. The compression insert 3055 can be configured like a plug for insertion into the catheter tube 150; however, unlike a plug, the compression insert 3055 includes through holes 3057 to maintain patency of the arterial and venous lumens. The compression insert 3055 can be further configured for disposal over the pair of cannulas 130.

A notable feature of the compression insert 3055 is the strategic compression the compression insert 3055 applies on the pair of cannulas 130 to correct for unwanted deformation of the catheter tube 150 by the pair of cannulas 130, insufficient sealing between the catheter tube 150 and the pair of cannulas 130, or both that might otherwise cause a connection mechanism to leak. For example, in a pair of 'D'-shaped cannulas (i.e., a pair of cannulas in which each cannula has a 'D' shape in cross section like a though hole of the through holes 3057 of the compression insert 3055 of FIG. 30B), a gap can occur between the pair of cannulas and the catheter tube 150 when disposed thereover, particularly in areas having a tight radius of curvature. The compression insert 3055 corrects for this with strategic compression, for example, around the areas having the tight radius of curvature, thereby enhancing a seal between the pair of cannulas and the catheter tube 150. The compression insert 3055 can be used in place of another connection mechanism set forth herein, in addition to another connection mechanism set forth herein, or incorporated as a feature of another connection mechanism set forth herein.

5. Coatings for Connection Mechanisms

As set forth herein, the catheter assemblies can be configured with any connection mechanism or combination of connection-mechanism features disclosed herein. In addition to any features described in association with, for example, collarless connection mechanisms, collared connection mechanisms, and the like, a catheter assembly can be configured with a coating over a pair of cannulas to further provide a secure fluid-tight connection between a catheter tube and the pair of cannulas.

Figure 31A:
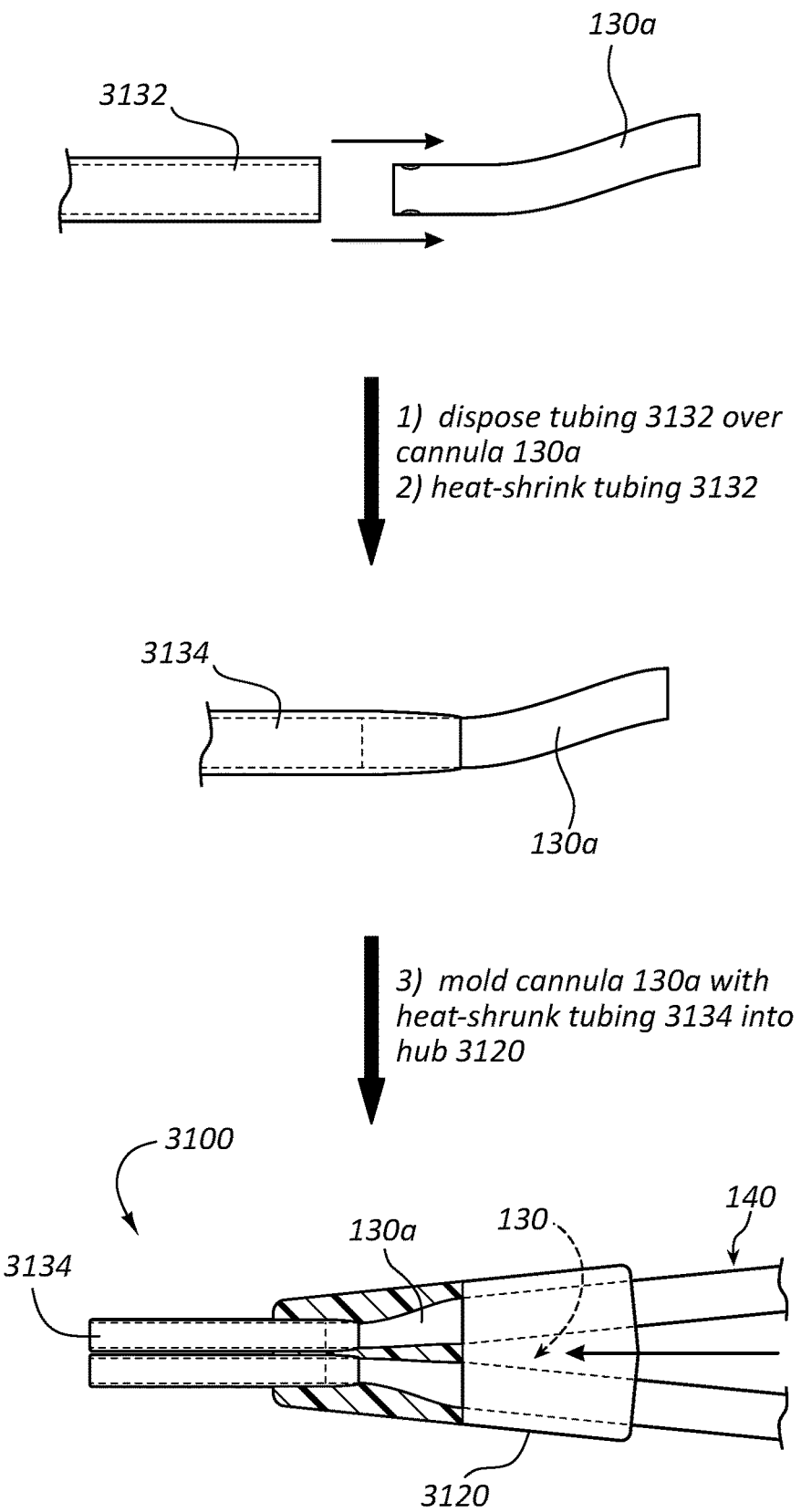
FIG. 31A illustrates a pair of cannulas with a first coating in accordance with some embodiments.

FIG. 31A illustrates the pair of cannulas 130 with a first coating in accordance with some embodiments.

As shown, the first coating can be heat-shrunk tubing 3134 such as heat-shrunk polyurethane tubing over each cannula of a pair of cannulas as exemplified by cannula 130a of the pair of cannulas 130. The heat-shrunk tubing 3134 can extend from a distal end portion of the cannula 130a such as a distal end of the cannula 130a up to at least a hub of a catheter assembly; however, it can be advantageous to extend the heat-shrunk tubing 3134 through at least a portion of the hub to further secure the heat-shrunk tubing 3134 to the cannula, which is exemplified by hub 3120 of catheter assembly 3100. Furthermore, it can be advantageous to notch or put a circumferential groove in the distal end portion the cannula 130a prior to effecting the heat-shrunk tubing 3134 on the cannula 130a, as the heat-shrunk tubing 3134 can be shrunk into the notch or circumferential groove, thereby creating a smooth transition from the distal end of the cannula 130a and a distal end of the heat-shrunk tubing 3134 when not terminating together. Heat-shrunk tubing over a pair of cannulas further provides a secure fluid-tight connection between a catheter tube and the pair of cannulas due to a tight fit of the heat-shrunk tubing on the pair of cannulas and a like-to-like interaction between the catheter tube and the heat-shrunk tubing.

In an example of effecting the first coating, a piece of heat-shrinkable tubing 3132 is disposed over the cannula 130a followed by heating to provide the cannula 130a with the heat-shrunk tubing 3134 thereon. Such heat shrinking can be performed either before or after molding a hub over the pair of cannulas 130 in embodiments in which the heat-shrunk tubing 3134 extends up to the hub (but not farther). In embodiments in which the heat-shrunk tubing extends through at least a portion of the hub such as the hub 3120, the heat-shrinking is performed first followed by molding the hub 3120 over the pair of cannulas 130 and the heat-shrunk tubing 3134.

Figure 31B:
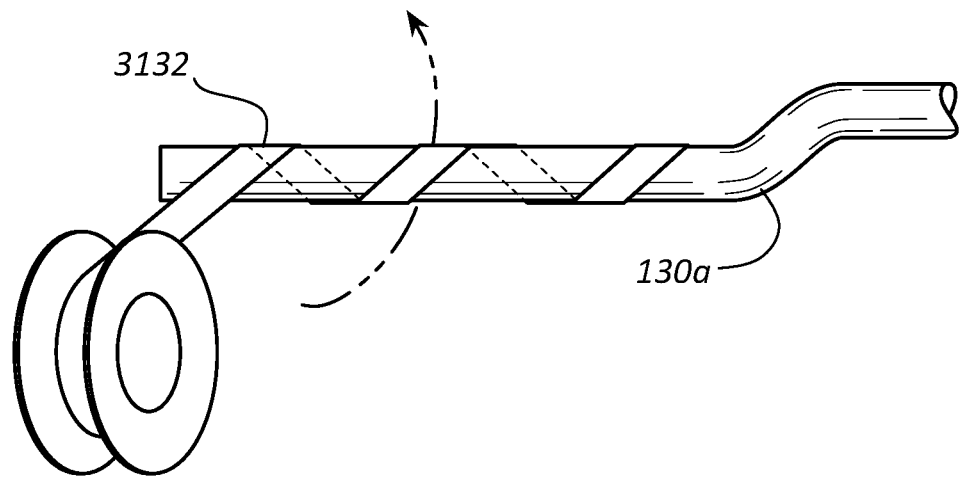
FIG. 31B illustrates a cannula of a pair of cannulas with a second coating in accordance with some embodiments.
Figure 31C:
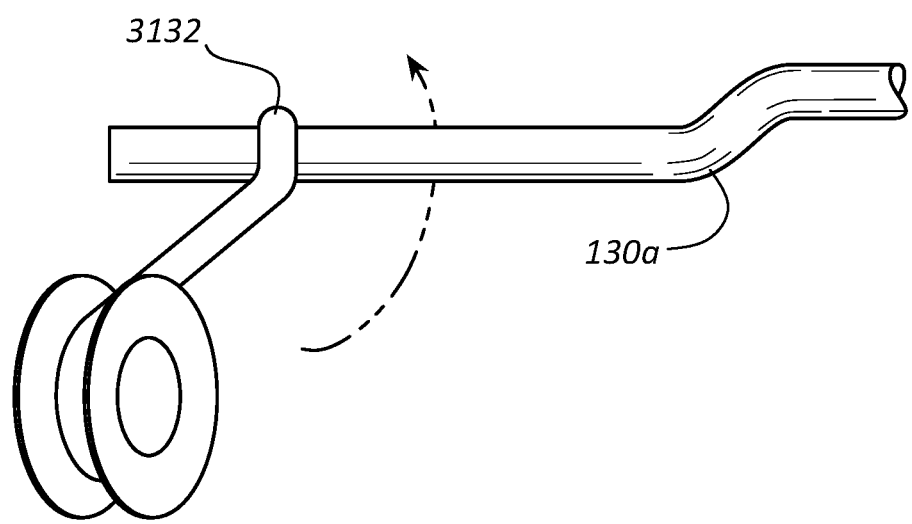
FIG. 31C illustrates a cannula of a pair of cannulas with a third coating in accordance with some embodiments.

FIG. 31B illustrates the cannula 130a of the pair of cannulas 130 with a second coating in accordance with some embodiments. FIG. 31C illustrates the cannula 130 of the pair of cannulas 130 with a third coating in accordance with some embodiments.

As shown, both the second coating and the third coating can be a wrapping of a thin (e.g., 1 mil or 1/1000 of an inch) polymer wrap such as a polyurethane wrap over a cannula of a pair of cannulas as exemplified by the cannula 130a of the pair of cannulas 130. The second coating and the third coating differ in the wrapping of the polymer wrap. The second coating is a wrapping of the polymer wrap over a length of, for example, the cannula 130a, which can extend from a distal end portion of the cannula 130a such as a distal end of the cannula 130a up to at least a hub of a catheter assembly. Like the first coating, it can be advantageous to extend the second coating through at least a portion of the hub to further secure the second coating to the cannula. This can be effected by first wrapping the polymer wrap on the cannula, then molding a hub of a catheter assembly thereover. The third coating is a wrapping of the polymer wrap over a particular location of, for example, the cannula 130a, which effects a circumferential protrusion of the polymer wrap on the cannula 130a at the particular location for a tighter fit. Each of such wrappings over a pair of cannulas further provides a secure fluid-tight connection between a catheter tube and the pair of cannulas due to a tight fit of the wrapping on the pair of cannulas and a like-to-like interaction between the catheter tube and the wrapping.

D. Catheter Assemblies for Priming

Figure 32A:
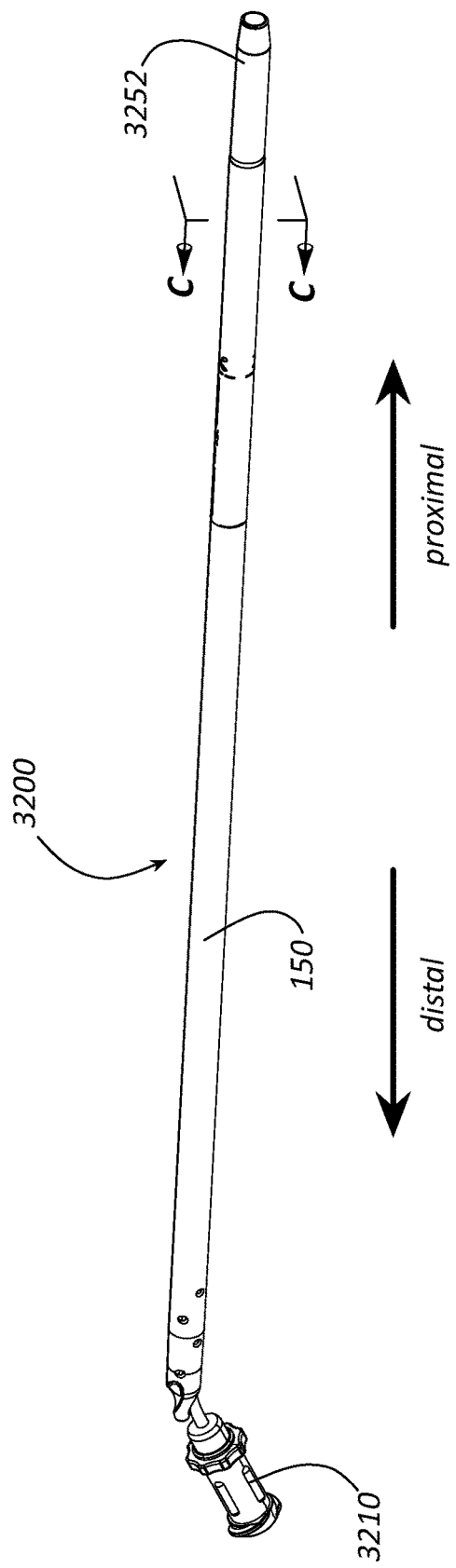
FIG. 32A illustrates a catheter assembly for priming a catheter tube in accordance with some embodiments.
Figure 32B:
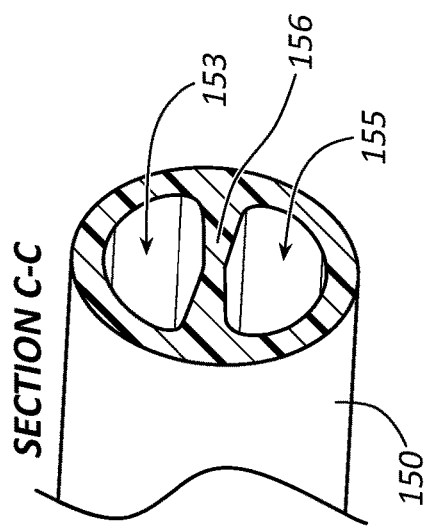
FIG. 32B illustrates a transverse cross section of the catheter tube of the catheter assembly of FIG. 32A.
Figure 32C:
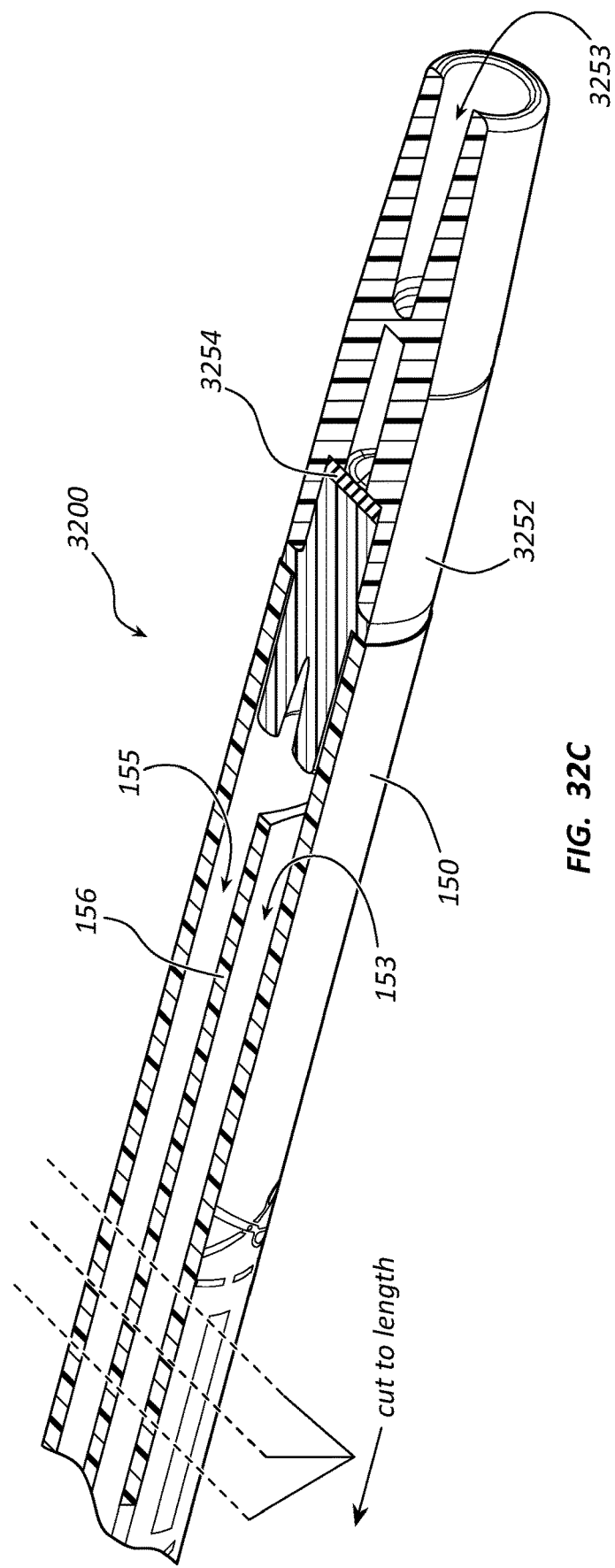
FIG. 32C illustrates a longitudinal cross section of a proximal end portion of the catheter tube of the catheter assembly of FIG. 32A.

FIG. 32A illustrates a catheter assembly 3200 for priming the catheter tube 150 in accordance with some embodiments. FIG. 32B illustrates a transverse cross section of the catheter tube 150 of the catheter assembly 3200 of FIG. 32A, and FIG. 32C illustrates a longitudinal cross section of a proximal end portion of the catheter tube 150 of the catheter assembly 3200 of FIG. 32A.

As shown, the catheter assembly 3200 can include the catheter tube 150, or the like (e.g., the catheter tube 650), a flow-directing cap 3252, and a priming adapter 3210. The catheter tube 150 can include a pair of lumens such as the arterial-catheter-tube lumen 153 and the venous-catheter-tube lumen 155 separated by a septum 156, wherein the pair of lumens extends from a distal end portion to a proximal end portion of the catheter tube 150. The flow-directing cap 3252 can be about the proximal end portion of the catheter tube 150 such as bonded to the proximal end portion of the catheter tube 150, and the flow-directing cap 3252 can include a taper subcutaneously tunneling the tunneling shaft 3510 in a patient. The flow-directing cap 3252 can include a valve 3254 (e.g., hemostatic valve) at a proximal end of the catheter tube 150. The priming adapter 3210, which can be configured with a Luer taper for connecting a syringe for priming, can include a priming stylet 3212 configured for priming both the arterial lumen 153 and the venous lumen 155 of the pair of lumens when the priming stylet 3212 is inserted into either the arterial lumen 153 or the venous lumen 155. (See FIG. 33A for priming stylet 3212.) For example, the priming stylet 3212 can be configured with a length that proximally extends beyond any side-wall openings 152 in the catheter tube 150 at the distal end portion of the catheter tube 150 when the priming stylet 3212 is inserted into either the arterial lumen 153 or the venous lumen 155. (See FIGS. 34A and 34B.)

FIG. 33A illustrates a catheter assembly 3300 for priming the catheter tube 150 in accordance with some embodiments. FIG. 33B illustrates a transverse cross section of the catheter tube 150 of the catheter assembly 3300 of FIG. 33A. FIG. 33C illustrates a longitudinal cross section of a distal end portion of the catheter tube 150 of the catheter assembly 3300 of FIG. 33A, and FIG. 33D illustrates a longitudinal cross section of a proximal end portion of the catheter tube 150 of the catheter assembly 3300 of FIG. 33A.

As shown, the catheter assembly 3300 can include the catheter tube 150, or the like (e.g., the catheter tube 650), the flow-directing cap 3252, and the priming adapter 3210 of the catheter assembly 3200 as well as an over-the-wire ("OTW") adapter 3320, which can be configured with a Luer taper. The OTW adapter 3320 can include an OTW stylet 3322 configured for advancing the catheter tube 150 in a patient over a guidewire in the OTW stylet 3322 when the OTW stylet 3322 is inserted into either the arterial lumen 153 or the venous lumen 155 of the pair of lumens. While the OTW adapter 3320 is configured for insertion into a socket 3253 coaxial with the flow-directing cap 3252 and the catheter tube 150, the catheter tube 150 includes a bifurcation at a beginning of the septum 156 in a proximal end portion of the catheter tube 150 distal to the valve 3254 from which bifurcation the OTW stylet 3322 can follow along either the arterial lumen 153 or the venous lumen 155 of the pair of lumens. FIGS. 33C and 33D show the OTW stylet 3322 following along the arterial lumen 153 until the OTW stylet 3322 exits from a center of the catheter tube 150 after another bifurcation at an end the septum 156 in the distal end portion of the catheter tube 150. The OTW stylet 3322 is configured with a length sufficient to extend the catheter tube 150 a sufficient distance from the distal end of the catheter tube 150 for trackability over a guidewire during placement of the catheter tube 150. Because the OTW 3322 and the priming stylet 3212 cannot occupy the same lumen at the same time, when the OTW 3322 occupies the arterial lumen 153 of the catheter tube 150, the priming stylet 3212 occupies the venous lumen 155 of the catheter tube 150—and vice versa.

The catheter tube 150 can be configured to be cut to length at one or more locations on the catheter tube 150 distal to the flow-directing cap 3252 and the bifurcation in the proximal end portion of the catheter tube 150 (see FIG. 32A). The catheter tube 150 cut at the one or more of the foregoing locations is configured for disposing the catheter tube 150 over the pair of cannulas 130 as set forth herein.

Figure 34A:
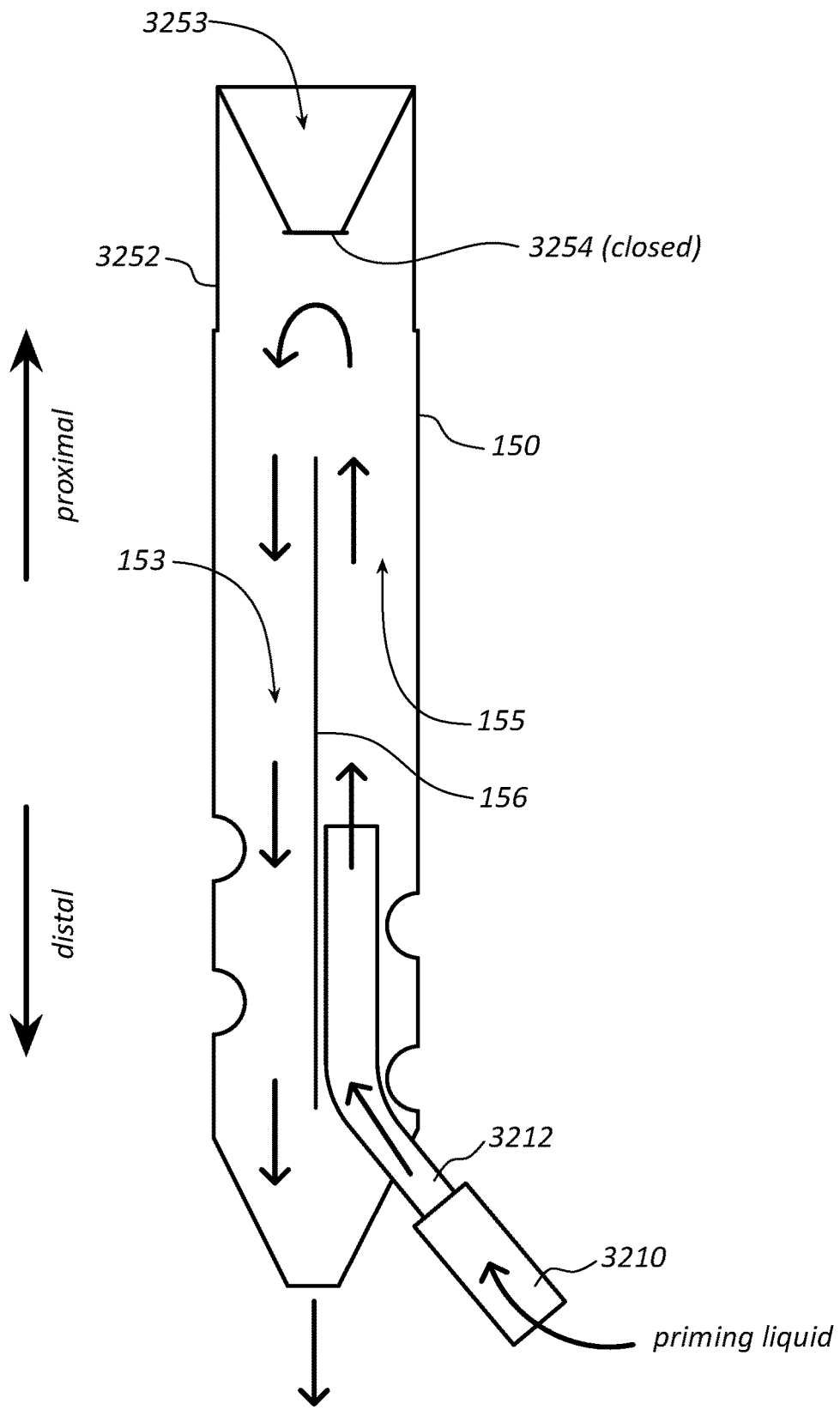
FIG. 34A illustrates fluid flow through the catheter tube of the catheter assembly of FIG. 33A in accordance with some embodiments.
Figure 34B:
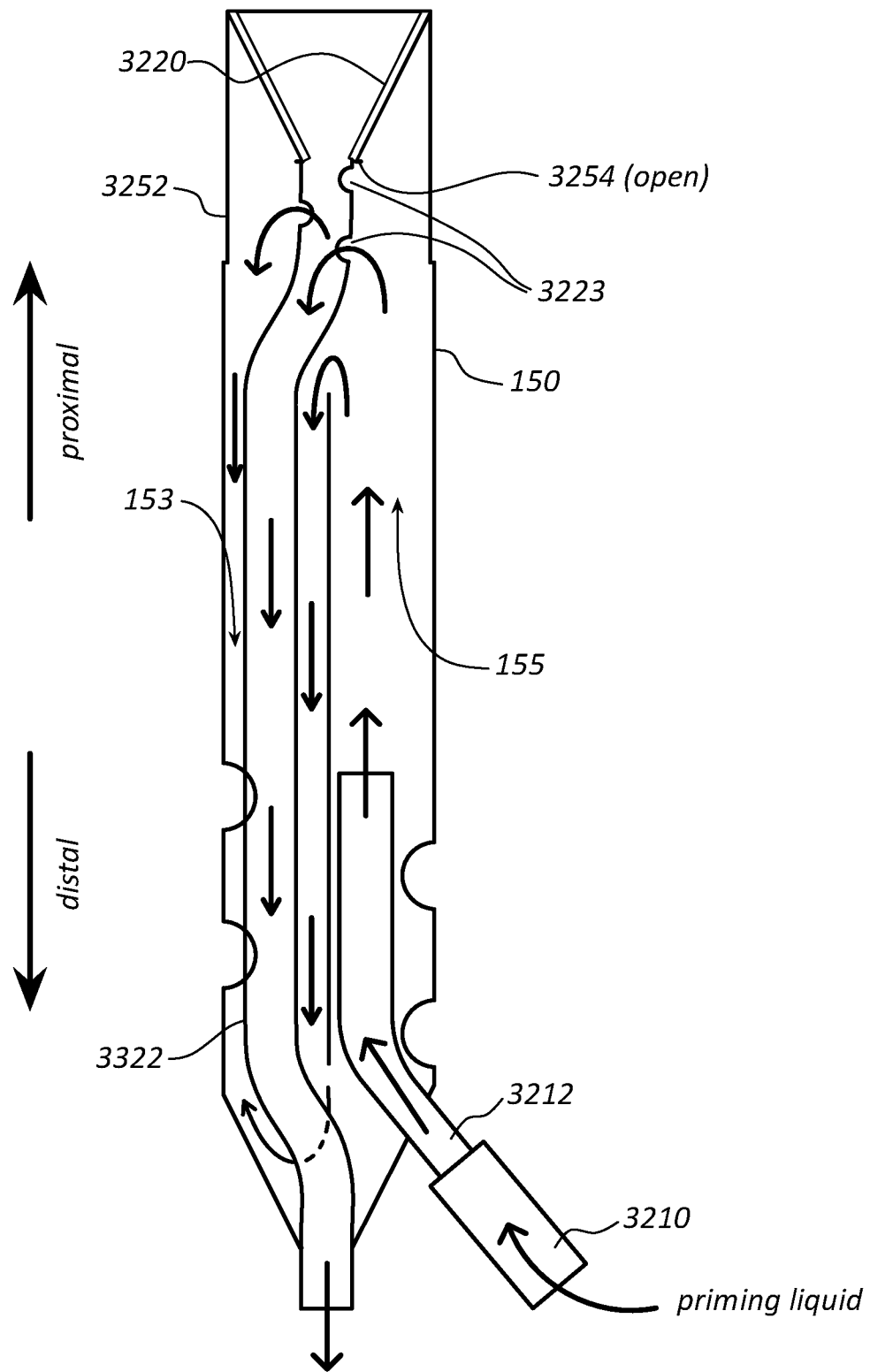
FIG. 34B illustrates fluid flow through the catheter tube of the catheter assembly of FIG. 34A in accordance with some embodiments.

FIG. 34A illustrates fluid flow set through the catheter tube 150 of the catheter assembly 3200 of FIG. 33A in accordance with some embodiments. FIG. 34B illustrates fluid flow through the catheter tube 150 of the catheter assembly 3300 of FIG. 34A in accordance with some embodiments.

As shown in FIG. 34A, the valve 3254 at the proximal end of the catheter tube 150 (e.g., within the flow-directing cap 3252) is configured to remain closed when the OTW stylet 3322 is not inserted into either the arterial lumen 153 or the venous lumen 155 of the pair of lumens. Thus, the valve 3254 closes off the proximal end portion of the catheter tube 150, which enables priming both the venous lumen 155 and the arterial lumen 153 from the distal end portion of the catheter tube 150 from the priming stylet 3212 by way of an attached syringe as shown by the fluid-flow arrows of FIG. 34A when the priming stylet 3212 is inserted into either the venous lumen 155 or the arterial lumen 153. To further enable priming both the venous lumen 155 and the arterial lumen 153 from the distal end portion of the catheter tube 150, the priming stylet 3212 can have a length that proximally extends beyond any side-wall openings 152 in the catheter tube 150 at the distal end portion of the catheter tube 150 when the priming stylet 3212 is inserted into either the arterial lumen 153 or the venous lumen 155.

As shown in FIG. 34B, the valve 3254 at the proximal end of the catheter tube 150 (e.g., within the flow-directing cap 3252) is configured to open when the OTW stylet 3322 is inserted through the valve 3254 and into either the arterial lumen 153 or the venous lumen 155 of the pair of lumens. The OTW stylet 3322 inserted through the valve 3254 effectively closes off the proximal end portion of the catheter tube 150 (instead of the valve 3254), but, in order to enable priming both the venous lumen 155 and the arterial lumen 153 from the distal end portion of the catheter tube 150, the OTW stylet 3322 includes a plurality of openings 3323 (e.g., circular holes, angled holes, slits, skives, etc.) in an end portion of the OTW stylet 3322 allowing priming fluid (e.g., saline or heparinized saline) from an attached syringe to flow therethrough in accordance with the fluid-flow arrows of FIG. 34B. In this way, it is also possible to prime both the venous lumen 155 and the arterial lumen 153 from the distal end portion of the catheter tube 150 from the priming stylet 3212 by way of the fluid-flow arrows of FIG. 34A when the priming stylet 3212 is inserted into one of the venous lumen 155 or the arterial lumen 153 and the OTW stylet 3322 is inserted into another one of the venous lumen 155 or the arterial lumen 153.

While FIG. 34B shows priming both the venous lumen 155 and the arterial lumen 153 from the distal end portion of the catheter tube 150, a similar configuration can be used to prime both the venous lumen 155 and the arterial lumen 153 from the proximal end portion of the catheter tube 150. In such a configuration, the priming adapter 3210 and the priming stylet 3212 can be removed from the distal end of the catheter tube 150 to allow priming fluid (e.g., saline or heparinized saline) from an attached syringe to flow from the OTW adaptor 3220, into the OTW stylet 3322, through the plurality of openings 3323 (e.g., circular holes, angled holes, slits, skives, etc.) in the end portion of the OTW stylet 3322, and through the both the venous lumen 155 and the arterial lumen 153. To increase the flow rate of the priming fluid, or to provide enhanced distribution of the priming fluid in the proximal end portion of the catheter tube 150, an additional plurality of openings (e.g., circular holes, angled holes, slits, etc.) can be incorporated in, for example, a conical end portion of the OTW adaptor 3220 proximal to the plurality of openings 3323 in the OTW stylet 3322. The flow-directing cap 3252, too, can further include a plurality of openings or another valve in the socket 3253 of the flow-directing cap 3252 to allow the priming fluid from the plurality of opening in the OTW adaptor 3220 therethrough. Further, with the OTW stylet 3322 in place during such priming, it can be beneficial to pinch or stopper (e.g., by way of a thumb or finger of a gloved hand) a distal end portion of the OTW stylet 3322 to force the priming fluid through the plurality of opening 3323 instead of out the distal end of the stylet 3322.

E. Catheter Assemblies for Tunneling

Figure 35:
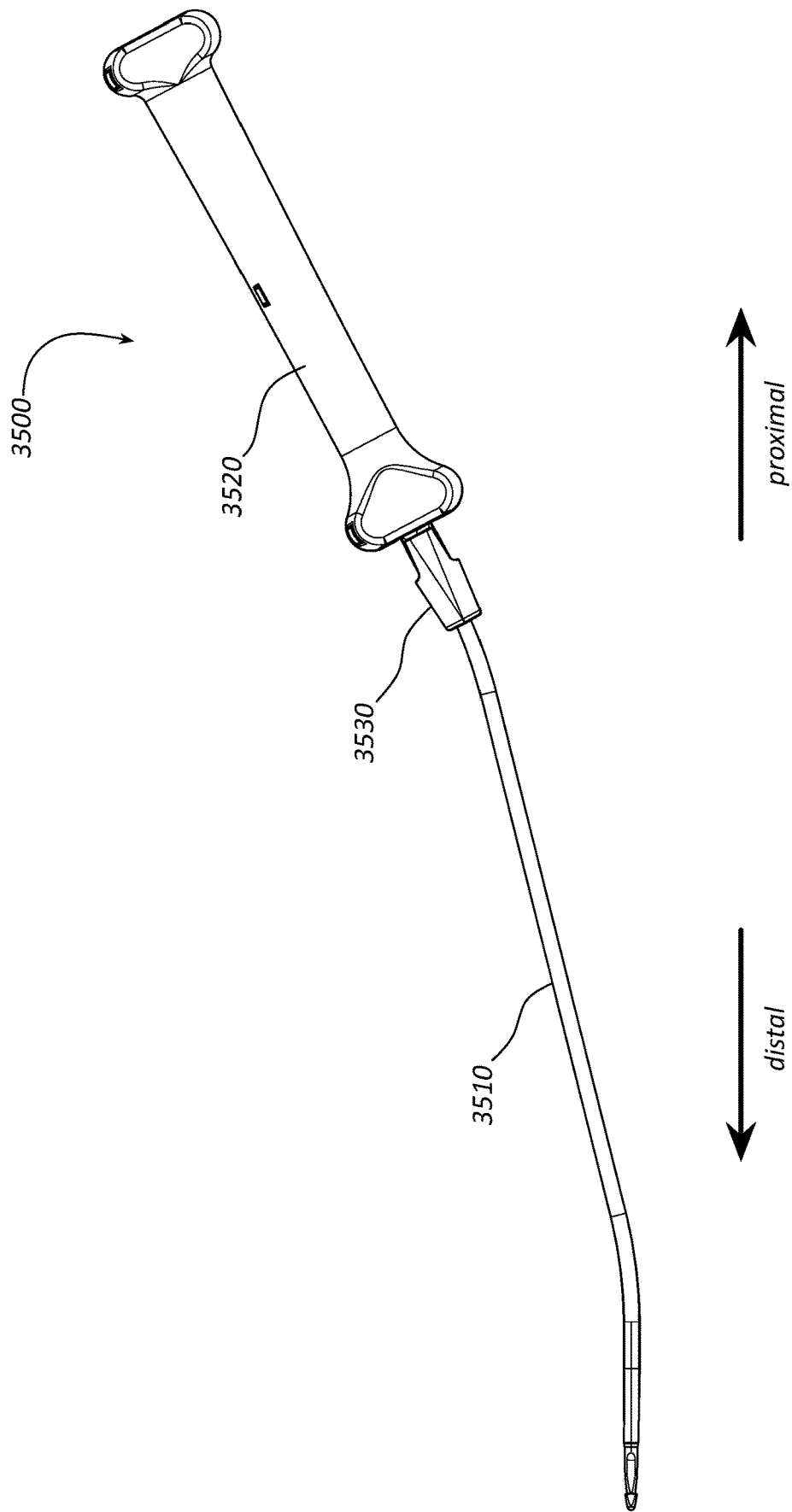
FIG. 35 illustrates a catheter-tube tunneling assembly in accordance with some embodiments.
Figure 36:
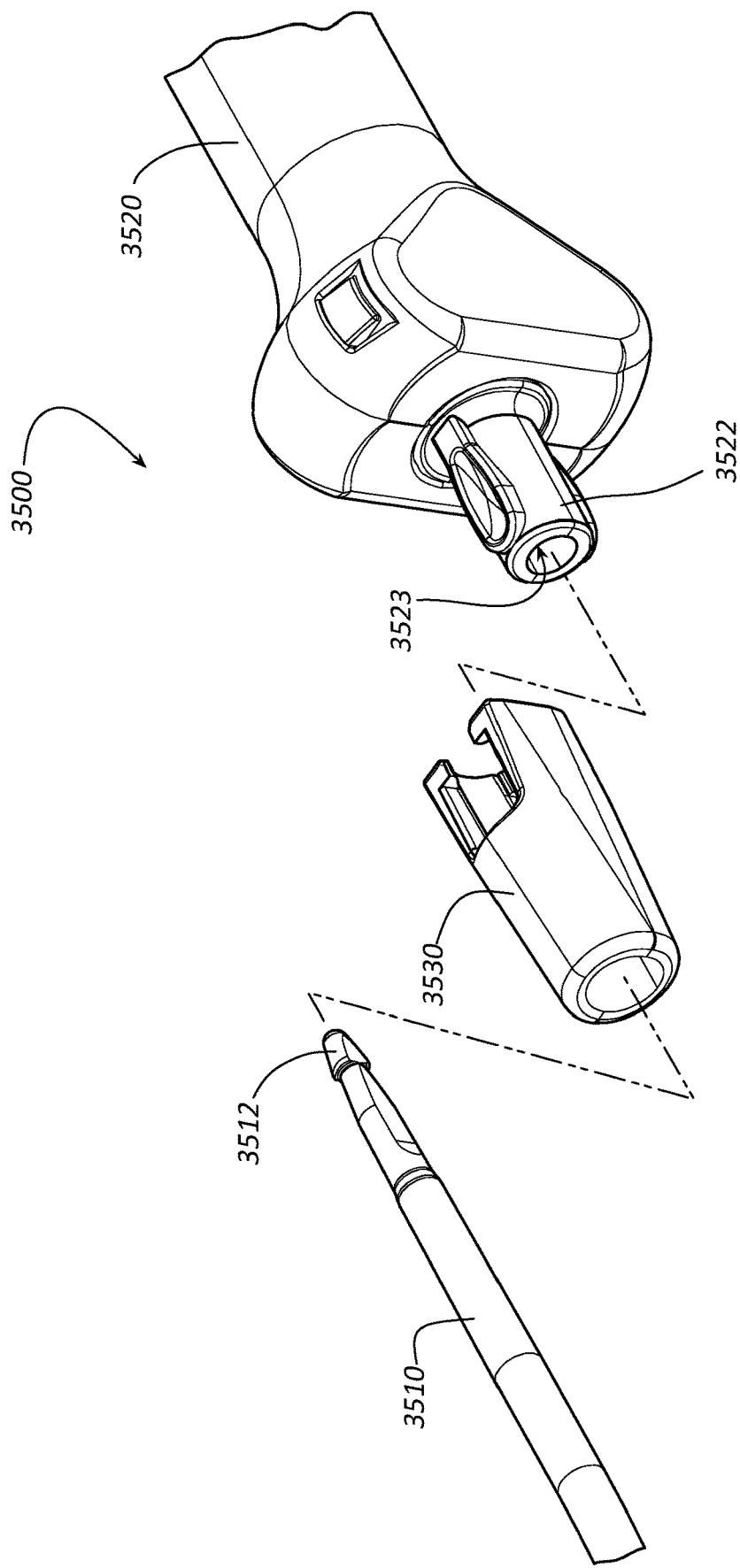
FIG. 36 illustrates a connection of a tunneling shaft to a handle in a catheter-tube tunneling assembly in accordance with some embodiments.
Figure 37:
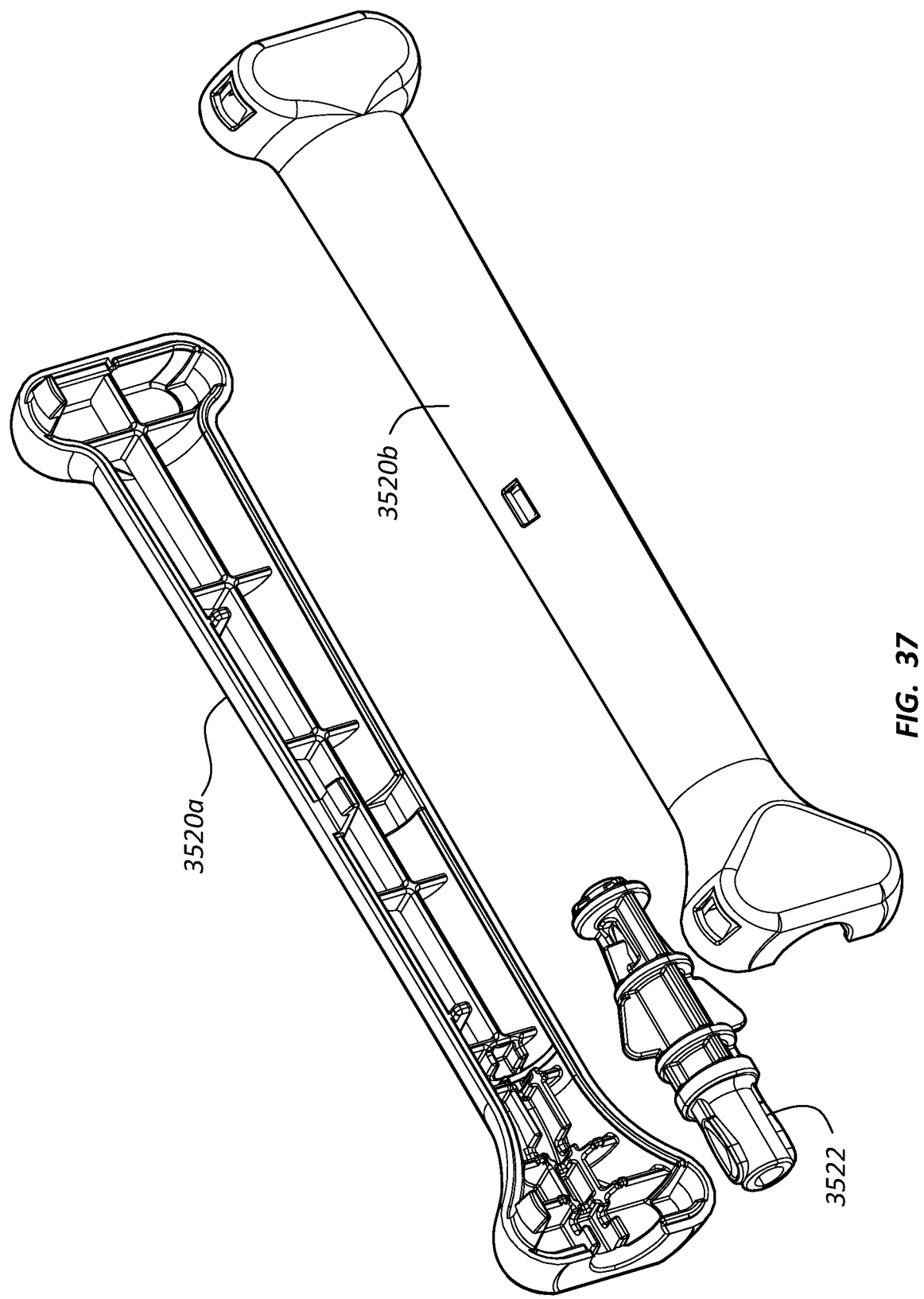
FIG. 37 illustrates a hub disposed in and extending from a handle in a catheter-tube tunneling assembly in accordance with some embodiments.

FIG. 35 illustrates a catheter-tube tunneling assembly 3500 in accordance with some embodiments. FIG. 36 illustrates a connection of a tunneling shaft 3510 to a handle 3520 in the catheter-tube tunneling assembly 3500. FIG. 37 illustrates a hub 3522 disposed in and extending from the handle 3520 of the catheter-tube tunneling assembly 3500.

As shown, the catheter-tube tunneling assembly 3500 can include the tunneling shaft 3510, which can be bendable or pre-bent for tunneling, the handle 3520 configured as an ambidextrous handle, and a lock collar 3530. The handle 3520 can include a hub 3522 disposed in and extending from a distal end portion of the handle 3520. The hub 3522 can be configured for insertion of a first end portion or a second end portion of the tunneling shaft 3510 into a socket 3523 of the hub 3522. The first end portion and the second portion of the tunneling shaft 3510 are each configured with a circumferential or wedge-shaped barb 3512 configured to interlock with a complementary feature in the socket 3523 of the hub 3522—as well as a complementary feature in the socket 3253 of the flow-directing cap 3252 (see FIG. 38). The circumferential or wedge-shaped barb 3512 of the tunneling shaft 3510 is further configured for subcutaneously tunneling the tunneling shaft 3510 in a patient. For example, when the circumferential or wedge-shaped barb 3512 at the first end portion of the tunneling shaft 3510 is interlocked with the complementary feature in the socket 3523 of the hub 3522, another circumferential or wedge-shaped barb 3512 at the second end portion of the tunneling shaft 3510 is configured for subcutaneously tunneling the tunneling shaft 3510 in a patient—or interlocking with the socket 3253 of the flow-directing cap 3252 to pull the catheter tube 150 through a subcutaneous tunnel previously made by the tunneling shaft 3510 (see FIGS. 39 and 40). The lock collar 3530 is configured to slide over the tunneling shaft 3510 and interlock with the hub 3522 by way of, for example, an over-the-hub-type clasp, to at least temporarily lock the tunneling shaft 3510 on the handle 3520.

Figure 38:
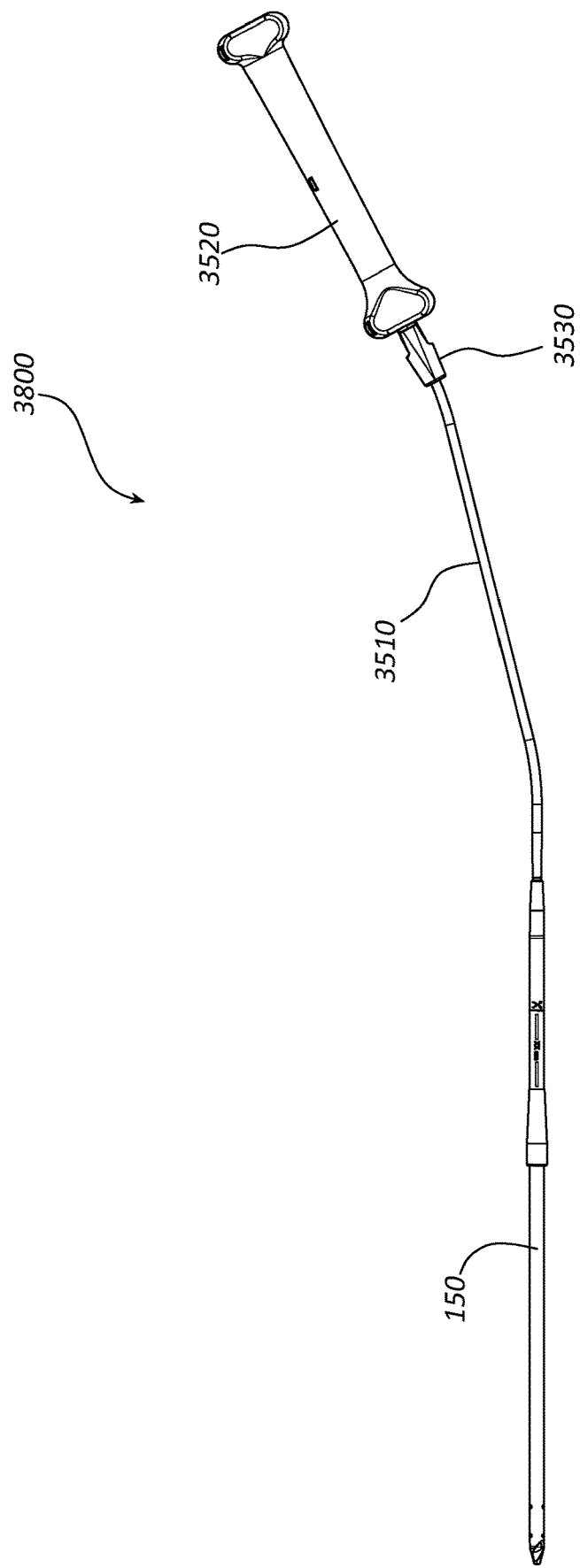
FIG. 38 illustrates a catheter-tube tunneling assembly with a catheter tube in accordance with some embodiments.
Figure 39:
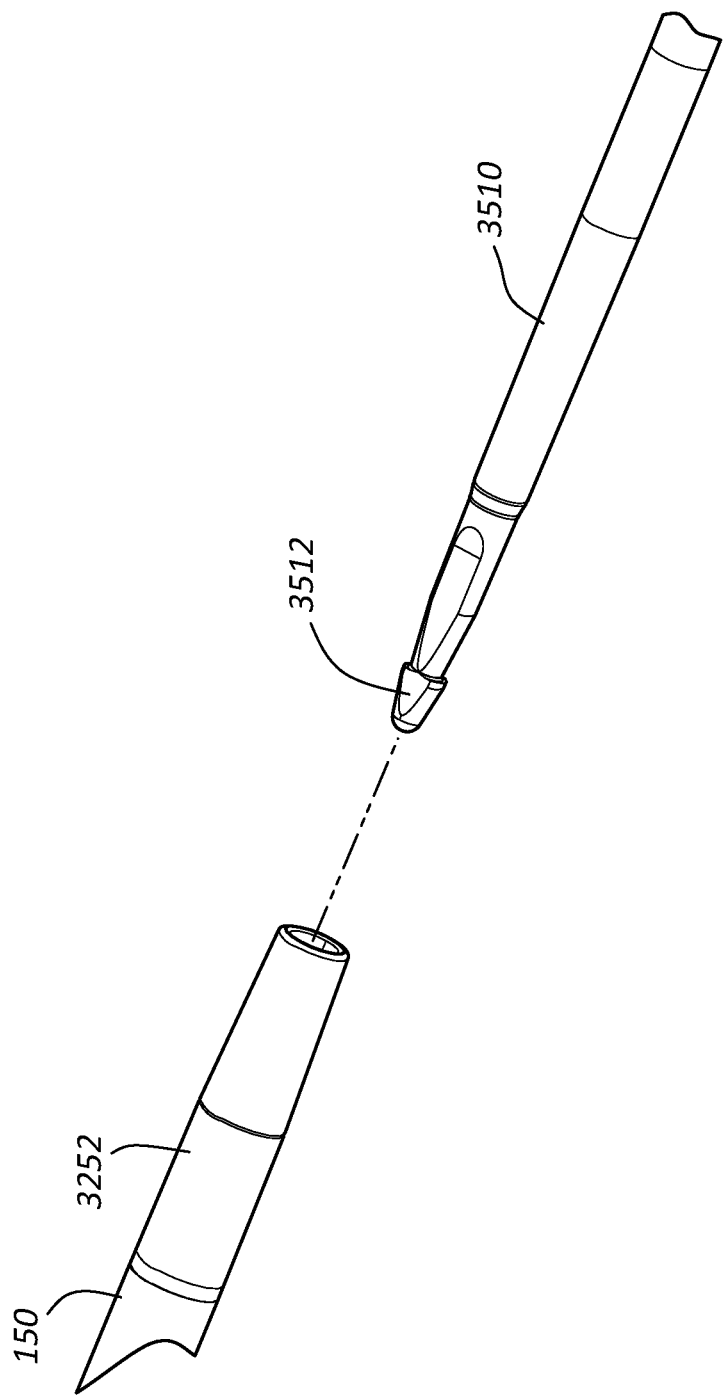
FIG. 39 illustrates a connection of a catheter tube to a tunneling shaft of a catheter-tube tunneling assembly in accordance with some embodiments.
Figure 40:
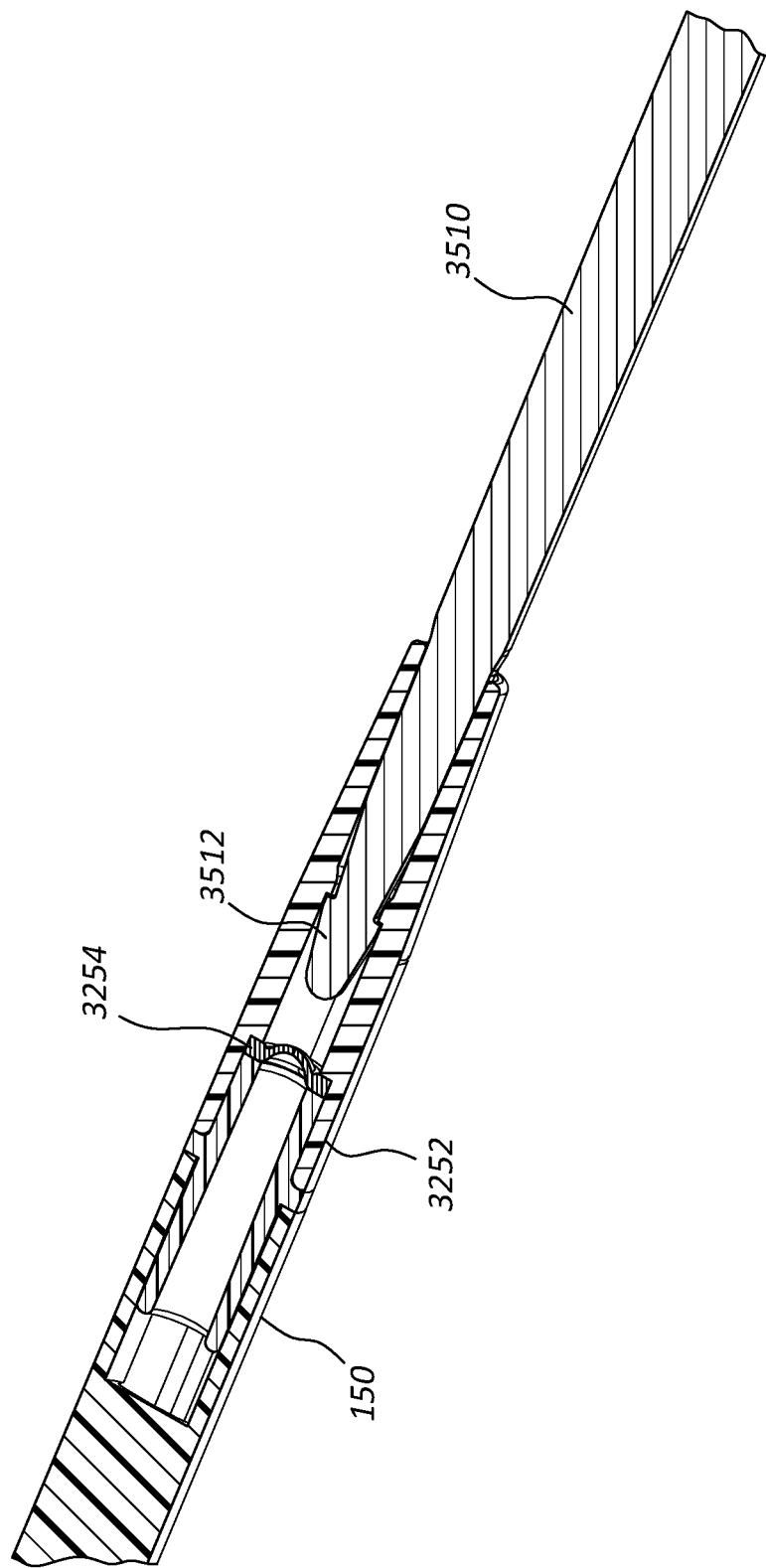
FIG. 40 illustrates a longitudinal cross section of a catheter tube connected to a tunneling shaft of a catheter-tube tunneling assembly in accordance with some embodiments.

FIG. 38 illustrates a catheter-tube tunneling assembly with a catheter tube in accordance with some embodiments. FIG. 39 illustrates a connection of a catheter tube to a tunneling shaft of the catheter-tube tunneling assembly in accordance with some embodiments. FIG. 40 illustrates a longitudinal cross section of a catheter tube connected to a tunneling shaft of a catheter-tube tunneling assembly in accordance with some embodiments.

As shown, the catheter-tube tunneling assembly 3800 can include the tunneling shaft 3510, the handle 3520 configured as the ambidextrous handle, and the lock collar 3530, as well the catheter tube 150, or the like (e.g., the catheter tube 650). Again, the first end portion and the second portion of the tunneling shaft 3510 are each configured with the circumferential or wedge-shaped barb 3512 to interlock with the complementary feature in the socket 3523 of the hub 3522 as well as the complementary feature in the socket 3253 of the flow-directing cap 3252 (see FIG. 38) about the proximal end portion of the catheter tube 150. FIG. 40 shows the complementary feature to be a circumferential ridge proximal to the valve 3254 in the flow-directing cap 3252, which precludes reopening the valve 3254 subsequent to priming the catheter tube 150.

F. Methods

Placing a catheter assembly for vascular access includes, in some embodiments, priming a pair of lumens such as the arterial lumen 153 and the venous lumen 155 of the catheter tube 150 of a first catheter assembly such the catheter assembly 3200 or 3300 with a priming fluid (e.g., sterile saline) from a distal end portion of the catheter tube 150; accessing a vessel in a vasculature of a patient from an access site on a neck of the patient; inserting the distal end portion of the catheter tube 150 into the vessel of the patient; creating an exit site on a chest of the patient; tunneling a proximal end portion of the catheter tube 150 as part of either the first assembly 3200 or a second catheter assembly such as the catheter assembly 3800 from the access site to the exit site; and connecting the proximal end portion of the catheter tube 150 to a proximal portion of a third catheter assembly (e.g., any catheter assembly configured for vascular access set forth herein selected from at least the catheter assemblies 100, 300-2200, and 2400-3000) by way of a connection mechanism (e.g., any connection mechanism set forth herein selected from at least the connection mechanisms 110, 310-2210, and 2410-3010) of the third catheter assembly, wherein the catheter tube 150 forms a distal portion of the third catheter assembly.

With respect the first catheter assembly 3200 or 3300, each catheter assembly includes the flow-directing cap 3252 about the proximal end portion of the catheter tube 150 and the priming adapter 3210 coupled to the priming stylet 3212 disposed in the distal end portion of the catheter tube 150. However, the catheter assembly 3300 further includes an over-the-wire ("OTW") stylet 3322 extending from the proximal end portion of the catheter tube 150 beyond the distal end portion of the catheter tube 150.

Priming the pair of lumens includes priming both the arterial lumen 153 and the venous lumen 155 of the pair of lumens through the priming stylet 3212 while the priming stylet 3212 is inserted into either lumen of the arterial lumen 153 or the venous lumen 155. If the OTW stylet 3322 is disposed in another lumen of the arterial lumen 153 or the venous lumen 155, priming the pair of lumens includes priming both the arterial lumen 153 and the venous lumen 155 while the priming stylet 3212 is inserted into one of the arterial lumen 153 or the venous lumen 155 and the OTW stylet 3322 is disposed in the other one of the arterial lumen 153 or the venous lumen 155. The priming adapter 3210 is configured with a Luer-tapered connector. Priming the pair of lumens further includes connecting a syringe to the priming adapter 3210 by way of the Luer-tapered connector and priming the pair of lumens with the priming fluid from the syringe, which can be sterile saline.

Placing the catheter assembly for vascular access can further include removing the priming adapter 3210 and the priming stylet 3212 before inserting the distal end portion of the catheter tube 150 into the vessel of the patient. Inserting the distal end portion of the catheter tube 150 into the vessel of the patient includes advancing the distal end portion of the catheter tube 150 into the vessel of the patient over a guidewire, optionally, disposed in the OTW stylet 3322.

Placing the catheter assembly for vascular access can further include tunneling the tunneling shaft 3510 from the access site to the exit site such as by pushing the tunneling shaft 3510 from the access site to the exit site to form a tract therebetween, which can be done by optionally first connecting the handle 3520 to the tunneling shaft 3510 for the tunneling. The tunneling shaft 3510 can be connected to the flow-directing cap 3252 to form the second catheter assembly 3800 (sans the handle 3250 and the lock collar 3530) for tunneling the proximal end portion of the catheter tube 150 from the access site to the exit site such as by pulling the proximal end portion of the catheter tube 150 through the tract, which can be done by optionally first connecting the handle 3520 to the tunneling shaft 3510 for the tunneling.

Placing the catheter assembly for vascular access can further include cutting the catheter tube 150 to length distal to the flow-directing cap 3252, thereby cutting off the flow-directing cap 3252 and exposing the arterial lumen 153 and the venous lumen 155 of the pair of lumens of the catheter tube 150; and connecting the arterial lumen 153 and the venous lumen 155 at the proximal end portion of the catheter tube 150 to the arterial lumen 133 and the venous lumen 135 of the pair cannulas 130 disposed in and extending from the bifurcated hub (e.g., any hub set forth herein selected from at least the hubs 120-3120) of the proximal portion of the third catheter assembly (e.g., any catheter assembly configured for vascular access set forth herein selected from at least the catheter assemblies 100, 300-2200, and 2400-3000).

The connection mechanism can be a collared connection mechanism (e.g., any collared connection mechanism set forth herein selected from at least the collared connection mechanisms 1210-2910) including a collar configured to fit over a proximal end portion of the catheter tube 150.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter assembly, comprising:
    a proximal portion, including:
        a bifurcated hub,
        a pair of polymer-coated cannulas partially disposed in and extending from a bore of the bifurcated hub, and
        a pair of extension tubes disposed in and extending from the bifurcated hub, wherein the pair of polymer-coated cannulas and the pair of extension tubes form a proximal pair of lumens extending through the proximal portion of the catheter assembly;
    a distal portion, including a catheter tube having a distal pair of lumens extending through the distal portion of the catheter assembly,
        wherein the catheter tube is configured to fit over the pair of polymer-coated cannulas to extend the proximal pair of lumens and the distal pair of lumens through an entirety of the catheter assembly as an extended pair of lumens; and
    a connection mechanism to connect the catheter tube to the pair of polymer-coated cannulas and provide a fluid-tight connection between the catheter tube and the pair of polymer-coated cannulas, the connection mechanism including a hub-based securement feature disposed within the bore of the bifurcated hub and oriented radially inward toward an axis of the bore in order to engage an outer surface of the catheter tube, the hub-based securement feature selected from the group consisting of one or more circumferential protrusions including rings or barbs, a plurality of radial protrusions including pillars, spikes, or barbs, and a combination thereof,
        wherein the hub-based securement feature is configured to displace in a proximal direction upon insertion of the catheter tube into the bore.

2. The catheter assembly of claim 1, wherein a polymer of the pair of polymer-coated cannulas is polyurethane.

3. The catheter assembly of claim 1, wherein the connection mechanism is collarless, the connection mechanism including the hub-based securement feature configured to interlock with a catheter tube-based securement feature, the hub-based securement feature including at least a lip at a distal end of the bore for the one or more circumferential protrusions, and the catheter tube-based securement feature including at least a circumferential barb configured to interlock with the lip of the bore.

4. The catheter assembly of claim 1, wherein the connection mechanism includes the one or more circumferential protrusions including rings or barbs.

5. The catheter assembly of claim 1, wherein the connection mechanism includes the plurality of radial protrusions including pillars, spikes, or barbs.

6. A catheter assembly, comprising:
    a proximal portion, including:
        a bifurcated hub,
        a pair of polymer-coated cannulas partially disposed in and extending from the bifurcated hub, and
        a pair of extension tubes disposed in and extending from the bifurcated hub,
            wherein the pair of polymer-coated cannulas and the pair of extension tubes form a proximal pair of lumens extending through the proximal portion of the catheter assembly;
    a distal portion, including a catheter tube having a distal pair of lumens extending through the distal portion of the catheter assembly,
        wherein the catheter tube is configured to fit over the pair of polymer-coated cannulas to extend the proximal pair of lumens and the distal pair of lumens through an entirety of the catheter assembly as an extended pair of lumens; and
    a collarless connection mechanism to connect the catheter tube to the pair of polymer-coated cannulas and provide a fluid-tight connection between the catheter tube and the pair of polymer-coated cannulas, the collarless connection mechanism including a hub-based securement feature configured as a clamping-style hub for clamping the catheter tube on the pair of polymer-coated cannulas, wherein the clamping-style hub includes gripping features configured to engage an outer surface of the catheter tube, wherein:
    the hub-based securement feature includes two arms configured to close around the catheter tube,
    the two arms are hingedly coupled with the clamping-style hub, and
    the two arms include fasteners configured to fasten the two arms together when the two arms are closed.

* * * * *